United States Patent
Berecz et al.

(10) Patent No.: US 12,258,348 B2
(45) Date of Patent: Mar. 25, 2025

(54) METHOD FOR THE PRODUCTION OF LUMATEPERONE AND ITS SALTS

(71) Applicant: EGIS GYOGYSZERGYAR ZRT., Budapest (HU)

(72) Inventors: Gábor Berecz, Budapest (HU); Bálint Nyulasi, Budapest (HU); Mátyás Milen, Budapest (HU); Gyula Simig, Budapest (HU); András Mravik, Budapest (HU); Gábor Németh, Budapest (HU); Adrienn Keszthelyi, Budapest (HU); Beatrix Bali, Budapest (HU); Balázs Volk, Budapest (HU); László Szlávik, Budapest (HU); Zoltán Varga, Budapest (HU); Daniel Ulej, Budapest (HU)

(73) Assignee: EGIS GYOGYSZERGYAR ZRT., Budapest (HU)

( * ) Notice: Subject to any disclaimer, the term of this patent is extended or adjusted under 35 U.S.C. 154(b) by 92 days.

(21) Appl. No.: 18/110,570

(22) Filed: Feb. 16, 2023

(65) Prior Publication Data

US 2023/0331727 A1    Oct. 19, 2023

Related U.S. Application Data

(62) Division of application No. 16/767,057, filed as application No. PCT/HU2018/050050 on Nov. 27, 2018, now Pat. No. 11,655,251.

(30) Foreign Application Priority Data

| Nov. 27, 2017 | (HU) | P1700491 |
| Nov. 27, 2017 | (HU) | P1700492 |
| Nov. 27, 2017 | (HU) | P1700493 |
| Apr. 16, 2018 | (HU) | P1800126 |

(51) Int. Cl.
| C07D 471/16 | (2006.01) |
| C07B 57/00  | (2006.01) |
| C07C 235/74 | (2006.01) |
| C07C 309/30 | (2006.01) |
| C07C 309/35 | (2006.01) |

(52) U.S. Cl.
CPC ............ *C07D 471/16* (2013.01); *C07B 57/00* (2013.01); *C07C 235/74* (2013.01); *C07C 309/30* (2013.01); *C07C 309/35* (2013.01); *C07B 2200/07* (2013.01); *C07B 2200/13* (2013.01)

(58) Field of Classification Search
None
See application file for complete search history.

(56) References Cited

FOREIGN PATENT DOCUMENTS

| WO | 00/77002 A1    | 12/2000 |
| WO | 2008/112280 A1 |  9/2008 |
| WO | 2009/114181 A2 |  9/2009 |
| WO | 2018/031535 A1 |  2/2018 |
| WO | 2018/19646 A1  | 10/2018 |

OTHER PUBLICATIONS

International Search Report dated Apr. 5, 2019 issued in corresponding PCT/HU2018/050050 application (5 pages).

Maier et al: "Separation of Enantiomers: Needs, Challenges, Perspectives", Journal of Chromatography A, vol. 906, Issues 1-2, pp. 3-33, Jan. 2001 ; DOI:10.1016/S0021-9673(00)00532-X.

*Primary Examiner* — Zinna Northington Davis
(74) *Attorney, Agent, or Firm* — Millen, White, Zelano & Branigan, P.C.; Csaba Henter

(57) ABSTRACT

Method for the production of formula (I) lumateperone or its acid addition salts so that the enantiomer compound with stereochemistry 6bR,10aS

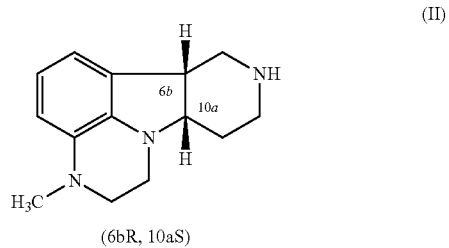

is separated form the cis racemate using resolution and the formula (II) stereoisomer is alkylated with 4-halo-4'-fluoro butyrophenone (X=I, Br, Cl) to produce the formula (I) lumateperone, or optionally its acid addition salt. The object of the invention also relates to the amorphous form of the morphologically uniform p-toluenesulfonic acid salt of lumateperone and to the naphthalene-2-sulfonic acid salt of lumateperone, to the 1:2 stoichiometry salt of lumateperone formed with naphthalene-2-sulfonic acid.

20 Claims, 13 Drawing Sheets

METHOD FOR THE PRODUCTION OF LUMATEPERONE AND ITS SALTS

The invention relates to the production of formula (I) lumateperone (ITI-007)

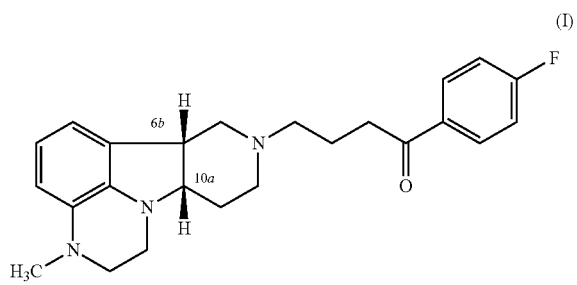 [SMILES: CN1CCN2c3c(cccc31)[C@@H]1CN(CCCC(=O)c3ccc(F)cc3)CC[C@@H]12]

(I)

with chemical name 1-(4-fluorophenyl)-4-((6bR,10aS)-3-methyl-2,3,6b,9,10,10a-hexahydro-1H,7H-pyrido[3′,4′: 4,5]pyrrolo[1,2,3-de]quinoxaline-8-yl)-butane-1-one—and to the new pharmaceutical industry intermediate products and to their production process, as well as to the crystalline and amorphous salts of lumateperone formed with p-toluenesulfonic acid, and to its salts formed with naphthalene-2-sulfonic acid, which are preferably produced with the method according to the present invention. More specifically the object of the invention relates to a new method for the production of the formula (II) key intermediate of lumateperone, the crystalline form of the formula (II) compound, the salt of the formula (II) compound formed with (+)-dibenzoyl-D-tartaric acid mono(dimethylamide) (VI) and the dihydrochloride salt of the formula (II) compound (II-2HCl), furthermore the production of lumateperone from the formula (II) intermediate obtained with the new method and from its salts, as well as the lumateperone monotosylate amorphous form, and to the salt of lumateperone formed with p-toluenesulfonic acid, in which the molar ratio of lumateperone to p-toluenesulfonic acid is 1:2, and to the salt of lumateperone produced with naphthalene-2-sulfonic acid, in which, in a preferable case, the molar ratio of lumateperone to naphthalene-2-sulfonic acid is 1:1 or 1:2. Furthermore, the object of the invention relates to pharmaceutical preparations containing the salts listed above, their production and use in the treatment of schizophrenia, bipolar depression and other diseases of the central nervous system.

THE STATE OF THE ART

International patent application number WO2000077002 discloses the production of a racemate containing lumateperone and its enantiomer, then formula (I) lumateperone is obtained by resolution the latter with chiral HPLC (Reaction Scheme 1 as provided in FIG. 11). This synthesis pathway was later published in a scientific journal (J. Med. Chem. 2014, 57, 2670). The method, due to the resolution step performed with chiral HPLC, is obviously unsuited for industrial upscaling.

International patent application number WO2008112280 discloses two methods for the production of formula (I) optically active lumateperone (Reaction Scheme 2 as provided in FIG. 12). An early intermediate is resolved which does not contain the quinoxaline structural part. Two methods are disclosed for constructing this latter part (pathways A and B). Among the described synthesis pathways only pathway A was shown with examples. Pathway B was only described in examples in the aforementioned scientific article for the synthesis of the racemic cis compound, in other words leaving out the resolution steps.

The advantage of the syntheses described in international patent application number WO2008112280 over the synthesis pathway described in international patent application number WO2000077002 is that the amount of material loss is reduced with the resolution after the second step. Its disadvantage, however, is that the entire ring system is not established in the Fischer synthesis, therefore it is necessary to construct the fourth ring at a later stage, the synthetic implementation of which demands vigorous conditions and a reaction time of several days. A further significant disadvantage is that the reduction of the double bond of indole using triethylsilane can only be realised in trifluoroacetic acid (hereinafter: TFA). Catalytic hydrogenation cannot be employed due to the presence of the bromine atom. TFA cannot be substituted for another solvent (such as acetic acid or a mixture of acetic acid/trifluoroacetic acid) in the triethylsilane reduction. The use of a large amount of the dangerous and expensive TFA, also used as a solvent, also represents a problem. The regeneration of TFA is difficult to perform due to the surplus triethylsilane used for the reduction.

The above processes are lengthy, difficult to reproduce and contain steps that are less suited for upscaling. A particular disadvantage is that a dark brown oil is obtained in the course of the removal of the N-ethoxycarbonyl group, which is obviously unsuited for conventional purification procedures, and, according to HPLC tests, only contained 88.1% of the formula (II) final intermediate.

A further disadvantage of the synthesis disclosed in patent application number WO 2008112280A1 is that the final product is a brown coloured liquid. In the course of production, in the final step the hydrochloric acid salt of the final product is isolated, then the filtered salt is transformed into a base in the presence of an organic solvent, then the base obtained from the organic phase is purified using chromatography. According to an alternative procedure it is first taken into an aqueous solution with hydrochloric acid, then transformed into a base after washing the acid solution with an organic solvent, then taken into an organic solvent, which is evaporated to obtain the final product. The complex purification process is obviously required because there is no possibility to remove the contaminants of the intermediates in the course of the synthesis leading to the final product. No other characterisation is provided for the final product apart from its mass, colour and state. Therefore, there is no information available about its chemical or stereochemical purity. As the formulation of liquid state active substances is very difficult in the pharmaceutical industry, it is of primary importance to have active substances in solid state and at the appropriate level of chemical purity. Patent application publication number WO 2009/114181 describes two polymorphous forms of the tosylate salt as a crystalline derivative of lumateperone. Patent application publication number WO 2017/172784 describes the production of oxalate, 4-amino-salicylate and cyclamate salts. According to patent application publication number WO 2017/172811 cocrystals were formed with nicotinamide and isonicotinamide. However, the salt and cocrystal formation did not lead to active substances that had purity that is acceptable in the pharmaceutical industry, as the purity of the salts and the cocrystals did not even reach chemical purity of 97%. In addition, where the yield was given for the salt or cocrystal formation, it was low.

In the patent application number WO 2018/031535 published on 15 Feb. 2018, the authors describe new bis-tosylates. According to page 16 of the application, the lumateperone base or monotosylate salt used for the production of the bis-tosylates may be produced according to that described in patent application number WO 2008/112280, or WO2009/114181. As these processes do not make it possible to make chemically pure product without making use of chromatography methods, the salts presented here could only be produced by using a chiral chromatography technique according to the state of the art. At the same time, although ten salt-production examples are presented in the application, not even one of the salts is characterised using analytical methods apart from x-ray powder diffractograms, and their yields are not even provided. The enantiomer purity and chemical purity are not known about the products obtained either. Therefore, a person skilled in the art is unable to decide whether these salts have any advantage over the previously disclosed monotosylate salts. The state of the art is summarised in the following table:

TABLE 1

| Salt | yield | purity [HPLC] | Literature |
|---|---|---|---|
| Tosylate (polymorph A) | 84% | 93.20% | WO 2009/114181 |
| Tosylate (polymorph B) | 65.72% | 96.40% | |
| Tosylate (polymorph B) | 81.59% | n.a. | |
| Tosylate (polymorphology not known) | 78.38% | n.a. | |
| Tosylate (polymorphology not known) | 61% | 96.90% | |
| Oxalate salt | n.a. | 91% | WO 2017/172784 |
| 4-aminosalicylate salt | n.a. | 78% | |
| Cyclamate salt | n.a. | 67% | |
| Cocrystal formed with isonicotinamide | n.a. | 95% | WO 2017/172811 |
| Cocrystal formed with nicotinamide | n.a. | n.a. | |

At present, according to the state of the art, lumateperone suitable for use in the pharmaceutical industry cannot be produced without the use of a chiral chromatography process. In addition, lumateperone salt with chemical purity of 97% cannot be produced either using salt formation. This is the reason why it is necessary to develop an active substance, preferably a lumateperone salt that can be produced with high purity, that is stable and preferably morphologically uniform. The objective of the invention, then, was to overcome the disadvantages of the known methods, especially the chiral purification step and develop a novel method that can be implemented simply and economically at industrial scales with which lumateperone salts can be produced that are suitable for use in pharmaceutical preparations and for the treatment of the aforementioned illnesses/disorders.

THE ESSENCE OF THE INVENTION

The essence of the invention is a novel method for the production of the formula (I) lumateperone or its acid addition salts so that the enantiomers forming the formula (IV) cis racemate are isolated

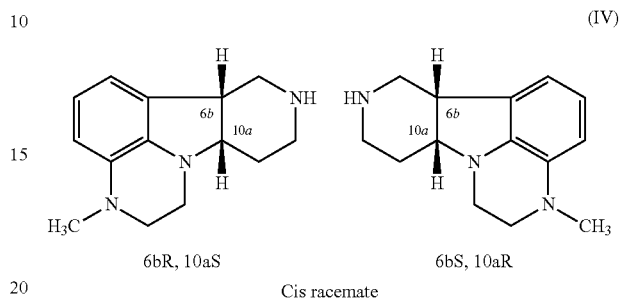

(IV)

6bR, 10aS      6bS, 10aR

Cis racemate and the formula (II) compound obtained in this way with stereochemistry 6bR,10aS

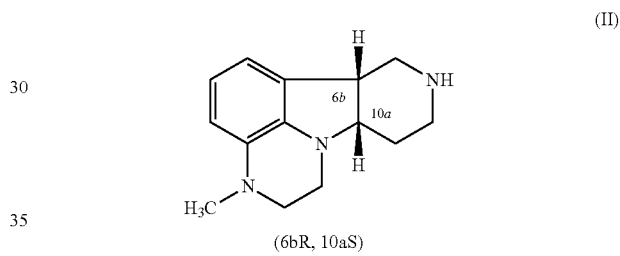

(II)

(6bR, 10aS)

is alkylated with 4-halo-4'-fluoro butyrophenone (X=I, Br, Cl) into formula (I) lumateperone, and optionally transformed into an acid addition salt. According to a preferable embodiment of the invention the lumateperone base is transformed into a salt formed preferably with p-toluenesulfonic acid or with naphthalene-2-sulfonic acid, even more preferably into an amorphous or crystalline salt formed with formula

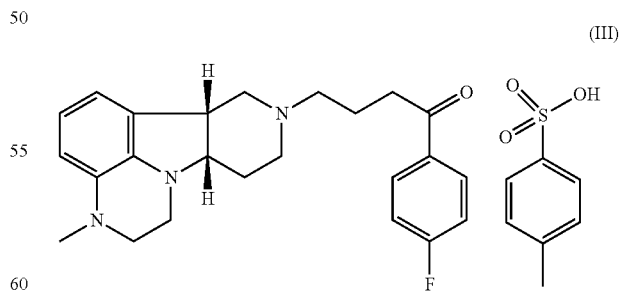

(III)

p-toluenesulfonic acid, in which the molar ratio of lumateperone to p-toluenesulfonic acid is 1:1, or into a salt of lumateperone formed with naphthalene-2-sulfonic acid, preferably into the formula (VIII) salt formed with naphthalene-2-sulfonic acid,

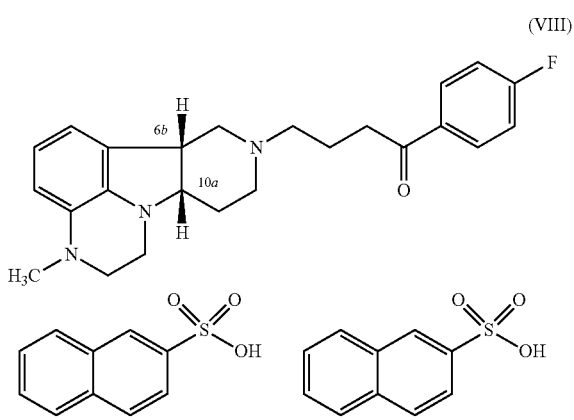

(VIII)

in which the molar ratio of lumateperone to naphthalene-2-sulfonic acid is 1:2, or into the formula (X) salt formed with naphthalene-2-sulfonic acid,

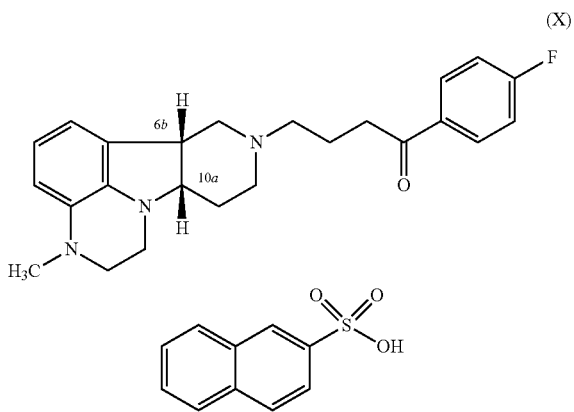

(X)

in which the molar ratio of lumateperone to naphthalene-2-sulfonic acid is 1:1, or into the formula (IX) salt,

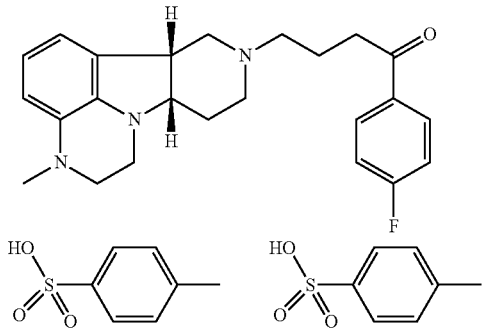

(IX)

in which the molar ratio of lumateperone to p-toluenesulfonic acid is 1:2. It was surprising to experience that the salts isolated in this way have a chemical purity and stereochemical purity that are suitable for use in the pharmaceutical industry, with a morphological uniform crystalline or amorphous structure and suitable chemical stability.

More specifically, according to a preferable embodiment of the method according to the invention the isolation of the stereoisomers of the formula (IV) compound is performed without the use of a chiral chromatography process.

According to a preferable embodiment of the invention the isolation of the stereoisomers of the formula (IV) compound is performed using a resolution process. The resolution is preferably performed so that the formula (IV) compound is reacted with one of the enantiomers of a chiral acid, then the one stereoisomer salt is isolated from the reaction mixture, and then the formula (II) compound with stereochemistry 6bR,10aS or its salt is alkylated with formula (VII)

(VII)

4-halo-4'-fluoro butyrophenone (X=I, Br, Cl) into formula (I) lumateperone, or, optionally, transformed into its acid addition salt. The alkylation step may also be carried out by measuring the formula (II) compound with the stereochemistry 6bR,10aS formed during the resolution step as a base into the reaction mixture used for alkylating, it may also be carried out by measuring it in as a salt, in the presence of an acid-binder and transforming it into a base in the reaction mixture, or by first transforming the salt into a base, then alkylating the base after isolating it from the salt-forming component.

According to a very preferable embodiment of the invention the production of the formula (I) lumateperone or of its acid addition salt is carried out by reacting the formula (IV) compound, which is a cis racemate according to its spatial structure, with the formula (V) compound

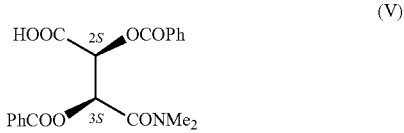

(V)

then the formula (VI) salt,

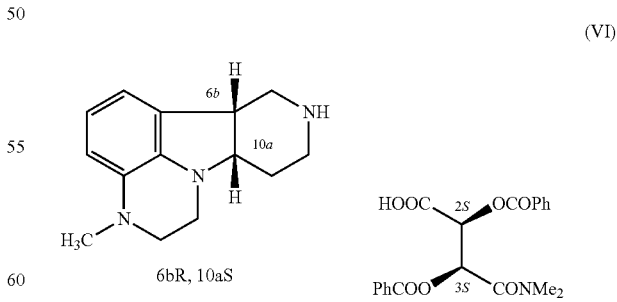

(VI)

which is the desired stereochemical cis enantiomer salt, is isolated. This enantiomer salt is transformed into a base, or into another salt, such as hydrochloride salt. The salt or base obtained in this way is alkylated. The process may also involve transforming another salt, e.g. made using hydrochloric acid, from the salt made from the chiral acid into a base and then by isolating the obtained base in crystalline form before alkylation.

The object of the invention also relates to the dihydrochloride salt of the formula (II) base.

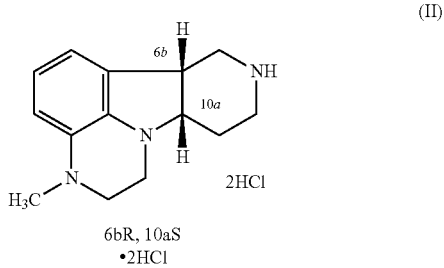 [SMILES: CN1CCN2c3c(cccc31)[C@@H]1CNCC[C@@H]12]

(II)

6bR, 10aS
•2HCl

This salt, either transformed into a base or in the presence of an acid-binder, is especially suitable for being alkylated into formula (I) lumateperone with formula (VII) 4-halo-4'-fluoro butyrophenone or, optionally, into an acid addition salt. The crystalline form of the formula (II) compound, the formula (VI) salt, and its dihydrochloride salt [(II)·2HCl] are unknown in the prior art.

Our method is summarised in reaction scheme 3 as provided in FIG. 13.

A DETAILED DESCRIPTION OF THE INVENTION

Therefore, the basis of the invention is the recognition that the stereoisomers of the racemic formula (IV) compound described in international patent application number WO 2000077002 and the scientific publication *J. Med. Chem.* 2014, 57, 2670-2682 are isolated preferably without the use of a chromatography process, and the formula (II) stereoisomer obtained in this way with stereochemistry 6bR,10aS is produced at a very high chemical and stereochemical purity level contrary to the methods according to the state of the art. This makes it possible, by the alkylating of the formula (II) compound or its salts obtained in this way, to produce lumateperone salts with a level of chemical and enantiomer purity much higher than that known of from the state of the art (see above table) so that they may be directly used for pharmaceutical production. A surprising and unexpected characteristic of the formula (II) compound is that it may also be produced in crystalline form using the method according to the invention. This is one of the unexpected recognitions forming the basis of the present invention which made it possible to perform the resolution step without the use of chiral chromatography in one of the intermediate phases of the synthesis. It is especially preferable and unexpected that the production of the formula (II) compound according to the invention makes it possible to remove the contaminants originating from the previous phases of the synthesis in the step before the final product. In other words, the present method makes it possible, contrary to the methods according to the state of the art, to produce, for example lumateperone tosylate and naphthalene-2-sulfonate salts at very high levels of chemical and stereochemical purity without the use of chiral chromatography isolation. Therefore the object of the invention also includes the salts produced in this way.

The object of the invention also includes, therefore, the formula (III) amorphous and crystalline salt of formula (I) lumateperone formed with p-toluenesulfonic acid, in which the molar ratio of lumateperone to p-toluenesulfonic acid is 1:1, its formula (IX) salt, in which the molar ratio of lumateperone to p-toluenesulfonic acid is 1:2, its formula (X) salt, in which the molar ratio of lumateperone to naphthalene-2-sulfonic acid is 1:1, and its formula (VIII) salt, in which the molar ratio of lumateperone to naphthalene-2-sulfonic acid is 1:2. It was surprising to find that these salts are morphologically uniform, these salts may be produced in a form with the high level of chemical and enantiomer purity that is required in the pharmaceutical industry without chiral chromatographic purification, with the use of the synthesis forming the object of the invention. The solid, morphologically uniform amorphous salt complies with the requirements of formulation, which makes it possible to use the salts according to the invention as active substances in pharmaceutical preparations, which the lower level of the chemical purity of the salts according to the state of the art does not make possible without chromatographic purification.

From the lumateperone produced by alkylating the formula (II) compound or its salts obtained in this way according to the present invention lumateperone p-toluenesulfonic acid amorphous salt with a much higher level of chemical purity than that known of from the state of the art (see above table), with a level of chemical purity and enantiomer purity that may be directly used in the pharmaceutical manufacture, in which the molar ratio of lumateperone to p-toluenesulfonic acid is 1:1, the formula (IX) salt, in which the molar ratio of lumateperone to p-toluenesulfonic acid is 1:2, the formula (X) salt, in which the molar ratio of lumateperone to naphthalene-2-sulfonic acid is 1:1, and the formula (VIII) salt, in which the molar ratio of lumateperone to naphthalene-2-sulfonic acid is 1:2 can be produced.

The lumateperone and its salts produced according to the invention, as well as all of the compounds used as starting materials and intermediates and forming the object of the invention each contain two chiral carbon atoms, a so-called asymmetric centre.

The common structural element of the compounds is a four-ring structure in which the atoms comprising the ring are identified with the following numbering:

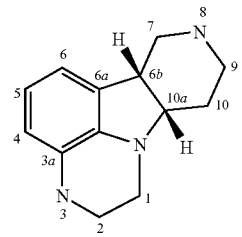

The spatial position of each of the hydrogen atoms on the chiral carbon atoms of the ring system, carbon atoms 6b and 10a determines the four various stereoisomers as follows: There are two isomers where the two hydrogen atoms fall on the same side of the ring system:
  the configurations (6bR,10aS) or (6bS,10aR). These are called cis compounds, while those compounds in which the two hydrogen atoms are on opposite sides of the ring system:
  the configurations (6bS,10aS) or (6bR,10aR), are called trans isomers.

By using the syntheses according to the state of the art a formula (IV) cis racemic compound can be produced which is a mixture of the two cis enantiomers, i.e. the compounds containing chiral carbon atoms with the configurations (6bR, 10aS) and (6bS,10aR). This mixture is formed in such a way so that the trans compounds, in which the configuration of the chiral carbon atoms is (6bS,10aS) or (6bR,10aR), essentially do not occur, or the formula (IV) racemic cis isomer can be effectively isolated from them. Two solutions have been elaborated in the syntheses according to the state of the art for the production of enantiomer-pure lumateperone.

According to the example of the publication patent application number WO 2000077002 the desired racemic cis final product was separated using a chiral chromatography method into lumateperone base (eutomer) and its antipode (distomer). The method, i.e. the industrial implementation of chiral chromatography, is, if at all possible, extremely expensive. The other possibility according to the publication specification number WO 2008112280 is that the racemate is isolated by resolution in an early step of the 9-step synthesis, then the appropriate enantiomer is transformed into lumateperone in the course of several steps. This latter method involves the synthesis passing through numerous intermediates that are difficult or impossible to purify, and at the end a product of only very poor chemical purity can be obtained that cannot be purified using industrial methods. In addition to enantiomer purity, chemical purity is also of outstanding importance in the case of the production of a pharmaceutical active substance, as high levels of contamination, or many unknown contaminant intermediates and side products make it impossible to use the active substance in the medicine.

Enantiomer purity is understood to mean how much of the desired enantiomer is present in the product obtained. In the present application an enantiomer-pure compound is deemed that compound in which the amount of the desired enantiomer is greater than 97%, preferably greater than 99%, even more preferably greater than 99.5%, i.e. the detectable amount of the undesired enantiomer is less than 3%, preferably less than 1%, and most preferably less than 0.5%. Amount is understood as referring to the mass of the components. As the components are identical in terms of all characteristics except for the spatial positions of the chiral carbon atoms, the area ratio of the signals of the individual enantiomers measured during chromatography measurement (e.g. chiral chromatography) is equal to the mass ratio of the enantiomers present in the sample. In other words the mass ratio can also be characterised by the area ratio.

In the present case a product may be said to be a enantiomer-pure product, such as the formula (I) lumateperone or its salt, the formula (II) precursor or its salt, such as the amorphous or crystalline salt of the formula (III) compound, in which the molar ratio of lumateperone to p-toluenesulfonic acid is 1:1, its formula (IX) salt, in which the molar ratio of lumateperone to p-toluenesulfonic acid is 1:2, or the salt of lumateperone and naphthalene-2-sulfonic acid, preferably the formula (X) salt, in which the molar ratio of lumateperone to naphthalene-2-sulfonic acid is 1:1, even more preferably the formula (VIII) salt, in which the molar ratio of lumateperone to naphthalene-2-sulfonic acid is 1:2, in which the amount of the enantiomer containing the 6bR,10aS configuration carbon atoms is greater than 97%, preferably greater than 99%, even more preferably greater than 99.5%.

In other words this could also be defined by calling that that formula (I) lumateperone or its salt, the formula (II) precursor or its salt, such as the amorphous or crystalline salt of the formula (III) compound, in which the molar ratio of lumateperone to p-toluenesulfonic acid is 1:1, its formula (IX) salt, in which the molar ratio of lumateperone to p-toluenesulfonic acid is 1:2, or the salt of lumateperone and naphthalene-2-sulfonic acid, preferably the formula (X) salt, in which the molar ratio of lumateperone to naphthalene-2-sulfonic acid is 1:1, even more preferably the formula (VIII) salt, in which the molar ratio of lumateperone to naphthalene-2-sulfonic acid is 1:2, an enantiomer-pure product in which the amount of the enantiomer containing the 6bS, 10aR configuration carbon atoms is less than 3%, preferably less than 1%, even more preferably less than 0.5%.

The object of the invention then is the formula (II) precursor of the formula (I) lumateperone or its salt, the amorphous or crystalline salt of the formula (III) lumateperone, in which the molar ratio of lumateperone to p-toluenesulfonic acid is 1:1, its formula (IX) salt, in which the molar ratio of lumateperone to p-toluenesulfonic acid is 1:2, or the salt of lumateperone and naphthalene-2-sulfonic acid, preferably the formula (X) salt, in which the molar ratio of lumateperone to naphthalene-2-sulfonic acid is 1:1, even more preferably its formula (VIII) salt, in which the molar ratio of lumateperone to naphthalene-2-sulfonic acid is 1:2, which has a chemical purity greater than 97%, preferably greater than 99%, even more preferably greater than 99.5%, and/or which has an enantiomer purity greater than 97%, preferably greater than 99%, even more preferably greater than 99.5%.

In the present application the chemical purity of a product or intermediate is understood to mean how much contaminant the desired isomer compound contains. The percentage contaminant content is understood to mean the contaminant content calculated on the basis of HPLC area. In other words, when the purity of a compound is given as a percentage, then this is the percentage purity measured using HPLC, in percentage of the measured area. In the case of purity measured with chiral HPLC, the enantiomer purity is also determined by measuring the amounts of the individual enantiomers.

A chemically pure compound as used in the specification of the present invention means a product/compound in which, apart from the desired enantiomer, or, in the case of a racemic compound, apart from the desired racemic compound, the amount of the other chemical contaminants does not reach 3%, preferably does not reach 1%, and even more preferably does not reach 0.5%. In other words it may also be defined by stating that in the case of an enantiomer the content of the desired enantiomer is greater than 97%, preferably greater than 99%, even more preferably greater than 99.5% in the product/compound.

In the method according to the invention the formula (II) enantiomer pure key intermediate of lumateperone is preferably isolated from the formula (IV) racemate using a resolution process. The essence of this is that the racemic cis compound is reacted with a chiral acid. Those acids are called chiral acids that have at least one chiral carbon atom and that have, at least theoretically, an enantiomer pair in which every chiral carbon atom has the opposite configuration. The two salts formed form a diastereomer salt pair, in other words the spatial positions of the chiral carbon atoms of the base in the salt will be different, but they will be the same in the acid component. Usually, due to the differing solubility of the diastereomer salt pairs, the one enantiomer salt precipitates from the solution more or less pure, which can then be isolated. When the one enantiomer is removed from the reaction mixture in the course of the resolution process, the ratio of the other enantiomer in the mother liquor increases in proportion with the removed enantiomer, in other words an enantiomer-enriched solution is obtained. These are so-called enantiomer or stereoisomer enriched solutions. If necessary the other enantiomer can also be separated from these. Separation and isolation are used as synonyms. In all cases these terms mean that two compounds with different physical characteristics are separated using a known chemical, physical-chemical or technological step or steps. The chiral acid used for resolution the formula (II) compound according to the present application means certain enantiomers/diastereomers of the chiral acid. A racemic mixture of the enantiomers or diastereomers of the chiral acid in which the opposite spatially positioned enantiomers/diastereomers of the chiral acid are present in equal proportions cannot be used as a chiral acid for resolution. The enantiomer purity of the chiral acids used for the resolution of the formula (II) compound according to the invention is preferably greater than 55%, even more preferably greater than 75%, most preferably greater than 95%. The enantiomer purity of chiral acids used in practice is usually greater than 97.5%, preferably greater than 99%, and most preferably greater than 99.5%. Enantiomer purity is understood to mean the amount of the desired enantiomer that is present in the obtained product.

The separation may be performed, therefore, by filtration of the solid parts, decanting the mother liquor, or, optionally, by using extraction, or the desired product may even be separated using a chromatography method, or the undesired enantiomer contaminant, intermediate product and/or other contaminants can be separated from the desired product. The product may also be isolated by evaporating a part of the reaction mixture, in other words by concentrating the reaction mixture or solution, then filtering out the solid material precipitating out of the higher concentration solution. A person skilled in the art is able to perform these operations using steps and equipment usually found in the chemicals industry on the basis of his/her general knowledge.

The chemical purity of the formula (III) amorphous or crystalline salt of lumateperone formed with p-toluenesulfonic acid, of the formula (IX) salt, in which the molar ratio of lumateperone to p-toluenesulfonic acid is 1:2, or of the salt of lumateperone and naphthalene-2-sulfonic acid, preferably of the formula (X) salt, in which the molar ratio of lumateperone to naphthalene-2-sulfonic acid is 1:1, or even more preferably of the formula (VIII) salt, in which the molar ratio of lumateperone to naphthalene-2-sulfonic acid is 1:2, according to the invention is greater than 97%, preferably greater than 99%, even more preferably greater than 99.5%, and/or their enantiomer purity is greater than 97%, preferably greater than 99%, even more preferably greater than 99.5%.

The compounds produced and used in the present invention, if in solid state, may have a crystalline or amorphous structure. Morphological uniformity is important from the point of view of use, especially in the case of pharmaceutical active substances, because the various crystalline and amorphous forms of active substances have varying physical properties, such as solubility, which may even affect the absorption of a medicinal product. Morphological properties are also important for intermediates and active substances, as a uniform morphology product facilitates processing, such as dosing, tableting, as then the material to be processed has uniform physical properties, such as being free-flowing. A solid material is deemed to be morphologically uniform according to the description of the present invention if at least 95% of the mass of the substance, preferably 99%, most preferably 99.5% comprises a morphologically specific, uniform crystalline structure. In other words the solid material according to the invention is morphologically uniform if a maximum of 5% of the mass of the solid material according to the invention, preferably 3%, even more preferably a maximum of 1%, most preferably a maximum of 0.5% has a different crystalline or amorphous morphology to the main mass of the product. An amorphous product is deemed to be morphologically uniform if a maximum of 5% of its mass, preferably a maximum of 3% of its mass, more preferably up to 1% of its mass, most preferably 0.5% of its mass comprises crystalline product. The identification of the crystal structure and, within this, the determination of the proportions of the amounts of the individual crystal forms may be performed by evaluating x-ray powder diffractograms, on the basis of the general knowledge of a person skilled in the art. This may also be carried out by comparing the x-ray powder diffraction peaks characteristic of the various uniform crystalline forms with the diffractogram of the mixture.

In the present invention one of the chemical steps is the alkylating of an amine. The alkylation may also be performed by adding the alkylating agent to the base to be alkylated, then, if needed, binding the hydrochloric acid, hydrogen bromide or hydrogen iodide formed in the course of the reaction using an organic or inorganic acid-binder. With respect to that the formula (II) compound acts as a base, if no acid-binder is added to the reaction mixture this base will be transformed into a salt and will not be used up, thereby reducing yield. An alternative procedure is that the salt of the base to be alkylated is added, then the base must be released in the reaction mixture ("in situ"). The alkylating may also be carried out by dissolving the salt of the base to be alkylated in water, then by releasing the base to be alkylated by adding base, which is then re-dissolved (extracted) in an organic solvent, then with the solution obtained being dried (dehydrated) if necessary, and optionally partially or completely evaporated, the base to be alkylated is added to the reaction mixture.

The chemical purity of the formula (II) compound produced according to the invention, of its salts produced according to the invention, and of the formula (I) lumateperone base or of its salts produced from any of these is preferably greater than 97%, more preferably greater than 99%, even more preferably greater than 99.5%, in such a way that preferably the enantiomer purity of these compounds is also greater than 97%, preferably greater than 99%, even more preferably greater than 99.5%. The alkylating of the high purity formula (II) compound or of its salt, in other words with a purity greater than 97%, preferably greater than 99%, even more preferably greater than 99.5%, may be performed with formula (VII) 4-halo-4'-fluoro butyrophenone (X=I, Br, Cl) in the presence of an acid-binder.

It was surprising to find that if the high-purity formula (II) compound or its salt according to the invention is alkylated, then a lumateperone base is obtained that even if it does have chemical contaminants these contaminants will not contaminate the salt formed.

The separation of the (IV) cis racemate enantiomer pair is therefore preferably carried out without chiral chromatography separation, by resolution in the case of a preferable embodiment of the method according to the invention.

A preferable embodiment of the invention involves that the formula (I) lumateperone or acid addition salts are produced so that the stereoisomers of the formula (IV) cis racemate compound are separated and the formula (II) stereoisomer obtained in this way with stereochemistry 6bR,10aS is alkylated with 4-halo-4'-fluoro butyrophenone (X=I, Br, Cl) to produce the formula (I) lumateperone, or optionally the desired acid addition salt.

Therefore, the method may also be carried out by a.) reacting the formula (IV) compound with one of the enantiomers of a chiral acid, then the salt of the formula (II) compound formed with the chiral acid, in which the configuration of the chiral carbon atoms in the formula of formula (II) compound is 6bR,10aS, is isolated from the reaction mixture and transformed into the formula (II) base, or the method may also involve b.) reacting the formula (IV) compound with the other enantiomer of the above chiral acid, then the salt of the formula (II/A) compound formed with the chiral acid, in which the configuration of the chiral carbon atoms in the formula of the compound is 6bS,10aR, is separated from the reaction mixture, and the formula (II) compound that has been enriched in this way in the reaction mixture, in which the configuration of the chiral carbon atoms in its formula is 6bR,10aS, is isolated. The formula (II) compound obtained in this way, in which the configuration of the chiral carbon atoms in its formula is 6bR,10aS, is transformed into lumateperone.

According to another preferable embodiment of the invention the salt of the formula (II) compound formed with a chiral acid is transformed into a salt with a non-chiral acid, preferable into a salt formed with a mineral acid, preferably into hydrogen halide salt, even more preferably into hydrogen chloride salt, then this is transformed into the formula (II) base and the base obtained in this way is transformed into lumateperone. In other words the production of the lumateperone according to the invention may also be implemented by reacting the salt of the formula (II) base formed with a chiral acid before alkylation with a stronger acid than this chiral acid, preferably with a mineral acid, even more preferably with a hydrogen halide, such as with hydrogen chloride, hydrogen bromide or hydrogen iodide to obtain a salt formed with a mineral acid, which by transforming into a base or by direct alkylation gives lumateperone. Most preferably the salt of the formula (II) base formed with 2 mol hydrochloric acid is used, which is indicated in the present application with the above formula (II)*2HCl.

According to another very preferable embodiment of the invention the formula (V) (+)-dibenzoyl-D-tartaric acid mono(dimethylamide), as chiral acid, is added to the cis racemic stereoisomer mixture of the compound of general formula (IV), then the formula (VI) salt is separated from the solution, which, if required, is transformed directly into a base, or into a salt formed with a mineral acid, preferably into a hydrogen halide salt, even more preferably into hydrogen chloride salt, then this salt is transformed into the formula (II) base, or the process may also involve adding the formula (V/A) (−)-dibenzoyl-D-tartaric acid mono(dimethylamide)

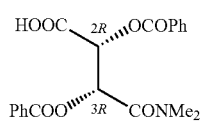
(V/A)

to the formula (IV) stereoisomer mixture solution, isolating the formula (VI/A) compound

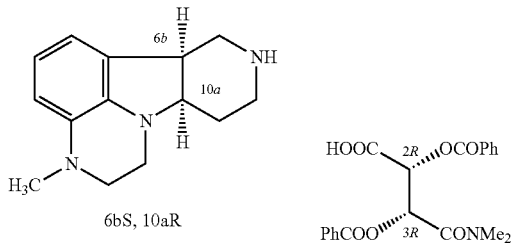
(VI/A)

from the solution, then from the solution enriched in the formula (II) stereoisomer, in which formula (II) the configuration of the chiral carbon atoms is 6bR,10aS, the formula (II) compound is separated in the form of a salt or base, then, if necessary, the separated compound is alkylated to be transformed into a base. In the latter case the formula (II) stereoisomer base precipitated with the concentration of the solution is separated and crystallized if necessary. The process may also involve forming a salt from the mother liquor using a chiral acid, preferably the formula (V) (+)-dibenzoyl-D-tartaric acid mono(dimethylamide), or a non-chiral organic or inorganic acid preferably hydrochloric acid, and the salt is filtered out, and, optionally, the salt is transformed into the formula (II) stereoisomer base. The base obtained in this way is transformed into lumateperone or into its salt.

The formula (IV) cis racemate used as the starting compound may be produced using the method described in international patent application number WO 2000077002 and in the scientific publication *J. Med. Chem.* 2014, 57, 2670-2682.

The production of the formula (V) tartaric acid derivative used to resolve the formula (IV) cis racemate is disclosed in Hungarian patent registration number HU 177094 (date of publication: 28.01.1981). The formula (V/A) tartaric acid derivative may be produced using an analogous process, the latter being commercially available.

In the method according to the invention the chemical purity of the formula (II) and/or (I) compound produced in the course of the method, or of their salts, in which formula (II) or (I) compound the configuration of the chiral carbon atoms is 6bR,10aS, is characteristically greater than 97%, preferably greater than 99%, even more preferably greater than 99.5%.

Consequently, it was surprising to experience that in the course of the resolution of the racemic cis compound of formula (IV), in which the configuration of the chiral carbon atoms is 6bR,10aS, it is formed at great chemical purity, namely in either base or salt form the formula (II) compound obtained with the method according to the invention has a greater chemical purity than 97%, preferably greater than 99%, even more preferably greater than 99.5%. The enantiomer purity of the formula (II) product (or its salt) obtained with the method according to the invention is also greater than 97%, preferably greater than 99%, even more preferably greater than 99.5%.

Following the alkylation of the formula (II) compound, in which the configuration of the chiral carbon atoms is 6bR, 10aS, the formula (I) lumateperone base is transformed into a salt, preferably the p-toluenesulfonic acid salt.

The lumateperone and the salt that can be made from it obtained in the alkylation reaction from the high chemical and enantiomer purity formula (II) product according to our invention also has high chemical purity greater than 97%, preferably greater than 99%, even more preferably greater than 99.5%.

The formula (II) enantiomer cis compound, in which the configuration of the chiral carbon atoms is 6bR,10aS, is used in the alkylation reaction in the form of a base, or the method may also involve the formula (II) compound, in which the configuration of the chiral carbon atoms is 6bR,10aS, being released in the alkylation reaction mixture from the salt form. In other words the chiral salts of the formula (II) compound may be alkylated as follows, including the formula (VI) salt formed with (+)-dibenzoyl-D-tartaric acid mono(dimethylamide), or a non-chiral organic or inorganic acid, preferably hydrochloric acid, (II)·2HCl. Preferably 1.2 to 2 equivalents, preferably 1.5 equivalents of 4-chloro-4'-fluoro butyrophenone or 4-iodo-4'-fluoro butyrophenone with respect to the amount of the formula (II) base are used when implementing the alkylation step. In the case of the use of 4-chloro-4'-fluoro butyrophenone, potassium iodide is also preferably added to the reaction mixture. The alkylation is performed in an aprotic solvent, preferably in acetonitrile or in toluene, preferably in toluene at a temperature between room temperature and the boiling point of the solvent, preferably at the boiling point of the solvent, optionally in the presence of an organic base, preferably a tertiary amine, even more preferably in the presence of triethylamine or N,N-diisopropylethylamine, most preferably triethylamine or an inorganic base, preferably potassium carbonate or caesium carbonate, even more preferably caesium carbonate. The alkylation may also be performed by reacting a mixture of the formula (II) compound and the alkylating agent, optionally in the presence of a liquid base, or using the formula (II) compound as a surplus base it is reacted in a fusing manner. After the reaction has been completed the fusion is cooled, and the lumateperone is extracted in the form of a base or salt. Most preferably the alkylation is performed in toluene, with 4-chloro-4'-fluoro butyrophenone or 4-iodo-4'-fluoro butyrophenone, so that in the case of the use of 4-chloro-4'-fluoro butyrophenone potassium iodide and an organic base are used, preferably triethylamine, or in the case of the use of 4-iodo-4'-fluoro butyrophenone most preferably caesium carbonate is used as the base. Depending on the quality of the base and the halogen used the reaction is performed at a temperature between room temperature and the boiling point of the solvent.

The resolution, i.e. the isolation of the formula (II) compound from the formula (IV) cis racemate is carried out in an organic solvent medium, preferably in a solvent containing an alcohol with 1 to 4 carbon atoms, even more preferably in ethanol (98% or anhydrous), or in methanol, especially preferably in methanol. Preferably methanol, ethanol, 1-propanol, 2-propanol, n-butanol or isobutanol, sec-butanol or tert-butanol, or a mixture of these may be used as the alcohol with 1 to 4 carbon atoms.

Preferably chiral carboxylic acid is used as the resolution agent, even more preferably the formula (V) or (V/A) compounds, and most preferably the formula (V) (+)-dibenzoyl-D-tartaric acid mono(dimethylamide) is used as the resolution agent. An amount of 0.5 to 1 equivalents, preferably 0.7 equivalents of the chiral acid, preferably of the formula (V) or (V/A) compounds are used calculated with respect to the amount of the formula (IV) cis racemate. In the course of the resolution process the temperature of the mixture is maintained at between 0 to 50° C., preferably between 20 to 25° C., most preferably at room temperature.

According to the most preferable embodiment of the invention the lumateperone and/or its salts may be produced so that the formula (IV) cis racemate compound is dissolved in a solvent containing an alcohol with 1 to 4 carbon atoms, preferably in ethanol, more preferably in ethanol (98% or anhydrous), or in methanol, especially preferably in methanol. An amount of 0.5 to 1 equivalents, preferably 0.7 equivalents of the formula (V) (+)-dibenzoyl-D-tartaric acid mono(dimethylamide) calculated with respect to the amount of the formula (IV) cis racemate is added to the solution at a temperature of between 0 to 50° C., preferably between 20 to 25° C., most preferably at room temperature, then the formed formula (VI) salt is separated, then a.)

a.1.) the formula (II) base is released from the formula (VI) salt obtained and optionally crystallized, or a.2.) by stirring the obtained formula (VI) salt in an organic solvent, preferably ethyl acetate it is transformed into the formula (II)·2HCl salt with hydrochloric acid, preferably with hydrochloric acid dissolved in an organic solvent, even more preferably with hydrochloric acid dissolved in esters of 1 to 4 carbon atom carboxylic acids formed with 1 to 4 carbon atom alcohols, even more preferably with hydrochloric acid dissolved in ethyl acetate, ethanol or 2-propanol, then the formula (II) compound is released from the salt with a base, following this the base (II) produced according to point a.1.) or a.2.), the formula (VI) salt or the (II)·2HCl salt is alkylated in an organic solvent, preferably in an organic aprotic solvent, preferably in acetonitrile or toluene, most preferably in toluene, preferably at a temperature between room temperature and the boiling point of the solvent, preferably with 1.2 to 2 equivalents, more preferably 1.5 equivalents of 4-halo-4'-fluoro butyrophenone, preferably 4-chloro-4'-fluoro butyrophenone or 4-iodo-4'-fluoro butyrophenone, most preferably 4-chloro-4'-fluoro butyrophenone in the presence of potassium iodide, furthermore in the presence of an organic acid-binder, preferably a tertiary amine, more preferably triethylamine or N,N-diisopropylethylamine, even more preferably triethylamine, or in the presence of an inorganic acid-binder, preferably potassium carbonate or caesium carbonate, most preferably in the presence of caesium carbonate.

The reaction may also be carried out so that the formula (VI) salt is suspended in an organic solvent, then while intensively stirring a solution of hydrogen chloride gas in an organic solvent is added to it in excess and the new salt that is produced is filtered out. Ethyl acetate is preferably used as the solvent. The hydrochloric acid excess is preferably 2.5 equivalents. The formula (II)·2HCl compound obtained in this way is transformed into the formula (I) lumateperone, or optionally its acid addition salt by alkylating with the formula (VII) 4-halo-4'-fluoro butyrophenone under the conditions disclosed in the case of the alkylation of the formula (VI) compound.

An important part of the invention is formed by the high-purity intermediates, which make it possible to produce high-purity lumateperone base or salts.

From a practical point of view it is very preferable if the formula (VI) salt is transformed into the formula (II) compound. In the course of the method an aqueous solution of an inorganic base, preferably sodium hydroxide is added to the aqueous suspension of the formula (VI) salt, then the mixture is extracted with an organic solvent, preferably toluene or ethyl acetate. The crystalline formula (II) compound is obtained by first drying then evaporating the latter solutions. The precipitated crystals are, if required, recrystallized from an ether-type solvent, preferably diisopropyl ether.

The formula (II) compound obtained in this way is transformed into the formula (I) lumateperone, or optionally into its acid addition salt by alkylating with the formula (VII) 4-halo-4'-fluoro butyrophenone under the conditions disclosed in the case of the alkylation of the formula (VI) compound.

The object of the invention relates to the crystalline form of the formula (II) (6bR,10aS)-3-methyl-2,3,6b,9,10,10a-hexahydro-1H-pyrido[3',4': 4,5]pyrrolo[1,2,3-de]quinoxaline base. The synthesis of the formula (II) compound was disclosed in the international patent application number WO 2008112280. In the synthesis presented there the base (II) was produced from a derivative protected by an ethoxycarbonyl group. However, after the removal of the N-ethoxycarbonyl group, a dark brown oil was obtained that is obviously unsuited for conventional purification processes, which, according to HPLC tests only contained 88.1% of the formula (II) final intermediate. As this intermediate is sensitive, and in this way unsuited for purification at industrial scales, the production of lumateperone is only possible from an intermediate that contains a large amount of chemical contaminants, which led to a very contaminated final product.

It was surprising to find that if the formula (II) base is produced by resolution from the racemic base disclosed in publication specification number WO 2000077002, a pure base is obtained in the course of the resolution process that may be crystallized and purified by recrystallization if necessary. The novel crystalline form is easy to handle. On the basis of the documents according to the state of the art it could not be expected that this intermediate would be crystalline. More specifically it was found that the formula (II) compound is morphologically uniform. The positions of the x-ray powder diffraction lines characteristic of the formula (II) crystalline compound according to the invention are [°2θ(±0.2 °2θ)]: 9.99; 16.03; 20.87.

It may also be characterised with the following x-ray powder diffraction lines: [°2θ(±0.2 °2θ)]: 9.99; 13.17; 15.25; 16.03; 20.32, 20.87, or with the following x-ray powder diffraction lines as well:

[°2θ(±0.2 °2θ)]: 7.46; 9.99; 13.17; 15.25; 16.03; 16.38; 20.32; 20.87; 21.35; 23.18.

The formula (II) crystalline compound according to the invention may also be characterised with the diffraction signals contained in the following table (2/A):

TABLE 2/A

| Line number: | Position [° 2θ] | d-value [Å] | Relative intensity [%] |
|---|---|---|---|
| 1 | 7.46 | 11.84 | 8 |
| 2 | 9.99 | 8.85 | 28 |
| 3 | 11.38 | 7.77 | 3 |
| 4 | 11.70 | 7.56 | 8 |
| 5 | 13.17 | 6.72 | 77 |
| 6 | 13.28 | 6.66 | 74 |
| 7 | 13.46 | 6.57 | 4 |
| 8 | 14.96 | 5.92 | 3 |
| 9 | 15.25 | 5.81 | 61 |
| 10 | 16.03 | 5.52 | 100 |
| 11 | 16.38 | 5.41 | 64 |
| 12 | 16.70 | 5.30 | 15 |
| 13 | 17.36 | 5.10 | 10 |
| 14 | 17.52 | 5.06 | 32 |
| 15 | 17.74 | 5.00 | 17 |
| 16 | 20.07 | 4.42 | 13 |
| 17 | 20.32 | 4.37 | 56 |
| 18 | 20.87 | 4.25 | 38 |
| 19 | 21.35 | 4.16 | 27 |
| 20 | 21.94 | 4.05 | 2 |
| 21 | 22.17 | 4.01 | 20 |
| 22 | 22.34 | 3.98 | 27 |
| 23 | 23.18 | 3.83 | 52 |
| 24 | 23.53 | 3.78 | 18 |
| 25 | 23.85 | 3.73 | 1 |
| 26 | 24.49 | 3.63 | 6 |
| 27 | 25.07 | 3.55 | 3 |
| 28 | 25.27 | 3.52 | 28 |
| 29 | 25.73 | 3.46 | 4 |
| 30 | 25.93 | 3.43 | 10 |
| 31 | 26.24 | 3.39 | 3 |
| 32 | 26.55 | 3.35 | 5 |
| 33 | 27.25 | 3.27 | 4 |
| 34 | 27.82 | 3.20 | 2 |
| 35 | 28.07 | 3.18 | 9 |
| 36 | 28.94 | 3.08 | 3 |
| 37 | 29.37 | 3.04 | 12 |
| 38 | 29.84 | 2.99 | 4 |
| 39 | 30.19 | 2.96 | 5 |
| 40 | 30.43 | 2.94 | 2 |
| 41 | 30.94 | 2.89 | 4 |
| 42 | 31.23 | 2.86 | 3 |
| 43 | 31.65 | 2.82 | 1 |
| 44 | 32.10 | 2.79 | 1 |
| 45 | 33.1 | 2.70 | 13 |
| 46 | 33.58 | 2.67 | 2 |
| 47 | 33.8 | 2.65 | 2 |
| 48 | 34.45 | 2.60 | 5 |

The formula (II) crystalline compound according to the invention may also be characterised with the x-ray powder diffraction image shown in FIG. 1.

The object of the invention also relates to the production of the crystalline form of the formula (II) (6bR,10aS)-3-methyl-2,3,6b,9,10,10a-hexahydro-1H-pyrido[3',4': 4,5]pyrrolo[1,2,3-de]quinoxaline base. This may be also be performed so that a.) the formula (VI) salt formed with (+)-dibenzoyl-D-tartaric acid mono(dimethylamide), or the salt with formula (II)·2HCl formed using hydrochloric acid is reacted with a base and the released formula (II) compound is brought into crystalline form, or b.) the formula (IV) compound is reacted with a chiral acid, preferably the formula (V) (+)-dibenzoyl-D-tartaric acid mono(dimethylamide), then the salt of compound (II) formed with chiral acid, in which the configuration of the chiral carbon atoms is 6bR,10aS, is isolated from the reaction mixture and transformed into the formula (II) base, or c.) the formula (IV) compound is reacted with a chiral acid, then the salt of the compound (II/A),

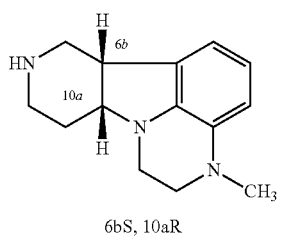

(II/A)

6bS, 10aR in which the configuration of the chiral carbon atoms is 6bR,10aS, formed with a chiral acid is separated from the reaction mixture, and then the formula (II) compound enriched in this way in the reaction mixture, in which the configuration of the chiral carbon atoms is 6bR,10aS, is isolated, then the formula (II) compound obtained in this way is crystalized.

In the above b.) and c.) processes the compounds (V) or (V/A) are reacted as chiral acids with the cis racemic compound (IV), in other words preferably the formula (IV) compound is reacted with (+)-dibenzoyl-D-tartaric acid mono(dimethylamide), then the compound (VI) obtained, in which compound (VI) the configuration of the chiral carbon atoms is 6bR,10aS, is separated from the reaction mixture and then transformed into the formula (II) base, or the formula (IV) compound is reacted with the formula (V/A) compound, then the formula (II/A) compound, in which compound the configuration of the chiral carbon atoms is 6bS,10aR, is separated from the reaction mixture, and the formula (II) compound enriched in the reaction mixture in this way, in which compound the configuration of the chiral carbon atoms is 6bR,10aS, is isolated. The process may also involve dissolving the formula (IV) compound in a solvent containing an alcohol with 1 to 4 carbon atoms, preferably in an alcohol with 1 to 4 carbon atoms, more preferably in ethanol or methanol, even more preferably in 96v/v % or anhydrous ethanol or methanol, most preferably in methanol. The solution obtained is maintained at a temperature of between 0 and 50° C., preferably between 20 to 25° C., most preferably at room temperature, and 0.5 to 1 equivalents, preferably 0.7 equivalents of formula (V) (+)-dibenzoyl-D-tartaric acid mono(dimethylamide) calculated with respect to the amount of formula (IV) cis racemate is added to the solution, then the formed formula (VI) salt is separated, and then the formula (II) base is released from the formula (VI) salt obtained and optionally crystallised, or the formula (VI) salt is stirred in an organic solvent, preferably ethyl acetate with hydrochloric acid dissolved in an organic solvent, preferably ethyl acetate, transformed to the formula (II) ·2HCl salt, then the formula (II) compound is released from the salt with a base.

The formula (II) base may be isolated in crystalline form from an aprotic solvent, preferably from an aromatic, ester or ether type solvent. Preferably toluene is used as the aromatic solvent, preferably ethyl acetate is used as the ester type solvent and aliphatic ethers, preferably diisopropyl ether is used as the ether type solvent.

The crystallization may also be carried out by evaporating a solution of the formula (II) compound formed with ethyl acetate or toluene, preferably an anhydrous solution. If required the precipitated crystals may be recrystallized from an ether type solvent, preferably diisopropyl ether.

In other words a very preferable embodiment of the invention may involve transforming the formula (VI) salt into the formula (II) compound. In the course of the method an aqueous solution of an inorganic base, preferably of sodium hydroxide is added to the aqueous suspension of the formula (VI) salt, then the mixture is extracted using an organic solvent, preferably toluene or ethyl acetate. The crystalline formula (II) compound is obtained by drying then evaporating these latter solutions. The crystalline form of the formula (II) compound is novel.

The object of the invention also relates to the formula (II)·2HCl salt

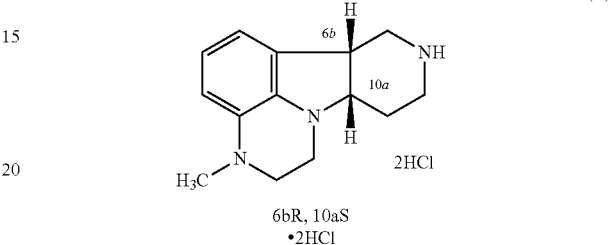

(II)

6bR, 10aS
·2HCl of the formula (II) (6bR,10aS)-3-methyl-2,3,6b,9,10,10a-hexahydro-1H-pyrido[3',4': 4,5]pyrrolo[1,2,3-de]quinoxaline formed with hydrochloric acid. This salt may be separated from the solution of the formula (II) cis enantiomer base or from the reaction of the formula (VI) salt with hydrochloric acid with a very high chemical and enantiomer purity level. It can also be prepared by turning the compound of the formula (II) into salt with hydrochloric acid. In the resolution process according to the invention the chemical purity of this salt is greater than 97%, preferably greater than 99%, and even more preferably greater than 99.5%, furthermore its enantiomer purity is also greater than 97%, preferably greater than 99%, and even more preferably greater than 99.5%.

The formula (II)·2HCl compound according to the invention is crystalline. The positions of the x-ray powder diffraction lines characteristic of the formula (II)·2HCl crystalline compound according to the invention are [°2θ(±0.2 °2θ)]: 13.43; 16.52; 22.19.

It may also be characterised with the following x-ray powder diffraction lines: °2θ(±0.2 °2θ)]: 6.75; 13.43; 16.52; 17.79; 20.26; 22.19, or with the following x-ray powder diffraction lines as well: [°2θ(±0.2 °2θ)]: 6.75; 9.40; 13.43; 16.52; 17.79; 18.20; 18.86; 20.26; 22.19; 27.02.

The formula (II)·2HCl crystalline compound according to the invention may also be characterised with the diffraction signals contained in the following table (2/B):

TABLE 2/B

| Line number: | Position [°2θ] | d-value [Å] | Relative intensity [%] |
|---|---|---|---|
| 1 | 6.75 | 13.08 | 13 |
| 2 | 9.4 | 9.4 | 9 |
| 3 | 11.07 | 7.99 | 7 |
| 4 | 13.43 | 6.59 | 68 |
| 5 | 15.46 | 5.73 | 3 |
| 6 | 16.19 | 5.47 | 13 |
| 7 | 16.52 | 5.36 | 100 |
| 8 | 17.79 | 4.98 | 42 |
| 9 | 18.2 | 4.87 | 8 |
| 10 | 18.86 | 4.7 | 14 |
| 11 | 20.26 | 4.38 | 67 |

TABLE 2/B-continued

| Line number: | Position [°2θ] | d-value [Å] | Relative intensity [%] |
|---|---|---|---|
| 12 | 22.19 | 4 | 84 |
| 13 | 22.79 | 3.9 | 4 |
| 14 | 23.27 | 3.82 | 2 |
| 15 | 23.5 | 3.78 | 11 |
| 16 | 24.26 | 3.67 | 5 |
| 17 | 24.44 | 3.64 | 9 |
| 18 | 25.45 | 3.5 | 7 |
| 19 | 27.02 | 3.3 | 22 |
| 20 | 27.41 | 3.25 | 9 |
| 21 | 28.52 | 3.13 | 4 |
| 22 | 28.95 | 3.08 | 12 |
| 23 | 29.78 | 3 | 9 |
| 24 | 30.61 | 2.92 | 12 |
| 25 | 30.86 | 2.89 | 15 |
| 26 | 31.15 | 2.87 | 35 |
| 27 | 31.73 | 2.82 | 14 |
| 28 | 32.66 | 2.74 | 4 |
| 29 | 33.42 | 2.68 | 10 |
| 30 | 34.39 | 2.61 | 4 |

The formula (II) crystalline compound according to the invention may also be characterised with the x-ray powder diffraction image shown in FIG. 6.

The object of the invention also relates to the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide). This salt is formed in the course of the very preferable production of the formula (II) compound in the case of resolution the formula (IV) cis racemic compound. This salt can be isolated at a very high level of chemical and enantiomer purity. The chemical purity of the formula (VI) salt that may be isolated in the resolution process according to the invention is greater than 97%, preferably greater than 99% and even more preferably greater than 99.5%, furthermore its enantiomer purity is greater than 97%, preferably greater than 99% and even more preferably greater than 99.5%.

According to a preferably embodiment of the invention, the salt is preferably solid, more preferably crystalline, even more preferably morphologically uniform.

The positions of the x-ray powder diffraction lines characteristic of the formula (VI) crystalline compound according to the invention are °2θ(±0.2 °2θ)]: 6.17; 19.88; 23.58.

It may be also characterised with the following x-ray powder diffraction lines: [°2θ(±0.2 °2θ)]: 6.17; 9.89; 13.56; 18.66; 19.88; 23.58, or with the following x-ray powder diffraction lines as well: [°2θ(±0.2 °2θ)]: 6.17; 9.89; 10.37; 11.72; 12.94; 13.56; 14.92; 18.66; 19.88; 23.58.

Furthermore, the formula (VI) crystalline compound according to the invention may also be characterised with the diffraction signals contained in the following table:

TABLE 3

| Line number: | Position [°2θ] | d-value [Å] | Relative intensity [%] |
|---|---|---|---|
| 1 | 6.17 | 14.32 | 58 |
| 2 | 9.89 | 8.93 | 63 |
| 3 | 10.37 | 8.53 | 31 |
| 4 | 10.68 | 8.28 | 5 |
| 5 | 11.72 | 7.54 | 15 |
| 6 | 12.35 | 7.16 | 5 |
| 7 | 12.94 | 6.83 | 49 |

TABLE 3-continued

| Line number: | Position [°2θ] | d-value [Å] | Relative intensity [%] |
|---|---|---|---|
| 8 | 13.56 | 6.53 | 61 |
| 9 | 14.31 | 6.18 | 6 |
| 10 | 14.92 | 5.93 | 18 |
| 11 | 15.40 | 5.75 | 6 |
| 12 | 16.56 | 5.35 | 33 |
| 13 | 16.71 | 5.30 | 17 |
| 14 | 17.18 | 5.16 | 15 |
| 15 | 17.54 | 5.05 | 42 |
| 16 | 17.82 | 4.97 | 21 |
| 17 | 18.66 | 4.75 | 46 |
| 18 | 19.12 | 4.64 | 20 |
| 19 | 19.46 | 4.56 | 14 |
| 20 | 19.88 | 4.46 | 100 |
| 21 | 20.82 | 4.26 | 17 |
| 22 | 21.47 | 4.14 | 20 |
| 23 | 22.07 | 4.02 | 8 |
| 24 | 22.58 | 3.93 | 5 |
| 25 | 22.80 | 3.90 | 6 |
| 26 | 23.06 | 3.85 | 19 |
| 27 | 23.58 | 3.77 | 85 |
| 28 | 24.06 | 3.70 | 21 |
| 29 | 24.9 | 3.57 | 5 |
| 30 | 25.10 | 3.55 | 16 |
| 31 | 25.60 | 3.48 | 8 |
| 32 | 25.97 | 3.43 | 14 |
| 33 | 26.29 | 3.39 | 14 |
| 34 | 26.57 | 3.35 | 8 |
| 35 | 27.11 | 3.29 | 14 |
| 36 | 27.29 | 3.26 | 17 |
| 37 | 28.15 | 3.17 | 12 |
| 38 | 28.87 | 3.09 | 2 |
| 39 | 29.08 | 3.07 | 1 |
| 40 | 30.13 | 2.96 | 19 |
| 41 | 30.35 | 2.94 | 3 |
| 42 | 30.65 | 2.91 | 6 |
| 43 | 31.21 | 2.86 | 12 |
| 44 | 31.74 | 2.82 | 2 |
| 45 | 31.89 | 2.80 | 2 |
| 46 | 32.22 | 2.78 | 2 |
| 47 | 32.82 | 2.73 | 3 |
| 48 | 33.5 | 2.67 | 6 |
| 49 | 33.81 | 2.65 | 2 |
| 50 | 34.45 | 2.60 | 4 |

The formula (VI) crystalline compound according to the invention may also be characterised with the x-ray powder diffraction image shown in FIG. 2.

The object of the invention also relates to the synthesis of the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide). This compound may be produced in such a way that a.) the formula (IV) compound is reacted with the formula (V) (+)-dibenzoyl-D-tartaric acid mono(dimethylamide), then the formula (VI) compound obtained in this way is separated from the reaction mixture, or b.) the formula (IV) compound is reacted with a chiral acid, preferably the formula (V/A) (−)-dibenzoyl-L-tartaric acid mono(dimethylamide), then the salt of compound (II/A) formed with a chiral acid, in which the configuration of the chiral carbon atoms is 6bS, 10aR, preferably the formula (VI/A) salt formed with (−)-dibenzoyl-L-tartaric acid mono(dimethylamide) is isolated from the reaction mixture. The formula (II) compound enriched in the reaction mixture in this way is reacted with the formula (V) (+)-dibenzoyl-D-tartaric acid mono(dimethylamide), then the formula (VI) compound formed is isolated.

In other words, the production of the formula (VI) compound may be preferably performed in such a way that the formula (IV) cis racemic compound is dissolved in a solvent containing an alcohol with 1 to 4 carbon atoms, preferably in an alcohol with 1 to 4 carbon atoms, more preferably in ethanol, even more preferably in 96% or anhydrous ethanol, or in methanol, most preferably in methanol, then the solution is maintained at a temperature of between 0 and 50° C., preferably between 20 to 25° C., most preferably at room temperature, and then reacted with 0.5 to 1 equivalents, preferably 0.7 equivalents of formula (V) (+)-dibenzoyl-D-tartaric acid mono(dimethylamide) calculated with respect to the amount of formula (IV) cis racemate.

The object of the invention also relates to a method for the production of the formula (II)·2HCl salt of formula (II) (6bR,10aS)-3-methyl-2,3,6b,9,10,10a-hexahydro-1H-pyrido[3',4': 4,5]pyrrolo[1,2,3-de]quinoxaline formed with hydrochloric acid, characterised by that the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide), or the formula (II) base is stirred in an organic solvent, preferably ethyl acetate, then hydrochloric acid, preferably hydrochloric acid dissolved in an organic solvent, more preferably hydrochloric acid dissolved in esters of 1 to 4 carbon atom carboxylic acids formed with 1 to 4 carbon atom alcohols or in 1 to 4 carbon atom alcohols, even more preferably hydrochloric acid gas dissolved in ethyl acetate, ethanol or 2-propanol is added to the reaction mixture, then the formula (II)·2HCl salt is separated.

The formula (II)·2HCl salt may also be produced by adding hydrogen chloride gas dissolved in an organic solvent to the solution of the formula (II) compound. Most preferably the formula (II) base is stirred in ethyl acetate, then hydrogen chloride gas dissolved in ethyl acetate is added to the mixture, then the (II)·2HCl salt that is formed is isolated.

The object of the invention also relates to the use of the crystalline form of formula (II) (6bR,10aS)-3-methyl-2,3, 6b,9,10,10a-hexahydro-1H-pyrido[3',4': 4,5]pyrrolo[1,2,3-de]quinoxaline, of the formula (VI) (+)-dibenzoyl-D-tartaric acid mono(dimethylamide) salt, or of the formula (II)·2HCl hydrogen chloride salt for the production of lumateperone or of its salts, preferably for the production of the formula (III) lumateperone amorphous or crystalline salt, in which the molar ratio of lumateperone to p-toluenesulfonic acid is 1:1, the formula (IX) salt, in which the molar ratio of lumateperone to p-toluenesulfonic acid is 1:2, or the salt of lumateperone and naphthalene-2-sulfonic acid, preferably for the production of the formula (X) salt, in which the molar ratio of lumateperone to naphthalene-2-sulfonic acid is 1:1, even more preferably for the production of the formula (VIII) salt, in which the molar ratio of lumateperone to naphthalene-2-sulfonic acid is 1:2.

Use and application are synonyms in the context of the present invention.

Furthermore, the object of the invention relates to lumateperone or its salt, preferably the salt of lumateperone formed with p-toluenesulfonic acid, preferably the formula (III) amorphous salt, in which the molar ratio of lumateperone to p-toluenesulfonic acid is 1:1, or the formula (IX) salt of lumateperone formed with p-toluenesulfonic acid, in which the molar ratio of lumateperone to p-toluenesulfonic acid is 1:2, or the salt of lumateperone formed with naphthalene-2-sulfonic acid, preferably the formula (X) salt, in which the molar ratio of lumateperone to naphthalene-2-sulfonic acid is 1:1, even more preferably the formula (VIII) salt, in which the molar ratio of lumateperone to naphthalene-2-sulfonic acid is 1:2, most preferably the formula (III) amorphous salt, in which the molar ratio of lumateperone to p-toluenesulfonic acid is 1:1, and the formula (VIII) salt, in which the molar ratio of lumateperone to naphthalene-2-sulfonic acid is 1:2, the chemical purity of which is greater than 97%, preferably greater than 99%, even more preferably greater than 99.5%.

Furthermore, the object of the invention relates to the lumateperone or its salt produced using one of the methods described in the present application. Furthermore, the object of the invention relates to its formula (III) amorphous salt, in which the molar ratio of lumateperone to p-toluenesulfonic acid is 1:1, or the formula (IX) salt of lumateperone formed with p-toluenesulfonic, in which the molar ratio of lumateperone to p-toluenesulfonic acid is 1:2, or the salt of lumateperone and naphthalene-2-sulfonic acid, preferably the formula (X) salt, in which the molar ratio of lumateperone to naphthalene-2-sulfonic acid is 1:1, even more preferably the formula (VIII) salt, in which the molar ratio of lumateperone to naphthalene-2-sulfonic acid is 1:2. One of the most preferable embodiments of the invention is the formula (III) amorphous salt, in which the molar ratio of lumateperone to p-toluenesulfonic acid is 1:1, and the formula (VIII) salt, in which the molar ratio of lumateperone to naphthalene-2-sulfonic acid is 1:2, and the enantiomer purity of which is greater than 97%, preferably greater than 99%, even more preferably greater than 99.5%.

One of the most preferable embodiments of the invention is the formula (III) amorphous salt of lumateperone formed with p-toluenesulfonic acid. Preferably the chemical purity of the amorphous formula (III) salt according to the invention is greater than 97%, preferably greater than 99%, even more preferably greater than 99.5%, and/or its enantiomer purity is greater than 97%, preferably greater than 99%, even more preferably greater than 99.5%.

According to an especially preferable embodiment of the invention the amorphous salt of lumateperone according to the invention formed with p-toluenesulfonic acid is morphologically uniform.

Another especially preferable embodiment of the invention is the lumateperone and p-toluenesulfonic acid formula (III) morphologically uniform amorphous salt, the x-ray powder diffractogram of which corresponds to FIG. 5. An amorphous material is deemed to be morphologically uniform according to the present invention if a maximum of 5% of its mass, preferably a maximum of 3% of its mass, more preferably up to 1% of its mass, most preferably 0.5% of its mass comprises crystalline product.

The object of the invention also relates to the production of the above amorphous formula (III) salt. The production of the amorphous formula (III) salt is most preferably carried out by reacting the lumateperone base or its salt formed with a carboxylic acid with p-toluenesulfonic acid, then, if necessary the salt obtained is transformed into amorphous form. The process may also involve precipitating the salt from the reaction mixture in amorphous form. Most preferably the process involves reacting either the lumateperone base or its salt formed with a carboxylic acid with p-toluenesulfonic acid, in such a way that the molar ratio is adjusted in order to provide a sufficient excess of p-toluenesulfonic acid. The production of the formula (VIII) salt most preferably involves reacting the lumateperone base or its salt formed with a carboxylic acid with naphthalene-2-sulfonic acid. In the case of the production of the mono-tosylate salt 0.7 to 1.2 mol equivalents, most preferably 1 equivalent of p-toluenesulfonic acid, preferably p-toluenesulfonic acid hydrate is added to a solution of formula (I) lumateperone base, preferably to a 2-propanol solution at room temperature and the salt formed is filtered, optionally washed and dried.

The production of the morphologically uniform p-toluenesulfonic acid salt (III) of the formula (I) lumateperone is preferably performed so that the formula (I) lumateperone base is reacted with an amount of p-toluenesulfonic acid equal to 0.7 to 1.2 times the molar amount of the formula (I) lumateperone base, preferably 0.9 to 1.1 times the amount, more preferably 0.95 to 1.05 times the amount, most preferably with an equivalent amount of p-toluenesulfonic acid. According to a very preferable embodiment of the invention the formula (I) lumateperone base is dissolved in an organic solvent, then the p-toluenesulfonic acid is added, then the salt obtained is separated, then washed and dried if necessary. The process may also involve adding p-toluenesulfonic acid dissolved in an organic solvent to a solution of lumateperone base, then if necessary the precipitated product is stirred, then filtered, washed and dried. Dipolar aprotic solvents are used as the organic solvent, preferably nitriles, acetonitrile as the nitrile type solvent. In the course of salt production the mixture is maintained at a temperature of from 0 to 50° C., preferably a 20 to 25° C., most preferably at room temperature. In the course of the method the formula (III) lumateperone p-toluenesulfonic acid salt forming in the reaction mixture, in which salt the molar ratio of formula (I) lumateperone and p-toluenesulfonic acid is 1:1, is stirred before filtering for 2 to 48 hours, preferably for 12 to 36 hours, even more preferably for 18 to 26 hours at room temperature.

One of the most preferable embodiments of the invention involves adding the formula (I) lumateperone base to acetonitrile, water is added to this, then 0.7 to 1.2 times of p-toluenesulfonic acid with respect to the molar amount of the formula (I) lumateperone base, preferably 0.9 to 1.1 times the amount, more preferably 0.95 to 1.05 times the amount, most preferably an equivalent amount of p-toluenesulfonic acid is added to it, and the solution obtained is lyophilised.

The process may also include that the lumateperone p-toluenesulfonic acid salt is produced, in which salt the molar ratio of the formula (I) lumateperone and p-toluenesulfonic acid is 1:1, and which, optionally, is in a morphologically uniform or mixed crystalline form, or the crystalline and amorphous salt mixture is dissolved in a mixture of water and a nitrile type solvent, preferably acetonitrile, then the solution is lyophilised. The volumetric ratio of the water and the nitrile type solvent, preferably acetonitrile at room temperature (20° C.) is 40:1 to 10:1, even more preferably 30:1 to 15:1, most preferably 25:1 to 19:1. The ratio of the tosylate salt with respect to the volume of the solution (tosylate salt mass[g]/solution volume [litre]) is preferably 0.2 to 100, more preferably 0.2 to 50, even more preferably 0.25 to 10, most preferably 0.3 to 1.

The amorphous salt of lumateperone formed with p-toluenesulfonic acid may also be produced by reacting the formula (I) lumateperone base with 0.7 to 1.2 times the molar amount of p-toluenesulfonic acid with respect to the formula (I) lumateperone base, preferably 0.9 to 1.1 times the amount, more preferably 0.95 to 1.05 times the amount, most preferably with an equivalent amount of p-toluenesulfonic acid, then the salt obtained a.) is separated in amorphous form, or b.) the formula (III) lumateperone p-toluenesulfonic acid salt, which consists of morphologically uniform crystals, or consists of several crystals of different morphology, or of a mixture of crystalline and amorphous tosylate salts of various morphology, is isolated, then dissolved in a mixture of water and a nitrile type solvent, preferably in a mixture of acetonitrile and water and then lyophilised.

In method a.) the salt formation is preferably performed in a solvent mixture of water and a nitrile type solvent, preferably in a solvent mixture containing water and acetonitrile, then the formula (III) lumateperone p-toluenesulfonic acid salt obtained in this way is lyophilised.

The volumetric ratio of the water and the nitrile type solvent in the solvent mixture to be lyophilised, preferably of water and acetonitrile at room temperature (20° C.) is preferably 40:1 to 10:1, even more preferably 30:1 to 15:1, most preferably 25:1 to 19:1.

The ratio of the mass of the tosylate salt with respect to the volume of the solvent (tosylate salt mass [g]/solvent volume [litre]) is preferably 0.2 to 100, more preferably 0.2 to 50, even more preferably 0.25 to 10, most preferably 0.3 to 1. Most preferably the process may involve performing the salt formation a.) in a mixture of water and a nitrile type solvent, preferably in a mixture of water and acetonitrile, then the solution formed is lyophilised, or b.) the lumateperone base is dissolved in acetonitrile and an aqueous solution of p-toluenesulfonic acid is added to it and the solution obtained is lyophilised, or c.) the lumateperone base is dissolved in a nitrile type solvent, preferably in acetonitrile, then salt is formed with a solution of p-toluenesulfonic acid in a nitrile type solvent, preferably in acetonitrile, water is then added to the mixture containing the salt, then the clear solution obtained in this way is lyophilised, or d.) the lumateperone base is stirred in water, or in a nitrile type solvent, preferably in acetonitrile, or in a mixture of a nitrile type solvent, preferably acetonitrile and water and p-toluenesulfonic acid or a solution of p-toluenesulfonic acid formed with a nitrile type solvent, preferably acetonitrile is added to the mixture, and optionally further nitrile type solvent, preferably acetonitrile is added to the mixture, which is then lyophilised. In the course of salt formation the temperature of the mixture is maintained at between 0 to 50° C., preferably between 20 to 25° C., most preferably at room temperature.

The lyophilising may be performed with any commercially available device suitable for the lyophilising of solutions. A person skilled in the art may select from among these on the basis of the specifications of the devices and on the basis of the general knowledge of the person skilled in the art. For example, a preferable device is the ZIRBUS VaCo 2-II-E lyophilising device, which is connected to a VACUUMBRAND 6GMBH+COKg VSP 3000 motor.

In other words the lyophilising operation may be preferably performed by cooling the solution of lumateperone monotosylate in water and acetonitrile to the extent so that the water freezes. The mixture, therefore, is cooled to a temperature lower than 0° C., preferably to between 0° C. and −200° C., even more preferably to between −60° C. and −200° C., most preferably to a temperature between −70° C. and −100° C. The cooling may be performed, for example, with the use of liquid nitrogen, liquid air, or, for example, dry ice or even dry ice and acetone may be preferably used. The vessel containing the frozen solution is subjected to a vacuum in the lyophilising device for the purpose of evaporating the ice. The pressure used is preferably lower than 6.117 mbar, preferably 0.01 to 6 mbar, even more preferably 0.1 to 5 mbar, most preferably 1 to 5 mbar.

Most preferably the lumateperone monotosylate is dissolved in the solvent mixture to be lyophilised, which is a mixture of water and a nitrile type solvent, preferably a mixture of water and acetonitrile, and in which the volumetric ratio of the water and nitrile type solvent at room temperature (20° C.) is 40:1-10:1, more preferably 30:1-15:1, most preferably 25:1-19:1. The ratio of the dissolved tosylate salt with respect to the volume of the solution (tosylate salt mass[g]/solution volume [litre]) is preferably 0.2 to 100, more preferably 0.2 to 50, even more preferably 0.25 to 10, most preferably 0.3 to 1. The complete dissolving takes place slowly, over the course of 1 to 2 hours at room temperature. The solution obtained in this way is lyophilised under the above conditions.

For example, the process may involve dissolving 80 mg lumateperone monotosylate in a mixture of 250 ml water and 12.5 ml acetonitrile. The complete dissolving takes place slowly, over the course of 1 to 2 hours at room temperature. The solution obtained is divided equally between two 500 ml round-bottomed flasks and the content of the flasks is frozen in an acetone dry ice bath. Following this the two flasks are connected to a ZIRBUS VaCo 2-II-E lyophilising device, to which a VACUUMBRAND 6GMBH+COKg VSP 3000 motor is connected and the lyophilising is performed at −80° C., at a pressure of 3.6 mbar to constant weight.

The chemical and/or enantiomer purity of the formula (III) amorphous monotosylate produced with the above processes is greater than 97%, preferably greater than 99%, even more preferably greater than 99.5%.

Another preferable embodiment of the invention is the salt of lumateperone formed with naphthalene-2-sulfonic acid, preferably the formula (X) salt, in which the molar ratio of lumateperone to naphthalene-2-sulfonic acid is 1:1. According to a very preferable embodiment of the invention the salt of lumateperone formed with naphthalene-2-sulfonic acid is crystalline. The chemical purity of the salt of lumateperone formed with naphthalene-2-sulfonic acid according to the invention is greater than 97%, preferably greater than 99%, even more preferably greater than 99.5%, and/or its enantiomer purity is greater than 97%, preferably greater than 99%, even more preferably greater than 99.5%.

Another preferable embodiment of the invention is the salt of lumateperone formed with naphthalene-2-sulfonic acid, preferably the formula (VIII) salt, in which the molar ratio of lumateperone to naphthalene-2-sulfonic acid is 1:2. According to a very preferable embodiment of the invention the salt of lumateperone formed with naphthalene-2-sulfonic acid is crystalline.

The chemical purity of the salt of lumateperone formed with naphthalene-2-sulfonic acid according to the invention is greater than 97%, preferably greater than 99%, even more preferably greater than 99.5%, and/or its enantiomer purity is greater than 97%, preferably greater than 99%, even more preferably greater than 99.5%.

According to a very preferable embodiment of the invention the salt of lumateperone formed with naphthalene-2-sulfonic acid is morphologically uniform.

An especially preferable embodiment of the invention is the formula (VIII) salt of lumateperone formed with naphthalene-2-sulfonic acid, which is morphologically uniform and the positions of the characteristic x-ray powder diffraction peaks are [°2θ(±0.2 °2θ)]: 3.87; 15.09; 20.71, preferably [°2θ(±0.2 °2θ)]: 3.87; 5.82; 15.09; 17.38; 20.71; 27.20, even more preferably [°2θ(±0.2 °2θ)]: 3.87; 5.82; 7.76; 13.63; 15.09; 15.57; 17.38; 18.52; 20.26; 20.71; 21.04; 27.20.

An especially preferable embodiment of the invention is the formula (VIII) salt of lumateperone formed with naphthalene-2-sulfonic acid, the characteristic x-ray powder diffraction peaks are summarised in the following table:

TABLE 4

| Peak number: | Position [°2θ] | d-value [Å] | Relative intensity [%] |
|---|---|---|---|
| 1 | 3.87 | 22.80 | 15 |
| 2 | 5.82 | 15.18 | 5 |
| 3 | 7.76 | 11.38 | 3 |
| 4 | 9.93 | 8.90 | 1 |
| 5 | 10.41 | 8.49 | 2 |
| 6 | 10.99 | 8.04 | 1 |
| 7 | 12.35 | 7.16 | 1 |
| 8 | 12.95 | 6.83 | 1 |
| 9 | 13.63 | 6.49 | 6 |
| 10 | 13.77 | 6.42 | 3 |
| 11 | 14.31 | 6.18 | 3 |
| 12 | 14.67 | 6.03 | 5 |
| 13 | 15.09 | 5.86 | 48 |
| 14 | 15.57 | 5.69 | 20 |
| 15 | 16.08 | 5.51 | 6 |
| 16 | 16.62 | 5.33 | 3 |
| 17 | 17.38 | 5.10 | 19 |
| 18 | 17.58 | 5.04 | 5 |
| 19 | 17.77 | 4.99 | 5 |
| 20 | 18.02 | 4.92 | 5 |
| 21 | 18.52 | 4.79 | 9 |
| 22 | 19.04 | 4.66 | 8 |
| 23 | 19.46 | 4.56 | 7 |
| 24 | 19.91 | 4.46 | 1 |
| 25 | 20.26 | 4.38 | 32 |
| 27 | 21.04 | 4.22 | 20 |
| 28 | 21.46 | 4.14 | 5 |
| 29 | 21.68 | 4.10 | 2 |
| 30 | 22.17 | 4.01 | 2 |
| 31 | 22.65 | 3.92 | 3 |
| 32 | 22.92 | 3.88 | 2 |
| 33 | 23.44 | 3.79 | 5 |
| 34 | 23.81 | 3.73 | 5 |
| 35 | 24.33 | 3.66 | 9 |
| 36 | 24.83 | 3.58 | 4 |
| 37 | 25.43 | 3.50 | 3 |
| 38 | 26.36 | 3.38 | 1 |
| 39 | 26.61 | 3.35 | 1 |
| 40 | 27.20 | 3.28 | 35 |
| 41 | 27.77 | 3.21 | 3 |
| 42 | 28.24 | 3.16 | 3 |
| 43 | 28.55 | 3.12 | 4 |
| 44 | 28.91 | 3.09 | 1 |
| 45 | 29.29 | 3.05 | 2 |
| 46 | 30.02 | 2.97 | 1 |
| 47 | 31.96 | 2.80 | 1 |
| 48 | 32.53 | 2.75 | 2 |
| 49 | 33.07 | 2.71 | 3 |
| 50 | 33.43 | 2.68 | 4 |
| 51 | 34.29 | 2.61 | 2 |

The formula (VIII) crystalline salt of lumateperone formed with naphthalene-2-sulfonic acid may be characterised with its x-ray powder diffraction image, which corresponds to FIG. 7.

The object of the invention also relates to the production of the lumateperone naphthalene-2-sulfonic acid salt so that the lumateperone base is reacted with naphthalene-2-sulfonic acid. According to a preferable embodiment of the invention the formula (VIII) lumateperone naphthalene-2-sulfonic acid salt is produced by reacting the formula (I) lumateperone base with naphthalene-2-sulfonic acid. In the course of the method the amount of naphthalene-2-sulfonic acid used is 1.5 to 2.5 times, preferably 1.8 to 2.2 times, even more preferably 1.9 to 2.1 times, most preferably two times the molar amount of the formula (I) lumateperone base. The formula (X) lumateperone naphthalene-2-sulfonic acid salt may be produced so that in the course of the method the amount of naphthalene-2-sulfonic acid used is 0.7 to 1.2 times, preferably 0.9 to 1.1 times, even more preferably 0.95 to 1.05 times, most preferably in an equivalent amount to the molar amount of the formula (I) lumateperone base.

According to a very preferable embodiment of the invention in the course of the production of naphthalene-2-sulfonic acid salts the formula (I) lumateperone base is dissolved in an organic solvent, then the naphthalene-2-sulfonic acid is added to it, then the salt obtained is isolated, then washed and dried if necessary. Alternatively the process may also involve by adding a solution of the naphthalene-2-sulfonic acid in an organic solvent to the lumateperone base solution, then if necessary the precipitated crystals are stirred, then filtered, washed and dried. The organic solvent used may be dipolar aprotic solvents, preferably nitrile or ketone type solvents, the nitrile type solvent may be acetonitrile, the ketone type solvent used may be methyl ethyl ketone, tert-butyl methyl ketone or acetone, preferably a ketone type solvent is used, most preferably acetone. In the course of salt production the temperature of the mixture is maintained at between 0 to 50° C., preferably between 20 to 25° C., most preferably at room temperature. In the course of the method, before the salt forming in the reaction mixture is filtered out it is stirred for between 2 to 48 hours, preferably for 12 to 36 hours, even more preferably for 18 to 26 hours, most preferably for 24 hours at room temperature.

The object of the invention also relates to the novel formula (IX) salt of the formula (I) lumateperone formed with p-toluenesulfonic acid, in which the molar ratio of lumateperone to p-toluenesulfonic acid is 1:2. It was found that the formula (IX) salt may be produced simply on the industrial scale at a quality suitable for the pharmaceutical industry at a chemical purity greater than 97%, preferably greater than 99%, even more preferably greater than 99.5% and at an enantiomer purity level greater than 97%, preferably greater than 99%, even more preferably greater than 99.5% using the method according to the invention.

According to an especially preferable embodiment of the invention the salt of lumateperone formed with p-toluenesulfonic acid is morphologically uniform.

An especially preferable embodiment of the invention is the formula (IX) morphologically uniform lumateperone p-toluenesulfonic acid salt, in which salt the molar ratio of the formula (I) lumateperone and p-toluenesulfonic acid is 1:2, and the positions of the characteristic x-ray powder diffraction peaks are [°2θ(±0.2 °2θ)]: 4.15; 17.10; 20.41, preferably [°2θ(±0.2 °2θ)]: 4.15; 10.40; 15.37; 17.10; 20.41; 20.64, even more preferably [°2θ(±0.2 °2θ)]: 4.15; 8.31; 10.40; 14.15; 15.37; 17.10; 18.65; 20.41; 20.64; 24.00; 27.30.

A further especially preferable embodiment of the invention is the formula (IX) morphologically uniform salt of lumateperone formed with p-toluenesulfonic acid, in which salt the molar ratio of the formula (I) lumateperone and p-toluenesulfonic acid is 1:2 and the characteristic x-ray powder diffraction peaks are summarised in the following table:

TABLE 5

| Line number: | Position [°2θ] | d-value [Å] | Relative intensity [%] |
| --- | --- | --- | --- |
| 1 | 4.15 | 21.27 | 47 |
| 2 | 6.22 | 14.19 | 3 |
| 3 | 8.31 | 10.63 | 7 |
| 4 | 9.42 | 9.38 | 1 |
| 5 | 9.75 | 9.07 | 2 |
| 6 | 10.40 | 8.50 | 12 |
| 7 | 10.93 | 8.09 | 2 |
| 8 | 11.49 | 7.69 | 1 |
| 9 | 11.89 | 7.44 | 3 |
| 10 | 12.13 | 7.29 | 3 |
| 11 | 13.55 | 6.53 | 2 |
| 12 | 13.69 | 6.46 | 5 |
| 13 | 13.88 | 6.37 | 2 |
| 14 | 14.15 | 6.25 | 18 |
| 15 | 14.49 | 6.11 | 18 |
| 16 | 14.90 | 5.94 | 19 |
| 17 | 15.37 | 5.76 | 27 |
| 18 | 15.90 | 5.57 | 23 |
| 19 | 16.48 | 5.38 | 20 |
| 20 | 17.10 | 5.18 | 44 |
| 21 | 17.93 | 4.94 | 23 |
| 22 | 18.65 | 4.75 | 22 |
| 23 | 19.19 | 4.62 | 4 |
| 24 | 19.78 | 4.49 | 3 |
| 25 | 20.41 | 4.35 | 100 |
| 26 | 20.64 | 4.30 | 57 |
| 27 | 21.05 | 4.22 | 10 |
| 28 | 21.31 | 4.17 | 17 |
| 29 | 21.56 | 4.12 | 9 |
| 30 | 21.89 | 4.06 | 2 |
| 31 | 22.30 | 3.98 | 9 |
| 32 | 22.51 | 3.95 | 10 |
| 33 | 22.94 | 3.87 | 12 |
| 34 | 23.22 | 3.83 | 5 |
| 35 | 24.00 | 3.71 | 20 |
| 36 | 24.59 | 3.62 | 3 |
| 37 | 25.17 | 3.54 | 13 |
| 38 | 25.90 | 3.44 | 4 |
| 39 | 26.07 | 3.41 | 3 |
| 40 | 26.87 | 3.32 | 5 |
| 41 | 27.30 | 3.26 | 37 |
| 42 | 27.66 | 3.22 | 17 |
| 43 | 28.57 | 3.12 | 3 |
| 44 | 28.93 | 3.08 | 7 |
| 45 | 29.29 | 3.05 | 4 |
| 46 | 29.65 | 3.01 | 1 |
| 47 | 30.16 | 2.96 | 5 |
| 48 | 30.46 | 2.93 | 1 |
| 49 | 31.00 | 2.88 | 1 |
| 50 | 31.61 | 2.83 | 2 |
| 51 | 32.16 | 2.78 | 3 |
| 52 | 32.55 | 2.75 | 1 |
| 53 | 33.53 | 2.67 | 2 |
| 54 | 34.14 | 2.62 | 1 |
| 55 | 34.61 | 2.59 | 1 |

A further especially preferable embodiment of the invention is the formula (IX) morphologically uniform salt of lumateperone formed with p-toluenesulfonic acid, in which salt the molar ratio of the formula (I) lumateperone and p-toluenesulfonic acid is 1:2, the x-ray powder diffraction image of which corresponds to FIG. 10.

The object of the invention also relates to a method for the production of the formula (IX) morphologically uniform salt of lumateperone formed with p-toluenesulfonic acid, in which salt the molar ratio of the formula (I) lumateperone and p-toluenesulfonic acid is 1:2. The method may involve that the formula (I) lumateperone base is reacted with an amount of p-toluenesulfonic acid that is 1.5 to 2.5 times, preferably 1.8 to 2.2 times, even more preferably 1.9 to 2.1 times, most preferably two times the molar amount of the formula (I) lumateperone base. According to a very preferable embodiment of the invention the formula (I) lumateperone base is dissolved in an organic solvent, then the p-toluenesulfonic acid is added to this, then the salt obtained is isolated, and washed and dried if necessary. The method may also involve adding a solution of the p-toluenesulfonic acid in an organic solvent to the lumateperone base solution, then if necessary the precipitated crystals are stirred, then filtered, washed as dried. The organic solvent used may be dipolar aprotic solvents, preferably nitrile or ketone type solvents, the nitrile type solvent may be acetonitrile, the ketone type solvent used may be methyl ethyl ketone, tert-butyl methyl ketone or acetone, preferably a ketone type solvent is used, most preferably acetone. In the course of salt production the temperature of the mixture is maintained at between 0 to 50° C., preferably between 20 to 25° C., most preferably at room temperature. In the course of the method, the formula (IX) lumateperone-toluenesulfonic acid salt forming in the reaction mixture, in which the molar ratio of the formula (I) lumateperone and p-toluenesulfonic acid is 1:2, is stirred for between 2 to 48 hours, preferably for 12 to 36 hours, even more preferably for 18 to 26 hours at room temperature, before filtering out.

Salts with high chemical and enantiomer purity may only be produced without the use of a chiral chromatography method if the lumateperone base used for the salt formation already has a sufficient level of chemical and enantiomer purity. This was not possible without chiral chromatography purification according to the state of the art. This is why the preferable embodiment of the invention has great significance, according to lumateperone may be produced with a novel method that makes it possible to avoid isolation using chiral chromatography. The method provides a much purer base than the formula (II) base

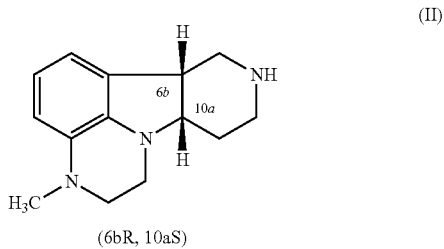 [SMILES: CN1CCN2c3c(cccc31)[C@@H]1CNCC[C@@H]12]

(6bR, 10aS)

that can be obtained using the synthesis described in document WO 2008112280, the HPLC purity of which is 88%. The method involves resolution and then alkylating the resolved cis enantiomer to provide the high-purity lumateperone, the chemical and/or enantiomer purity of which is greater than 97%, preferably greater than 99%, even more preferably greater than 99.5%. The lumateperone obtained in this way is reacted with p-toluenesulfonic acid, p-toluenesulfonic acid monohydrate, naphthalene-2-sulfonic acid or naphthalene-2-sulfonic acid hydrate.

The object of the invention also relates to pharmaceutical preparations that contain the lumateperone or its salt produced using one of the methods described in the present application. According to another embodiment of the invention the pharmaceutical preparations contain the formula (III) amorphous salt of lumateperone, in which the molar ratio of lumateperone to p-toluenesulfonic acid is 1:1, or the formula (IX) salt of lumateperone formed with p-toluenesulfonic acid, in which the molar ratio of lumateperone to p-toluenesulfonic acid is 1:2, or the formula (VIII) salt, in which the molar ratio of lumateperone to naphthalene-2-sulfonic acid is 1:2, or the formula (X) salt, in which the molar ratio of lumateperone to naphthalene-2-sulfonic acid is 1:1. In the most preferable case they contain the formula (III) amorphous salt, in which the molar ratio of lumateperone to p-toluenesulfonic acid is 1:1, or the formula (VIII) salt, in which the molar ratio of lumateperone to naphthalene-2-sulfonic acid is 1:2. In the pharmaceutical preparations according to the invention the enantiomer purity of the lumateperone or of its salt, preferably of the formula (III) novel amorphous salt of lumateperone, in which the molar ratio of lumateperone to p-toluenesulfonic acid is 1:1, or of the formula (IX) salt of lumateperone formed with p-toluenesulfonic acid, in which the molar ratio of lumateperone to p-toluenesulfonic acid is 1:2, or of the formula (VIII) salt, in which the molar ratio of lumateperone to naphthalene-2-sulfonic acid is 1:2, or of the formula (X) salt, in which the molar ratio of lumateperone to naphthalene-2-sulfonic acid is 1:2, is greater than 97%, preferably greater than 99%, even more preferably greater than 99.5%.

Indeed, it was found that the formula (III) amorphous salt, the formula (IX) ditosylate, the formula (X) napsylate, in which the molar ratio of lumateperone to naphthalene-2-sulfonic acid is 1:1, and the formula (VIII) naphthalene-2-sulfonic acid salts that can be directly used in pharmaceutical preparations, can be simply produced in a quality used in the pharmaceutical industry with the method described in the present invention, at a chemical purity greater than 97%, preferably greater than 99%, and even more preferably greater than 99.5% and at a level of enantiomer purity greater than 97%, preferably greater than 99%, and even more preferably greater than 99.5%.

In addition the salts obtained in this way are morphologically uniform, among which the formula (IX) ditosylate and the formula (VIII) naphthalene-2-sulfonic acid salt have a high melting point.

Therefore, the objection of the invention relates to a pharmaceutical preparation that contains the formula (III) novel amorphous salt of lumateperone, in which the molar ratio of lumateperone to p-toluenesulfonic acid is 1:1, or the formula (IX) salt of lumateperone formed with p-toluenesulfonic acid, or the formula (VIII) salt, or the formula (X) salt, most preferably the amorphous form of the formula (III) salt, or the formula (VIII) salt and, in addition to this, at least one excipient. According to an exceptionally preferable embodiment of the invention the lumateperone salt used in the pharmaceutical preparation in addition to the excipient, preferably the formula (III) amorphous salt, the formula (VIII) salt, the formula (X) salt, in which the molar ratio of lumateperone to p-toluenesulfonic acid is 1:1, or the formula (IX) salt is morphologically uniform.

The characteristic x-ray powder diffraction peaks of the crystalline formula (III) morphologically uniform amorphous salt in the pharmaceutical preparation according to the invention, in which the molar ratio of the formula (I) lumateperone to p-toluenesulfonic acid is 1:1, may be characterised with the diffractogram presented in FIG. 5. According to another embodiment of the pharmaceutical preparation according to the invention the positions of the characteristic x-ray powder diffraction peaks of the morphologically uniform formula (VIII) lumateperone naphthalene-2-sulfonic acid salt contained in the pharmaceutical preparation may be characterised with the data given in Table 4 or with the diffractogram presented in FIG. 7.

According to another embodiment of the pharmaceutical preparation according to the invention the salt of lumateperone formed with naphthalene-2-sulfonic acid used in the pharmaceutical preparation is morphologically uniform. The positions of the x-ray powder diffraction peaks characteristic of the crystalline formula (VIII) lumateperone naphthalene- 2-sulfonic acid salt contained in the pharmaceutical preparation according to the invention are [°2θ(±0.2 °2θ)]: 3.87; 15.09; 20.71, preferably [°2θ(±0.2 °2θ)]: 3.87; 5.82; 15.09; 17.38; 20.71; 27.20, more preferably [°2θ(±0.2 °2θ)]: 3.87; 5.82; 7.76; 13.63; 15.09; 15.57; 17.38; 18.52; 20.26; 20.71; 21.04; 27.20. The characteristic positions of the x-ray powder diffraction peaks of the crystalline formula (VIII) lumateperone naphthalene-2-sulfonic acid salt contained in the pharmaceutical preparation according to the invention may be characterised by the data given in Table 4 or with the diffractogram presented in FIG. 7.

Another embodiment of the pharmaceutical preparation according to the invention contains the formula (IX) crystalline salt, in which the molar ratio of the formula (I) lumateperone and the p-toluenesulfonic acid is 1:2, and the positions of the characteristic x-ray powder diffraction peaks are [°2θ(±0.2 °2θ)]: 4.15; 17.10; 20.41, preferably [°2θ(±0.2 °2θ)]: 4.15; 10.40; 15.37; 17.10; 20.41; 20.64, more preferably [°2θ(±0.2 °2θ)]: 4.15; 8.31; 10.40; 14.15; 15.37; 17.10; 18.65; 20.41; 20.64; 24.00; 27.30.

The positions of the characteristic x-ray powder diffraction peaks of the formula (IX) crystalline salt, in which the molar ratio of the formula (I) lumateperone and the p-toluenesulfonic acid is 1:2, may be characterised with the data given in Table 5, or with the diffractogram presented in FIG. 10. The formula (IX) salt used is morphologically uniform.

As excipients the pharmaceutical preparation according to the invention contains a filler, and optionally, a glidant, free-flowing agent, antistripping and anti-adhesion agents, binder, disintegrant and lubricant.

The pharmaceutical preparations according to the invention are preferably produced in the form of dose units. The dose units contain the desired amount of the active substance. The dose units are marketed in packaged form, which contain the separated amounts of the preparations (e.g. packaged tablets, capsules, powder in a vial or ampoule). The dose unit relates to the capsule, tablet, sachet, lozenge itself and to the packaging containing the required number of unit doses.

The pharmaceutical preparations according to the invention may be administered orally or parenterally. Orally administered preparations include, for example, tablets, capsules, dragee, solutions, elixirs, suspensions and emulsions. Preparations administered parenterally preferably include injection or infusion preparations that may be administered intravenously or intramuscularly.

Most preferably the salts according to the invention may be administered in the form of immediately absorbed tablets.

The pharmaceutical preparations according to the invention may contain the conventional pharmaceutical carriers and/or excipients. Carriers that may be used include, for example, magnesium carbonate, magnesium stearate, talc, sugar, lactose, pectin, dextrin, starch, gelatine, tragacanth, methyl cellulose, sodium carboxymethyl cellulose, low melting point wax, PEG, cocoa butter, etc. In the case of capsules it is frequently the material of the capsule that serves as the carrier and in such a case there is no need for a separate carrier material. Oral preparations also include sachets and lozenges. Tablets, powders, capsules, pills, sachets and lozenges are especially suitable solid preparation forms for oral administration.

The preparation according to the invention may also contain filler amounting to 20-90 m/m % with respect to the weight of the preparation. The amount of the filler is more preferably 40-80 m/m %, most preferably 60-80 m/m %.

Any filler used in the pharmaceutical industry that does not affect the stability of the active substances may be used as filler. The pharmaceutical preparation may contain as such filler organic polymers, such as microcrystalline cellulose, organic mono- or di- or polysaccharides or sugar alcohols, such as lactose, mannitol, sucrose, or inorganic salts, such as tricalcium phosphate, calcium phosphate, calcium carbonate and sodium chloride. In the most preferable embodiment of the invention the preparation contains microcrystalline cellulose and/or mannitol as filler.

For the purpose of accelerating release the preparation according to the invention may optionally contain substances aiding disintegration. Generally, these are materials that swell due to the effect of moisture and so push the tablet or capsule apart, and so releasing the active substance particles in the preparation. The substances aiding disintegration are usually organic polymers. Their amount in the preparation according to the invention is preferably 1-30 m/m %, more preferably 10-25 m/m %, and even more preferably 10-20 m/m %. All disintegrants used in the pharmaceutical industry may be used as a substance facilitating disintegration, a disintegrant that does not interact with the active substances. The preparation contains as a disintegrant preferably an organic polymer, such as cross-linked polyvinylpyrrolidone (Polyplasdone, preferably polyplasdone XL 10), or microcrystalline cellulose, or starch, such as corn starch or wheat starch, pregelatinized starch, or modified starch, such as sodium carboxymethyl starch (Primojel). According to the most preferable embodiment of the invention the preparation contains sodium carboxymethyl starch, sodium starch glycolate (Primojel).

If necessary the preparation may also contain a binder material. Any binder used in the pharmaceutical industry that does not interact with the active substances may be used as binder. These include, for example, organic polymers, such as hydroxypropylmethyl cellulose (hypromellose), hereinafter HPMC, preferably low viscosity HPMC with viscosity under 10000 mPas in a 2% aqueous solution at 20° C., more preferably a HPMC with viscosity of between 3000 and 6000 mPas is used. Such HPMC includes, for example, Pharmacoat 603 or 606. Polyvinylpyrrolidone, hereinafter PVP, may also be used for this purpose, of which preferably the lower polymerisation factor versions, such as the K-15 or K30 types are used. Hydroxypropyl cellulose is also a very preferable binder.

Preferably the preparation contains 1-10 m/m % binder, more preferably 1-5 m/m % binder, most preferably 1-2 m/m % binder.

In order to facilitate its formulation, a preferable embodiment of the preparation also contains lubricant reducing friction and glidant enabling free-flow.

The amount of the friction-reducing substances calculated with respect to the mass of the preparation is 0.1-10 m/m %, preferably 0.1-5 m/m %, and even more preferably 0.2-2 m/m %. As friction-reducing substance, the preparation may contain the organic or inorganic friction-reducing agents used in the pharmaceutical industry, such as, for example, stearates, preferably magnesium stearate, sodium stearyl fumarate, glyceryl behenate (e.g. Compritol 888), or inorganic substances, such as talc.

Any substance improving free-flow used in the pharmaceutical industry, may be used as glidant, such as talc, colloidal silicon dioxide or, for example, tricalcium phosphate. The amount of the substance used to improve free-flow in the preparation is 0.1-10 m/m %, preferably 0.1-5 m/m %, most preferably 0.1-2 m/m %.

If necessary the preparations according to the invention may be coated. The coating may be of an aesthetic nature or functional, such as a coating modifying release. The coating may contain any coating agent that may be used in the pharmaceutical industry, such as an organic polymer that does not react with the active substances. Preferably polymers may be used that swell or dissolve in water, so that the active substances are released quickly from the tablet. Such a polymer is, preferably, HPMC, among which the preferably low viscosity HPMC with viscosity under 10000 mPas in a 2% aqueous solution at 20° C., more preferably HPMC with viscosity of between 3000 and 6000 mPas is used. Such an HPMC type is, for example, Pharmacoat 603 or 606. Polyvinylpyrrolidone may also be used for this purpose. In a preferable embodiment of the invention the lower polymerisation factor versions, such as the K-15 or K30 types may be used. The preparation may preferably contain the coating agent in 1-10 m/m %, even more preferably in 1-5 m/m %, most preferably in 1-3 m/m %.

The preparations according to the invention contain the lumateperone or its salt produced using a method described in the present application, preferably the formula (III) amorphous salt, the formula (VIII) salt, or the formula (IX) salt, the enantiomer purity of which is greater than 97%, preferably greater than 99% and even more preferably greater than 99.5%, and they may be used for the production of sustained active substance release or delayed active substance release preparations as well. In such a case the preparation may be provided with a functional, preferably enterosolvent polymer coating. Such polymers may be produced using, for example, methyl acrylate methacrylic acid copolymers, cellulose acetate succinate, hydroxypropyl methylcellulose phthalate, hydroxypropyl methylcellulose acetate succinate (hypromellose acetate succinate), polyvinyl acetate phthalate (PVAP), methyl methacrylate methacrylic acid copolymers, shellac cellulose acetate trimellitate, sodium alginate based polymers.

Suppositories contain low melting point wax as carrier material (e.g. fatty acid triglyceride mixtures, PEG or cocoa butter). The wax is melted and then the active substance is homogenously distributed in the melt. The melted homogenous mixture is then poured into a casting mould of the appropriate size and shape, and left to solidify during cooling.

The object of the invention also relates to a method for the production of pharmaceutical preparations containing the lumateperone or its salt produced using a method described in the present application, or the formula (III) amorphous lumateperone salt according to the invention, in which the molar ratio of lumateperone to p-toluenesulfonic acid is 1:1, or the formula (IX) salt of lumateperone formed with p-toluenesulfonic acid, in which the molar ratio of lumateperone to p-toluenesulfonic acid is 1:2, the salt of lumateperone formed with naphthalene-2-sulfonic acid, preferably the formula (X) salt, in which the molar ratio of lumateperone to naphthalene-2-sulfonic acid is 1:1, or the salt of lumateperone formed with naphthalene-2-sulfonic acid, preferably the formula (VIII) salt, in which the molar ratio of lumateperone to naphthalene-2-sulfonic acid is 1:2, most preferably the novel formula (III) amorphous salt or the formula (VIII) salt, in which the chemical and/or enantiomer purity of the lumateperone salt used is greater than 97%, preferably greater than 99%, even more preferably greater than 99.5%, characterised by that a.) the active substance is mixed with carriers with suitable characteristics in the appropriate ratio, or b.) the active substance is granulated either wet or dry with a part of the excipients, then the granulate obtained is dried if necessary, and the mixture obtained in this way is tableted or filled into capsules.

The pharmaceutical preparations according to the invention are produced using the conventional pharmaceutical production methods.

More specifically the tablets may be produced by mixing the active substance with carrier materials that have suitable characteristics in the appropriate ratio, and then by pressing tablets from the mixture of the desired shape and size. Capsules may be produced with any process for producing tablets with the difference that the mixtures or homogenates containing the obtained powder mixture, or the granules and other excipients are not pressed into tablets, but, instead are filled into capsules, preferably into soft gelatine capsules.

The capsules and tablets may be produced so that the active substance is granulated with a part of the excipients dry (e.g. with a compactor) or wet by, for example, kneading, extrusion granulation or fluid granulation, then the granules obtained are dried if necessary and pressed into tablets or filled into capsules.

The method may preferably involve mixing the formula (III) lumateperone salt according to the invention, the uniform morphology salts of the formula (I) lumateperone, the amorphous novel formula (III) salt, in which the molar ratio of lumateperone to p-toluenesulfonic acid is 1:1, or the formula (IX) salt of lumateperone formed with p-toluenesulfonic acid, in which the molar ratio of lumateperone to p-toluenesulfonic acid is 1:2, the salt of lumateperone formed with naphthalene-2-sulfonic acid, preferable the formula (X) salt, in which the molar ratio of lumateperone to naphthalene-2-sulfonic acid is 1:1, or the formula (VIII) salt, in which the molar ratio of lumateperone to naphthalene-2-sulfonic acid is 1:2, is mixed with filler or with filler and disintegrant, then the mixture obtained is granulated with a binder material, preferably with an aqueous solution or suspension of binder material, then the granules obtained are dried, spheronized if necessary, regranulated, then the granules obtained are mixed with further excipients and pressed into tablets or filled into capsules.

The granulation is preferably performed in a fluid granulation device. Most preferably mannitol and/or microcrystalline cellulose is used as the filler, and hydroxypropyl cellulose is used as the binder. Before tableting, the granulate is mixed with further filler, preferably with microcrystalline cellulose and a lubricant, preferably magnesium stearate.

Another aspect of the invention relates to the use of the formula (III) amorphous lumateperone salt, in which the molar ratio of formula (I) lumateperone and p-toluenesulfonic acid is 1:1, or the formula (IX) salt of lumateperone formed with p-toluenesulfonic acid, in which the molar ratio of lumateperone to p-toluenesulfonic acid is 1:2, the salt of lumateperone formed with naphthalene-2-sulfonic acid, preferably the formula (X) salt, in which the molar ratio of lumateperone to naphthalene-2-sulfonic acid is 1:1, or the formula (VIII) salt, in which the molar ratio of lumateperone to naphthalene-2-sulfonic acid is 1:2, for the production of a pharmaceutical preparation for the treatment of psychosis, schizophrenia, depression, bipolar depression, sleep and behavioural disorders, behavioural disorders related to dementia, neuropsychiatry diseases, mental disorders, and mental illnesses.

The object of the invention also relates to a treatment method for the treatment of psychosis, schizophrenia, depression, bipolar depression, sleep and behavioural disorders, behavioural disorders related to dementia, neuropsychiatry diseases, mental disorders, and mental illnesses in such a way that patients suffering from such conditions are administered an effective dose of a pharmaceutical preparation containing the formula (III) amorphous lumateperone salt, in which the molar ratio of formula (I) lumateperone and p-toluenesulfonic acid is 1:1, or the formula (IX) salt of lumateperone formed with p-toluenesulfonic acid, in which the molar ratio of lumateperone to p-toluenesulfonic acid is 1:2, the salt of lumateperone formed with naphthalene-2-sulfonic acid, preferably the formula (X) salt, in which the molar ratio of lumateperone to naphthalene-2-sulfonic acid is 1:1, or the formula (VIII) salt, in which the molar ratio of lumateperone to naphthalene-2-sulfonic acid is 1:2.

The invention is accordingly summarised as follows:

Method for the production of formula (I) lumateperone or its acid addition salts, in such a way that the stereoisomers of the formula (IV) cis racemate compound are isolated and the formula (II) stereoisomer with stereochemistry 6bR, 10aS obtained in this way is alkylated with the general formula compound (VII) 4-halo-4'-fluoro butyrophenone (X=I, Br, Cl) to form the formula (I) lumateperone, or, optionally acid addition salt.

More specifically, in the course of the method a.) the formula (IV) compound is reacted with one of the enantiomers of a chiral acid, then the salt of the formula (II) compound formed with chiral acid, in the formula of which compound (II) the configuration of the chiral carbon atoms is 6bR,10aS, is isolated from the reaction mixture and transformed into formula (II) base, or the method may also involve b.) that the formula (IV) compound is reacted with another enantiomer of the above chiral acid, then the salt of the formula (II/A) compound, in which formula the configuration of the chiral carbon atoms is 6bS, 10aR, formed with a chiral acid is isolated from the reaction mixture, and so the formula (II) compound, in which formula the configuration of the chiral carbon atoms is 6bR,10aS, enriched in this way in the reaction mixture is isolated, then the formula (II) compound obtained in this way, in the formula of which the configuration of the chiral carbon atoms is 6bR,10aS, is transformed into lumateperone.

Furthermore, the method may also involve that the salt of the formula (II) compound formed with a chiral acid is transformed into a salt with a non-chiral acid, preferable into a salt formed with a mineral acid, preferably into hydrogen halide salt, even more preferably into hydrogen chloride salt, then this salt is transformed into the formula (II) base, which then is transformed into lumateperone.

The invention also relates to a method for the production of the formula (II) base and the formula (I) lumateperone, a.) the formula (V) (+)-dibenzoyl-D-tartaric acid mono (dimethylamide), as chiral acid, is added to the solution of the formula (IV) stereoisomer mixture, then the formula (VI) salt is separated from the solution, which, if required is transformed directly into a base, or into a salt formed with a mineral acid, preferably into a hydrogen halide salt, even more preferably into hydrogen chloride salt, then this salt is transformed into the formula (II) base, or the method may also involve b.) adding the formula (V/A) (−)-dibenzoyl-L-tartaric acid mono(dimethylamide), as chiral acid, to the solution of the formula (IV) stereoisomer mixture, isolating the formula (VI/A) compound from the solution, then from the solution enriched in the formula (II) stereoisomer, in which formula (II) the configuration of the chiral carbon atoms is 6bR,10aS, the formula (II) compound is separated in the form of a salt or base, then if necessary the separated compound is transformed into a base and alkylated. This latter method version may also be implemented so that from the solution enriched in the stereisomer of the general formula (II)

i.) the formula (II) stereoisomer base precipitated with the concentration of the solution is separated and crystallized if necessary, or ii.) by forming a salt from the mother liquor using a chiral acid, preferably the formula (V) (+)-dibenzoyl-D-tartaric acid mono(dimethylamide), or a non-chiral organic or inorganic acid preferably hydrochloric acid, hydrogen bromide or hydrogen iodide, most preferably hydrochloric acid, and the salt is filtered out, and optionally the salt is transformed into the formula (II) stereoisomer base, then the base obtained in this way is transformed into lumateperone.

In the course of the implementation of the invention the enantiomer purity of the formula (II) and/or (I) compounds, in which formula (II) or (I) compounds the configuration of the chiral carbon atoms is 6bR,10aS, or of their salts is greater than 97%, preferably greater than 99%, even more preferably greater than 99.5%. Furthermore the chemical purity of the formula (II) and/or (I) compounds produced in the course of the present method, in which formula (II) or (I) compounds the configuration of the chiral carbon atoms is 6bR,10aS, or of their salts is greater than 97%, preferably greater than 99%, even more preferably greater than 99.5%.

According to a preferable embodiment of the invention, following the alkylation of the formula (II) compound, in which the configuration of the chiral carbon atoms is 6bR, 10aS, the formula (I) lumateperone base obtained is transformed into a salt, preferably p-toluenesulfonic acid salt, or into naphthalene-2-sulfonic acid salt, more preferably into the formula (III) or (IX) p-toluenesulfonic acid salt, or into the formula (VIII) or (X) naphthalene-2-sulfonic acid salt, most preferably into the amorphous form of the formula (III) p-toluenesulfonic acid salt, or into the formula (VIII) naphthalene-2-sulfonic acid salt The method may also involve that a.) the formula (II) compound, in which the configuration of the chiral carbon atoms is 6bR,10aS, is used in the alkylation reaction in the form of a base, or the method may also involve b.) the formula (II) base, in which the configuration of the chiral carbon atoms is 6bR,10aS, being released in the alkylation reaction mixture from the salt form.

An amount of 1.2 to 2 equivalents, preferably 1.5 equivalents of preferably 4-chloro-4'-fluoro butyrophenone or 4-iodo-4'-fluoro butyrophenone with respect to the amount of the formula (II) base is used for the alkylation, and the alkylation is performed preferably in an aprotic solvent, preferably in acetonitrile or in toluene, preferably in toluene at a temperature between room temperature and the boiling point of the solvent, preferably at the boiling point of the solvent, optionally in the presence of an organic base, preferably a tertiary amine, even more preferably in the presence of triethylamine or N,N-diisopropylethylamine, most preferably triethylamine or an inorganic base, preferably potassium carbonate or caesium carbonate, even more preferably caesium carbonate.

According to a preferable embodiment of the invention the isolation of the formula (II) compound from the formula (IV) cis racemate is carried out in an organic solvent medium, in a solvent containing an alcohol with 1 to 4 carbon atoms, preferably in an alcohol with 1 to 4 carbon atoms, more preferably in ethanol or methanol, even more preferably in 96% or anhydrous ethanol or methanol, most preferably in methanol. Preferably the separation is performed by resolution, in such a way that preferably chiral carboxylic acid is used as the resolution agent, even more preferably the formula (V) or (V/A) compounds, and most preferably the formula (V) (+)-dibenzoyl-D-tartaric acid mono(dimethylamide) is used as the resolution agent, at an amount of 0.5 to 1 equivalent calculated with respect to the formula (IV) cis racemate, preferably 0.7 equivalents. In the course of the resolution process the temperature of the mixture is maintained at between 0 to 50° C., preferably between 20 to 25° C., most preferably at room temperature.

Viewing the invention more closely, according to the most preferable embodiment the formula (IV) cis racemate compound is dissolved in a solvent containing an alcohol with 1 to 4 carbon atoms, preferably in an alcohol with 1 to 4 carbon atoms, more preferably in ethanol or methanol, even more preferably in 96% or anhydrous ethanol or methanol, most preferably in methanol, then the solution is maintained at a temperature between 0 to 50° C., preferably between 20 to 25° C., most preferably at room temperature and an amount of 0.5 to 1 equivalents, preferably 0.7 equivalents of the formula (V) (+)-dibenzoyl-D-tartaric acid mono(dimethylamide) calculated with respect to the amount of the formula (IV) cis racemate is added to the solution, then the formula (VI) salt formed is separated, then a.)
- a.1.) the formula (II) base is released from the formula (VI) salt obtained and optionally crystallized, or
- a.2.) by stirring the obtained formula (VI) salt in an organic solvent, preferably ethyl acetate it is transformed into the formula (II)·2HCl salt preferably with hydrochloric acid dissolved in ethyl acetate, then the formula (II) compound is released from the salt with a base, then the base (II) produced according to point a.1.) or a.2.), the formula (VI) salt or the (II)·2HCl salt is alkylated in an organic solvent, preferably in an organic aprotic solvent, preferably in acetonitrile or toluene, most preferably in toluene, preferably at a temperature between room temperature and the boiling point of the solvent, preferably with 1.2 to 2 equivalents, more preferably 1.5 equivalents of 4-halo-4'-fluoro butyrophenone, preferably 4-chloro-4'-fluoro butyrophenone or 4-iodo-4'-fluoro butyrophenone, more preferably 4-chloro-4'-fluoro butyrophenone in the presence of potassium iodide, furthermore in the presence of an organic acid-binder, preferably a tertiary amine, more preferably triethylamine or, N-diisopropylethylamine, even more preferably triethylamine, or in the presence of an inorganic acid-binder, preferably potassium carbonate or caesium carbonate, most preferably in the presence of caesium carbonate. The lumateperone base obtained a.) is reacted with naphthalene-2-sulfonic acid, preferably with 1.5 to 2.5 times, preferably with 1.8 to 2.2 times, more preferable with 1.9 to 2.1 times, most preferably with two times the molar amount of the lumateperone base, preferably so that the naphthalene-2-sulfonic acid is added to the lumateperone base solution after being dissolved in an organic solvent, so that the mixture is maintained at between 0 to 50° C., preferably between 20 to 25° C., most preferably at room temperature, using dipolar aprotic solvents, preferably nitrile or ketone type solvents, the nitrile type solvent may be acetonitrile, the ketone type solvent used may be methyl ethyl ketone, tert-butyl methyl ketone or acetone, preferably a ketone type solvent is used, most preferably acetone as the organic solvent, then the precipitated crystals are stirred if necessary, then filtered, washed and dried, or b.) it is reacted with an amount of p-toluenesulfonic acid equal to 0.7 to 1.2 times the molar amount of the lumateperone base, preferably 0.9 to 1.1 times the amount, more preferably 0.95 to 1.05 times the amount, most preferably with an equivalent amount of p-toluenesulfonic acid, then the salt obtained
- i.) is isolated in amorphous form, or
- ii.) the formed formula (III) lumateperone p-toluenesulfonic acid salt, which is morphologically uniform, or consists of several crystals of different morphology, or of a mixture of crystalline and amorphous tosylate salts of varying morphology, is isolated, then transformed into the morphologically uniform amorphous formula (III) salt in such a way that it is dissolved in a mixture of water and a nitrile type solvent, preferably in a mixture of water and acetonitrile and then lyophilised, or c.) it is reacted with an amount of p-toluenesulfonic acid equal to 1.5 to 2.5 times the molar amount of the lumateperone base, preferably 1.8 to 2.2 times the amount, more preferably 1.9 to 2.1 times the amount, most preferably with two times the amount of p-toluenesulfonic acid, preferably in such a way that the lumateperone base is dissolved in an organic solvent, then the p-toluenesulfonic acid is added to the reaction mixture, optionally dissolved in an organic solvent so that the reaction mixture is maintained at a temperature of from 0 to 50° C., preferably a 20 to 25° C., most preferably at room temperature, using dipolar aprotic solvents, preferably nitrile or ketone type solvents, the nitrile type solvent may be acetonitrile, the ketone type solvent may be methyl ethyl ketone, tert-butyl methyl ketone or acetone, preferably a ketone type solvent, most preferably acetone is used as the organic solvent, than the formula (IX) salt obtained is isolated, and, if necessary, washed and dried, or d.) the formula (I) lumateperone base is reacted with an amount of p-toluenesulfonic acid equal to 0.7 to 1.2 times the molar amount of the lumateperone base, preferably 0.9 to 1.1 times the amount, more preferably 0.95 to 1.05 times the amount, most preferably with an equivalent amount of p-toluenesulfonic acid in an organic solvent, preferably in 2-propanol, then the formula (III) salt obtained is filtered, and, if necessary, washed and dried.

A preferable embodiment of the invention is the crystalline form of the formula (II) (6bR,10aS)-3-methyl-2,3,6b,9, 10,10a-hexahydro-1H-pyrido[3',4': 4,5]pyrrolo[1,2,3-de] quinoxaline base. The positions of the x-ray powder diffraction lines characteristic of the preferable crystalline form of the formula (II) compound are [°2θ(±0.2 °2θ)]: 9.99; 16.03; 20.87, preferably [°2θ(±0.2 °2θ)]: 9.99; 13.17; 15.25; 16.03; 20.32, 20.87, even more preferably [°2θ(±0.2 °2θ)]: 7.46; 9.99; 13.17; 15.25; 16.03; 16.38; 20.32; 20.87; 21.35; 23.18. The object of the invention also relates to the salt of formula (VI) (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide), which is crystalline. The positions of the x-ray powder diffraction lines characteristic of the preferable crystalline form are [°2θ(±0.2 °2θ)]: 6.17; 19.88; 23.58, preferably [°2θ(±0.2 °2θ)]: 6.17; 9.89; 13.56; 18.66; 19.88;

23.58, even more preferably [°2θ(±0.2°2θ)]: 6.17; 9.89; 10.37; 11.72; 12.94; 13.56; 14.92; 18.66; 19.88; 23.58. The object of the invention also relates to the salt of the formula (II) (6bR,10aS)-3-methyl-2,3,6b,9,10,10a-hexahydro-1H-pyrido[3',4': 4,5]pyrrolo[1,2,3-de]quinoxaline formed with hydrochloric acid, preferably its formula (II)·2HCl salt formed with 2 mol hydrochloric acid, as well as the novel salts of lumateperone and the morphological uniform forms of these. Such is the amorphus form formula (III) lumateperone salt, in which salt the molar ratio of the formula (I) lumateperone and p-toluenesulfonic acid is 1:1, the salt of the formula (I) lumateperone formed with naphthalene-2-sulfonic acid, preferably the formula (VIII) lumateperone salt, in which salt the molar ratio of the formula (I) lumateperone naphthalene-2-sulfonic acid is 1:2. Preferably the formula (VIII) compound is crystalline, the positions of the characteristic x-ray powder diffraction lines of which are °2θ(±0.2 °2θ)]: 3.87; 15.09; 20.71, preferably [°2θ(±0.2 °2θ)]: 3.87; 5.82; 15.09; 17.38; 20.71; 27.20, even more preferably [°2θ(±0.2 °2θ)]: 3.87; 5.82; 7.76; 13.63; 15.09; 15.57; 17.38; 18.52; 20.26; 20.71; 21.04; 27.20.

The object of the invention also relates to the production of the crystalline form of the formula (II) (6bR,10aS)-3-methyl-2,3,6b,9,10,10a-hexahydro-1H-pyrido[3',4': 4,5]pyrrolo[1,2,3-de]quinoxaline base, in such a way that
  a.) the formula (VI) salt formed with (+)-dibenzoyl-D-tartaric acid mono(dimethylamide), or the formula (II) ·2HCl salt formed with hydrochloric acid is reacted with a base, and the released formula (II) compound is brought into crystalline form, or
  b.) the formula (IV) compound is reacted with one of the enantiomers of a chiral acid, preferably the formula (V) (+)-dibenzoyl-D-tartaric acid mono(dimethylamide), then the salt of the formula (II) compound formed with chiral acid, in which formula (II) compound the configuration of the chiral carbon atoms is 6bR,10aS, is isolated from the reaction mixture and then transformed into the formula (II) base, or
  c.) reacting the formula (IV) compound with the other enantiomer of the above chiral acid, then the salt of the formula (II/A) compound formed with the chiral acid, in which the configuration of the chiral carbon atoms in the formula of the compound is 6bS,10aR, is separated from the reaction mixture, and the formula (II) compound that has been enriched in this way in the reaction mixture, in which the configuration of the chiral carbon atoms in its formula is 6bR,10aS, is isolated, then the formula (II) compound obtained in this way is crystallized. In the methods b.) and c.) the compound (V) or (V/A) is reacted as chiral acid with the formula (IV) cis racemic compound. The formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide) may also be produced by that
  a.) the formula (IV) compound is reacted with the formula (V) (+)-dibenzoyl-D-tartaric acid mono(dimethylamide), then the formula (VI) compound obtained in this way is isolated from the reaction mixture, or
  b.) reacting the formula (IV) compound with a chiral acid, preferably the formula (V/A) (−)-dibenzoyl-L-tartaric acid mono(dimethylamide), then the salt of compound (II/A) formed with chiral acid, in which the configuration of the chiral carbon atoms is 6bS,10aR, preferably the formula (VI/A) salt formed with (−)-dibenzoyl-L-tartaric acid mono(dimethylamide) is isolated from the reaction mixture, and in this way the formula (II) compound enriched in the reaction mixture is reacted with the formula (V) (+)-dibenzoyl-D-tartaric acid mono(dimethylamide), then the formula (VI) compound formed is isolated.

According to a preferable embodiment of the invention the formula (II)·2HCl salt of the formula (II) (6bR,10aS)-3-methyl-2,3,6b,9,10,10a-hexahydro-1H-pyrido[3',4': 4,5]pyrrolo[1,2,3-de]quinoxaline formed with hydrochloric acid. This is produced by stirring the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide), or the formula (II) base, then hydrochloric acid dissolved in an organic solvent, preferably in ethyl acetate, even more preferably hydrogen chloride gas dissolved in ethyl acetate is added to the reaction mixture, then the formula (II)·2HCl salt formed is separated.

The object of the invention also relates to the use of the crystalline form of formula (II) (6bR,10aS)-3-methyl-2,3,6b,9,10,10a-hexahydro-1H-pyrido[3',4': 4,5]pyrrolo[1,2,3-de]quinoxaline, of the formula (VI) (+)-dibenzoyl-D-tartaric acid mono(dimethylamide) salt, or of the formula (II)·2HCl salt for the production of lumateperone or of its salts, preferably the lumateperone p-toluenesulfonic acid salt, the naphthalene-2-sulfonic acid salt, most preferably the formula (III) amorphous form of the p-toluenesulfonic acid salt, or the formula (VIII) naphthalene-2-sulfonic acid salt.

The object of the invention relates to the production of the salt of lumateperone formed with p-toluenesulfonic acid in such a way that the formula (I) lumateperone base is reacted with an amount of p-toluenesulfonic acid equal to 0.7 to 1.2 times the molar amount of the lumateperone base, preferably 0.9 to 1.1 times the amount, more preferably 0.95 to 1.05 times the amount, most preferably with an equivalent amount of p-toluenesulfonic acid, then the salt obtained
  a.) is isolated in amorphous form, or
  b.) the formula (III) lumateperone p-toluenesulfonic acid salt formed, which consists of morphologically uniform crystals, or consists of several crystals of different morphology, or of a mixture of crystalline and amorphous tosylate salts of various morphology, is isolated, then dissolved in the mixture of water and a nitrile type solvent, preferably in a mixture of acetonitrile and water and then lyophilised.

The production of the amorphous formula (III) lumateperone p-toluenesulfonic acid salt may be carried out so that in method a.) the salt formation is carried out in a solvent mixture of water and a nitrile type solvent, preferably in a solvent mixture containing water and acetonitrile, preferably in a solvent mixture to be lyophilised, in which the volumetric ratio of the water and the nitrile type solvent in the solvent mixture to be lyophilised, preferably of water and acetonitrile at room temperature (20° C.) is 40:1-10:1, more preferably 30:1-15:1, most preferably 25:1-19:1, then the formula (III) lumateperone p-toluenesulfonic acid salt solution obtained in this way is lyophilised in such a way that the ratio of the mass of the tosylate salt with respect to the volume of the solvent (tosylate salt mass [g]/solvent volume [litre]) is preferably 0.2-100, more preferably 0.2-50, even more preferably 0.25-10, most preferably 0.3-1. According to a preferable embodiment of the method in the course of the salt formation the temperature of the mixture is maintained at between 0 to 50° C., preferably between 20 to 25° C., most preferably at room temperature, then the solution made of lumateperone monotosylate with water and a nitrile type solvent, preferably acetonitrile is cooled to a temperature lower than 0° C., preferably to between 0° C. and −200°

C., even more preferably to between −60° C. and −200° C., most preferably to a temperature between −70° C. and −100° C., then the solution obtained in this way is lyophilised at a pressure under 6.117 mbar, preferably 0.01 to 6 mbar, even more preferably 0.1 to 5 mbar, most preferably 1 to 5 mbar.

The object of the invention also relates to the production of the salt of lumateperone produced with naphthalene-2-sulfonic acid, characterised by that the formula (I) lumateperone base is reacted with naphthalene-2-sulfonic acid. Preferably the amount of naphthalene-2-sulfonic acid used is
a.) 0.7 to 1.2 times, preferably 0.9 to 1.1 times, more preferably 0.95 to 1.05 times, most preferably in an equivalent amount to the molar amount of the lumateperone base, or
b.) preferably 1.8 to 2.2 times, even more preferably 1.9 to 2.1 times, most preferably two times the molar amount of the lumateperone base. If the process is carried out according to a.) then the formula (X) salt is obtained, and if the process is carried out according to b.) then the formula (VIII) salt formed with naphthalene-2-sulfonic acid is obtained.

The formation of the naphthalene-2-sulfonic acid salt is carried out so that the lumateperone base is dissolved using an organic solvent, preferably in dipolar aprotic solvents, preferably nitrile or ketone type solvents, the nitrile type solvent is preferably acetonitrile, the ketone type solvent used is methyl ethyl ketone, tert-butyl methyl ketone or acetone, preferably a ketone type solvent is used, most preferably acetone, then the naphthalene-2-sulfonic acid is added, then the salt obtained is separated, then washed and dried if necessary. Most preferably the process involves adding to the lumateperone base solution a solution of the naphthalene-2-sulfonic acid dissolved in an organic solvent, preferably dipolar aprotic solvents, even more preferably nitrile or ketone type solvents, the nitrile type solvent is preferably acetonitrile, the ketone type solvent used is methyl ethyl ketone, tert-butyl methyl ketone or acetone, preferably a ketone type solvent is used, most preferably acetone, then if necessary the precipitated crystals are stirred, then filtered, washed and dried. In the course of salt production with naphthalene-2-sulfonic acid the temperature of the reaction mixture is maintained at between 0 to 50° C., preferably between 20 to 25° C., most preferably at room temperature, and if necessary before the salt is filtered out the reaction mixture is stirred for between 2 to 48 hours, preferably for 12 to 36 hours, even more preferably for 18 to 26 hours at room temperature.

The object of the invention relates to a pharmaceutical preparation containing the lumateperone or its salts produced using the method according to the invention, which preferably contains a salt of lumateperone formed with p-toluenesulfonic acid or naphthalene-2-sulfonic acid and, in addition, at least one excipient. Furthermore, it relates to those pharmaceutical preparations that contain the amorphous form of the formula (III) p-toluenesulfonic acid salt of lumateperone, or the naphthalene-2-sulfonic acid salt of lumateperone, preferably the formula (VIII) or (X) naphthalene-2-sulfonic acid salt and, in addition, at least one excipient. As excipients the pharmaceutical preparations according to the invention contain a filler, and optionally, a glidant, free-flowing agent, antistripping and anti-adhesion agents, binder, disintegrant and lubricant. The object of the invention relates to a method for the production of pharmaceutical preparations in which a.) the active substance is mixed with a suitable proportion of carrier materials that have the appropriate characteristics, or b.) the active substance is granulated either wet or dry with a part of the excipients, then the granulate obtained is dried if necessary, and the mixture obtained in this way is tabletted or filled into capsules.

The object of the invention relates to the use of the amorphous form of the formula (III) p-toluenesulfonic acid salt of lumateperone, or of the lumateperone naphthalene-2-sulfonic acid salt, preferably of the formula (VIII) or formula (X) naphthalene-2-sulfonic acid salt according to the invention for the production of pharmaceutical preparations serving for the treatment of psychosis, schizophrenia, depression, bipolar depression, sleep and behavioural disorders, behavioural disorders related to dementia, neuropsychiatry diseases, mental disorders, and mental illnesses.

The object of the invention relates to a treatment method for the treatment of psychosis, schizophrenia, depression, bipolar depression, sleep and behavioural disorders, behavioural disorders related to dementia, neuropsychiatry diseases, mental disorders, and mental illnesses, characterised by that that patients suffering from such conditions are administered pharmaceutical preparations containing effective doses of the amorphous form of the formula (III) p-toluenesulfonic acid salt of lumateperone, or of the lumateperone naphthalene-2-sulfonic acid salt, preferably of the formula (VIII) or formula (X) naphthalene-2-sulfonic acid salt.

The Advantages of the Invention

The advantage of the method according to the invention is that it overcomes the disadvantages of the methods according to the state of the art, namely the disadvantage of the synthesis disclosed in the description of the publication number WO 2008112280 leading through the enantiomer cis intermediate products that the base (II) can only be produced at a very low level of purity (88%) due to the side products accumulated in the oily intermediates that cannot be purified, which made it impossible to produce high-purity lumateperone base. Additionally, neither the transformation of the base into p-toluenesulfonic acid salt according to publication number WO 2009/114181 nor the production of the salts or cocrystals disclosed in the specifications WO 2017/172784 and WO 2017/172811 led to a product with an level of chemical purity that is acceptable in the pharmaceutical industry. Also the method according to the invention overcame the disadvantage of the production described in international patent application number WO 2000077002, namely that pure lumateperone base can only be produced using a chiral chromatography procedure. In other words with the present invention it is possible to produce lumateperone and lumateperone salts, preferably the lumateperone tosylate salts and naphthalene-2-sulfonate (napsylate) salts of a quality that can be used in the pharmaceutical industry without using chiral chromatography isolation.

In other words the invention makes it possible to produce pure lumateperone salts without the use of chiral chromatography by using resolution. Additionally, the salts made in this way have a stable level of chemical purity greater than 97%, preferably greater than 99%, even more preferably greater then 99.5%, and a level of enantiomer purity greater than 97%, preferably greater than 99%, even more preferably greater then 99.5% that may be used in the pharmaceutical industry without any further purification steps being necessary. This advantage was demonstrated in the case of the novel morphologically uniform salts according to the invention, i.e. the high chemical purity and/or enantiomer purity formula (III) lumateperone amorphous salt, in which formula the molar ratio of the formula (I) lumateperone and p-toluenesulfonic acid is 1:1, or the formula (IX) salt of lumateperone formed with p-toluenesulfonic acid, in which the molar ratio of lumateperone to p-toluenesulfonic acid is 1:2, or the formula (VIII) salt, in which the molar ratio of lumateperone to naphthalene-2-sulfonic acid is 1:2.

A further advantage of the method according to the invention is that the last formula (II) intermediate of the synthesis was produced by resolution the formula (IV) cis racemate compound, so in this way, contrary to the state of the art, the method provided a very pure starting material for the alkylation of lumateperone. Additionally the formula (II) compound was produced in various salt forms and as a base in a crystalline form that could be easily purified and that makes it possible to produce high-purity lumateperone.

A further advantage of the method according to the invention is that it is possible to produce crystalline salts of the last formula (II) intermediate of the synthesis, which makes it possible to purify the intermediate even further if necessary, and as stable, uniform polymorphous salts that are easy to handle and store as opposed to the contaminated oily product described in the prior art, which cannot be purified with distillation and that has 12% contaminants. By using these, the industrial production of lumateperone is much easier to schedule. Among the crystalline salts of the formula (II) compound the (II)·2HCl is especially preferable, because by transforming the formula (VI) salt into hydrochloric acid salt the formula (V) chiral salt can be recycled very effectively at a high level of purity. A further advantage of the invention is the use of (+)-dibenzoyl-D-tartaric acid mono(dimethylamide) in the resolution step, as this chiral acid makes it possible to produce the formula (VI) salt and formula (II) base at a very high level of chemical and enantiomer purity, which contributes to the production of lumateperone and lumateperone salts that are much purer than those of the state of the art.

It is obviously very preferable if morphologically uniform intermediates are used, such as the formula (II) intermediate, its formula (II)·2HCl salt, or its formula (VI) salt formed with the formula (V) resolution agent according to the invention, as, in addition to that the filtration and storage characteristics of crystalline products with a uniform structure remain unchanged in general, their use in industry is easier to plan than mixtures containing amorphous or varying polymorph forms. What is more, with isolation as crystal the key intermediate can be cleaned of the contaminants accumulated in previous steps before the later steps, or before the last step in the case of the formula (II) intermediate without the use of chromatographic purification. The advantage of the method therefore is that pure lumateperone can be produced via a crystalline intermediate, the purification of which was not possible according to the state of the art, furthermore, this was solved without the use of a chiral chromatography process, using resolution and methods that can be used on the industrial scale.

Indeed, another advantage of the method according to the invention is that by using the resolution process essentially distomer-free lumateperone salts can be obtained via a high enantiomer purity intermediate (II), preferably the amorphous and crystalline versions of the formula (III) salt of lumateperone, or its formula (VIII), (X) and (IX) salts. A further advantage of the method according to the invention is that it is a method with which morphologically uniform product can be obtained with a level of enantiomer and chemical purity that can be directly used in pharmaceutical preparations, in a very simple way, from pure lumateperone via salt formation.

The advantage of another embodiment of the invention, namely of the formula (III) lumateperone amorphous salt, in which formula the molar ratio of the formula (I) lumateperone and p-toluenesulfonic acid is 1:1, is that it makes up for a deficiency that has existed for a long time, i.e. a pure, solid active substance that can be produced at the industrial scale, which makes it possible to produce on the industrial scale pharmaceutical preparations containing the lumateperone active substance, the active substance content of which is greater than 97%, preferably greater than 99%, most preferably greater than 99.5%.

In other words the object of the invention is the formula (III) amorphous lumateperone salt, in which salt the molar ratio of the formula (I) lumateperone and p-toluenesulfonic acid is 1:1, and its advantage as compared to the state of the art is that it satisfies an old need, i.e. a lumateperone active substance in solid form that can be produced at a good yield level using methods corresponding to the demands of the pharmaceutical industry, without the use of a chiral chromatography purification step and that is suitable for the production of solid pharmaceutical preparations.

The invention is also preferable as compared to the state of the art because the amorphous active substance generally dissolves more easily than crystalline thermodynamically more stable products. The amorphous formula (III) lumateperone salt according to the present invention, in which salt the molar ratio of the formula (I) lumateperone and p-toluenesulfonic acid is 1:1, is surprisingly stable contrary to general experience. The reason for this is that the general experience with amorphous active substances is that they are less chemically stable, also while amorphous substances are left to stand, optionally, during storage, or in the pharmaceutical preparation itself they partially or completely transform into a crystalline form or into a mixture of several crystalline forms forming a morphologically inhomogeneous (non-uniform) active substance. Furthermore the solubility of the unstable amorphous compound usually differs from the solubility of the crystalline active substance, a morphological change during storage may lead to a change in the effect of the preparation. However, contrary to the general expectations it was surprising to experience that the formula (III) amorphous lumateperone salt according to the invention, in which salt the molar ratio of the formula (I) lumateperone and p-toluenesulfonic acid is 1:1, remains stable for 3 months (see FIG. 5) without transforming into the very stable polymorph form A or other form.

In FIG. 5 the curve "A" shows the XRD curve of the finished product after production, while the curve "B" shows its XRD curve, with displacement, after 3 months of storage at room temperature in a sealed vessel. It can be seen that the two curves are essentially the same, no peaks characteristic of crystalline forms are apparent even after storage.

According to DSC measurements the amorphous form formed with p-toluenesulfonic acid according to the invention only transforms into the crystalline form A at a temperature of around 120° C. This supports that the amorphous form is suitable for the production of pharmaceutical preparations. In other words the advantage of the invention is that the amorphous salt according to the invention is morphologically uniform and stable. Therefore, it is not expected to transform into another form in the pharmaceutical preparation, and the quality of the preparations, primarily its dissolution characteristics are not expected to change. The morphological uniformity is supported by the x-ray powder diffractogram of the novel salt, it confirms its uniform crystal structure and enables the identification of the form even in a pharmaceutical preparation, thereby making it possible to monitor the quality at a later time, and differentiate it from other crystalline polymorphous forms.

The advantage of another embodiment of the invention, the lumateperone naphthalene-2-sulfonic acid salt, preferably the formula (VIII) lumateperone salt, in which the molar ratio of lumateperone to the naphthalene-2-sulfonic acid salt is 1:2, is that as compared to the state of the art it satisfies a need that has existed for a long time, i.e. it provides a lumateperone active substance in solid form that can be produced at a good level of yield using methods that correspond to the demands of the pharmaceutical industry, without the use of a chiral chromatography purification step and that is suitable for the production of solid pharmaceutical preparations.

From another point of view the formula (VIII) lumateperone salt is preferable to the state of the art because it is crystalline, therefore the granule size can be easily made to correspond to the desired crystal fraction using crystallization methods according to the state of the art (by adjusting the speed of cooling in the case of crystallization, etc.). It is easier to handle as compared to amorphous active substances from the point of view of pharmaceutical technology. The reason for this is that amorphous substances are usually less stable. Furthermore, while amorphous substances are left to stand, optionally, during storage, or in the pharmaceutical preparation itself they partially or completely transform into a crystalline form or, optionally, into a mixture of several crystalline forms forming a morphologically inhomogeneous (non-uniform) active substance. As the solubility of the unstable amorphous compound usually differs from the solubility of the crystalline active substance, a change in morphological features may lead to a change in the effect of the preparation.

A further advantage of the formula (VIII) lumateperone salt is that the salt according to the invention is morphologically uniform and stable. Therefore, it is not expected to transform into another form in the pharmaceutical preparation, and the quality of the preparations, primarily its dissolution characteristics are not expected to change. The morphological uniformity is supported by the x-ray powder diffractogram of the novel salt and by its characteristic peaks, which confirm its uniform crystalline structure and enable the identification of the form even in the pharmaceutical preparation, thereby making it possible to monitor the quality at a later time, and differentiate it from other polymorphous forms.

A further advantage of the formula (VIII) lumateperone salt is that the formula (VIII) lumateperone salt, in which the molar ratio of lumateperone to the naphthalene-2-sulfonic acid salt is 1:2, is that it is formed at a high level of purity, essentially greater than 99% chemical purity when produced using the method described in the present invention, which enables it to be used directly in the pharmaceutical industry. This advantage originates from that by following the method according to the invention it becomes possible to produce and use the high-purity intermediate (II), with which the contaminants from the previous synthesis steps can be removed, as opposed to the 88% purity intermediate (II) used in the methods described in the state of the art.

A further advantage of the formula (VIII) lumateperone salt is that by using the resolution method according to the invention essentially distomer-free formula (VIII) lumateperone salt can be obtained via a high enantiomer-purity intermediate (II), in which salt the molar ratio of the formula (I) lumateperone and the naphthalene-2-sulfonic acid salt is 1:2.

A further advantage of the formula (VIII) lumateperone salt is that it can be produced using a method with which a product that has a level of enantiomer and chemical purity that enables its use directly in pharmaceutical preparations in a very easy way, from pure lumateperone using salt formation.

The formula (IX) lumateperone salt according to the present invention, in which formula the molar ratio of the formula (I) lumateperone and p-toluenesulfonic acid is 1:2, makes up for a deficiency that has existed for a long time, the ability to produce pharmaceutical preparations containing lumateperone on the industrial scale, i.e. the availability of pure solid active substance, the active substance content of which is greater than 97%, preferably greater than 99%, most preferably greater than 99.5%.

From another point of view the invention is preferable to the state of the art because the formula (IX) compound is crystalline, therefore the granule size can be easily transformed to the desired crystal fraction using crystallization methods according to the state of the art (by adjusting the speed of cooling in the case of crystallization, etc.). It is easier to handle as compared to amorphous active substances from the point of view of pharmaceutical technology. The reason for this is that amorphous substances are usually less chemically stable. Furthermore, while amorphous substances are left to stand, optionally, during storage, or in the pharmaceutical preparation itself they partially or completely transform into a crystalline form or, optionally, into a mixture of several crystalline forms forming a morphologically inhomogeneous (non-uniform) active substance. As the solubility of the unstable amorphous compound usually differs from the solubility of the crystalline active substance, a morphological change may lead to a change in the effect of the preparation. The morphological uniformity is supported by the x-ray powder diffractogram of the novel salt and by its characteristic peaks, which confirm its uniform crystalline structure and enable the identification of the form even in the pharmaceutical preparation, thereby making it possible to monitor the quality at a later time, and differentiate it from other polymorphous forms.

Figure 1:
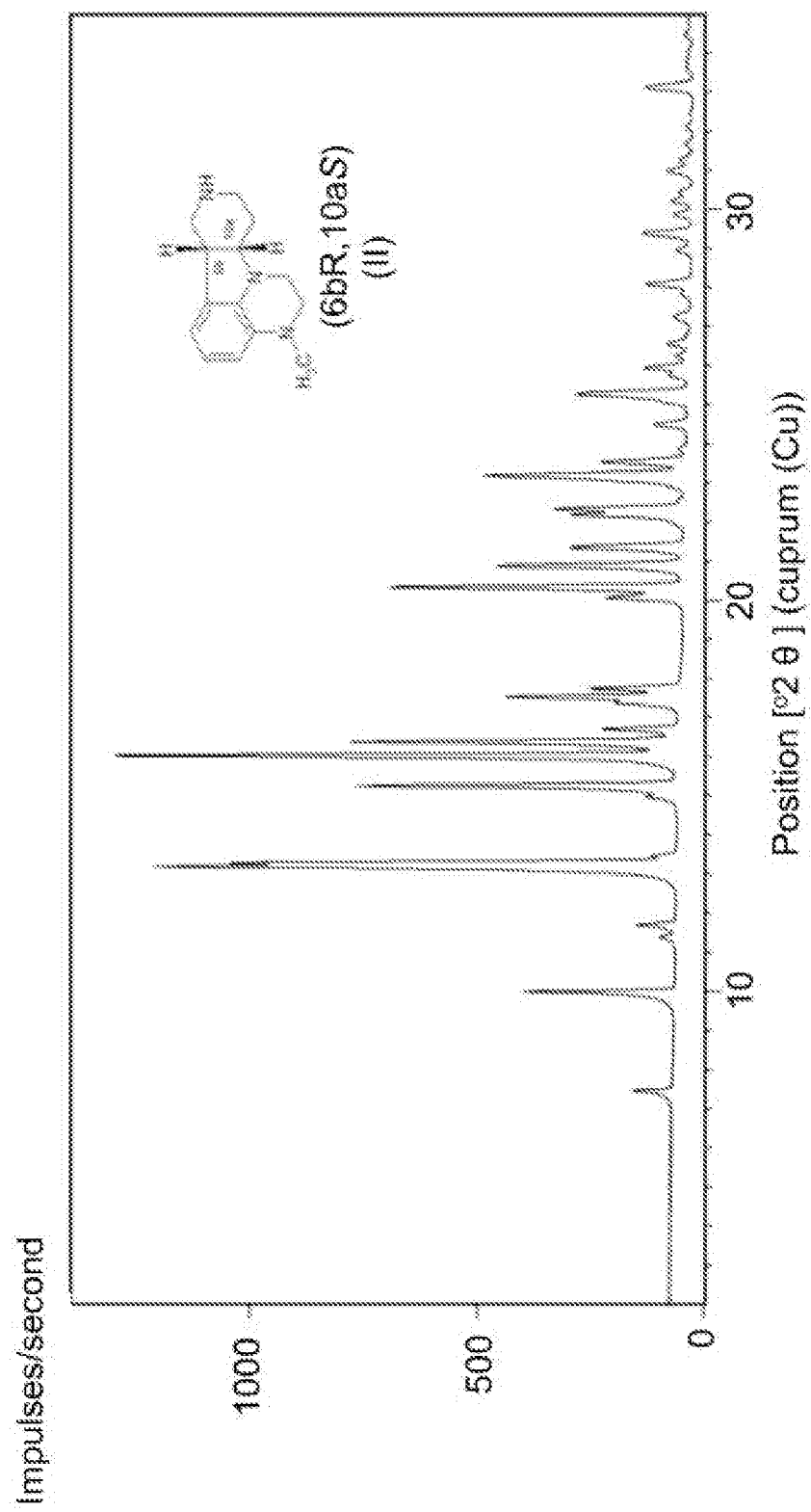
FIG. 1.) The x-ray powder diffractogram of the crystalline form of the formula (II) compound.
Figure 2:
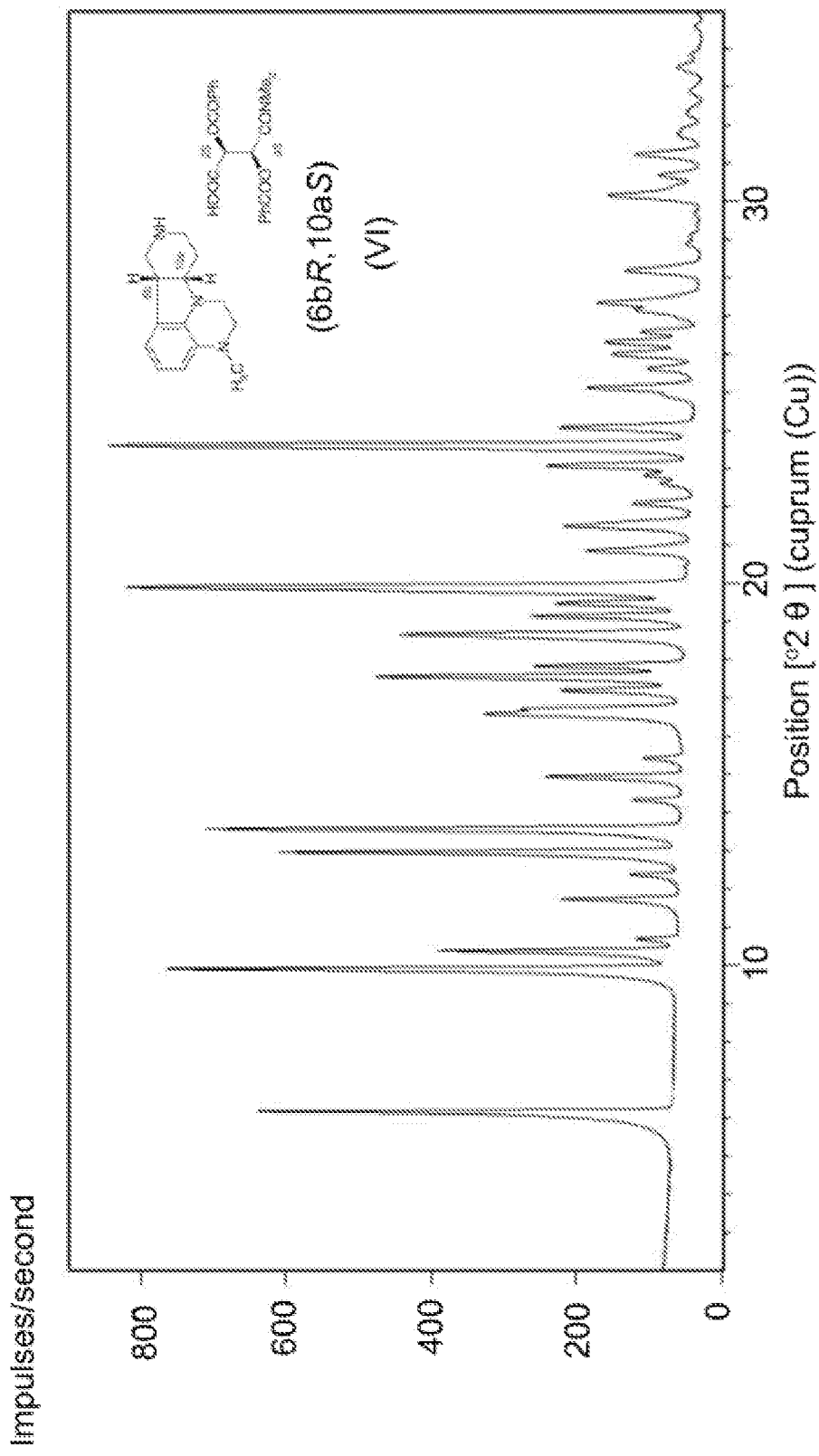
FIG. 2.) The x-ray powder diffractogram of the crystalline form of the formula (VI) salt.

The invention is presented via the following examples without restricting the scope of the patent application to these examples:

During the experiments the structures of the samples were confirmed with infrared (IR) spectra, with $^1$H-NMR, $^{13}$C-NMR measurements, and the crystal structure using x-ray powder diffractograms. The enantiomer purity was determined using chiral HPLC. The specific rotation of the intermediates and products confirmed to be pure was also determined. The rotation was measured using a Jasco P-2000 polarimeter. The melting points of the crystalline samples were determined using a Buchi B-540 melting point measurement device.

The IR-spectra were recorded using a Bruker Vector 22 FT spectrometer.

The $^1$H-NMR and the $^{13}$C-NMR recordings were made using Bruker Avance III HD and Bruker Avance III NMR devices.

The Thermogravimetric Measurement Conditions
   Device: TA Instruments Discovery TGA thermogravimetric analyser
   Atmosphere: flowing $N_2$: 25 m/min (furnace) 10 m/min (balance)
   Sampling frequency: 0.5 seconds/point
   Temperature program: 30° C.-250° C. 10° C./min
   Crucible: Platinum 100 µL
Differential Scanning Calorimeter Measurement Conditions
   Device: TA Instruments Discovery DSC differential scanning calorimeter
   Atmosphere: flowing $N_2$ (50 mL/min)
   Sampling frequency: 0.1 seconds/point
   Temperature program: 30° C.-230° C. 10° C./min
   Crucible: Standard Al closed
Differential Scanning Calorimeter (DSC)
(Conditions Prevailing in the Case of the Testing of the Formula III Amorphous Tosylate)
   Device: TA Instruments Discovery DSC differential scanning calorimeter
   Atmosphere: flowing $N_2$ (50 mL/min)
   Sampling frequency: 0.1 seconds/point
   Temperature program: 30° C.-190° C. 10° C./min
   Crucible: Standard Al open The x-ray powder recordings were made with the following instrument and measurement method:
   1.1 Device: PANalytical Empyrean X-ray powder diffractometer
   Measuring mode: Transmission
X-Ray Tube
   Type: Empyrean Long Fine Focus High Resolution tube
   Anode: Cu
   Wavelength: Kα (1.541874 Å)
   Focus: line focus
Source Side Optical Elements
   Divergence slit: Fixed slit ½°
   Mirror: Elliptical focussing mirror
   Soller slit: 0.04 rad
   Diffusion inhibitor slit: Fixed slit ½°
Diffracted Side Optical Elements
   Diffusion inhibitor slit: Programmable slit in fixed mode: ½°
   Soller slit: 0.04 rad
Sample Table
   Type: Reflection-transmission, with rotatable sample holders
   Sample rotation speed: 1 rps
   Direct ray blocker
   ("beam knife"): Transmission
Detector
   Type: PIXcel 3D 1×1 area detector
   Detecting mode: Scanning line detector (1D) mode
   Active detector window
   size: 3.3473°
   Sample preparation: The unpowdered samples are placed between two Mylar sheets.
Measurement Conditions
   Temperature: room temperature
   Accelerating voltage: 45 kV
   Anode heating current: 40 mA
   Scanning mode: continuous (θ/θ) scanning
   Measurement range: 2.0000-34.9964°2θ
   Step gap: 0.0131°2θ
   Step duration: 109.650 s
   Number of measurement cycles: 1
   Measurement time: ~20 min
Chiral HPLC Method:
   The methods used to test the formula (II) and (IV) compounds:
   Device: Agilent 1100
   Column: Lux Amylose-2.5 µm, 150 mm×4.6 mm
   Eluent: ethanol/ethanolamine=100/0.1
   Flow rate: 0.6 ml/min
   Temperature: 25° C.
   Detection: DAD 230 nm
   Retention times: II (6bR,10aS): 11.5 min, II/A (6bS, 10aR): 6.0 min
   The chiral HPLC method used to test the lumateperone and its salts (formula (I), (III) and (VIII) compounds):
   Device: HP 1100
   Column: Lux Amylose-2.5 µm, 150 mm×4.6 mm
   Eluent: ethanol/acetonitrile/diethylamine=85/15/0.1
   Flow rate: 0.3 ml/min
   Temperature: 25° C.
   Detection: DAD 232 nm
   Retention times: eutomer (6bR,10aS): 9.5 min, distomer (6bS,10aR): 11.0 min.

EXAMPLE 1

The Formula (VI) Salt of (6bR,10aS)-3-methyl-2,3, 6b,9,10,10a-hexahydro-1H-pyrido[3',4': 4,5]pyrrolo[1,2,3-de]quinoxaline formed with (+)-dibenzoyl-D-tartaric acid mono(dimethylamide)

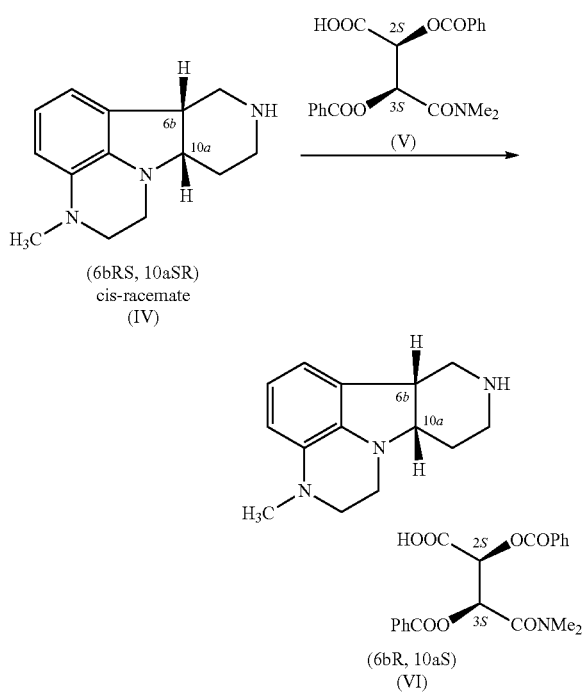

34.40 g (150 mmol) formula (IV) cis racemate is dissolved in 100 ml methanol in a flask rinsed with argon. Over the course of approx. 1 minute a solution of (+)-dibenzoyl-D-tartaric acid mono(dimethylamide) (40.47 g, 105 mmol) made with 150 ml methanol is poured into the yellow solution stirred at room temperature. Crystallization starts from the bright yellow solution within a few minutes. The yellow suspension is stirred for a further 3 hours in an argon atmosphere at room temperature. The precipitated crystalline material is filtered, washed with methanol (80 ml) then dried at room temperature. The 43.65 g of yellow crystalline material obtained in this way is suspended in methanol (1200 ml) in an argon atmosphere and boiled. Further methanol (220 ml) is added until full dissolution. The hot solution is left to cool to room temperature, then stirred for a further 17 hours. The precipitated crystalline material is filtered, then washed with methanol (40 ml) and with ether (30 ml), in this way 31.98 g (35%, 69% calculated for the eutomer cis compound) formula (VI) compound is obtained. According to chiral HPLC measurement the product obtained contains 99.82% formula (VI) compound, 0.04% diastereomer salt and a further 3 contaminants (0.14% in total).

Mp: 203-207° C. (decomposes).

$[\alpha]_D^{25}$=+28 (c=0.40, methanol)

IR (KBr): 3583, 3420, 3066, 2617, 1720, 1672, 1652, 1111, 717 cm$^{-1}$.

$^1$H-NMR (DMSO-d$_6$, 600 MHz): 9.38 (b, 2H), 7.97 (m, 2H), 7.97 (m, 2H), 7.66 (m, 1H), 7.64 (m, 1H), 7.53 (m, 2H), 7.52 (m, 2H), 6.55 (m, 1H), 6.39 (m, 1H), 6.38 (m, 1H), 6.10 (d, J=3.6 Hz, 1H), 5.49 (d, J=3.5 Hz, 1H), 3.43 (m, 1H), 3.34 (m, 1H), 3.28 (m, 1H), 3.17 (m, 1H), 3.17 (m, 1H), 3.16 (s, 3H), 3.08 (m, 1H), 3.07 (m, 1H), 2.83 (m, 1H), 2.79 (s, 3H), 2.79 (s, 3H), 2.63 (m, 1H), 2.41 (m, 1H), 1.99 (m, 1H), 1.92 (m, 1H) ppm.

$^{13}$C-NMR (DMSO-d$_6$, 150 MHz): 167.88; 166.32; 165.37; 165.31; 137.52; 135.32; 133.79; 133.35; 130.42; 129.54; 129.49; 128.97; 128.81; 127.64; 120.59; 112.56; 109.35; 72.77; 72.10; 62.88; 49.97; 44.48; 43.83; 38.85; 37.79; 37.20; 36.66; 35.62; 21.15 ppm.

EXAMPLE 2

The Production of Lumateperone (I) from (VI)

(Method 1)

6.15 g (10 mmol) formula (VI) compound is dissolved in 20 ml 5% NaOH solution and then the solution is extracted with toluene (20 ml, 2×15 ml). The unified toluene phase is dehydrated using azeotropic distillation. 3.01 g (15 mmol) 4-chloro-4'-fluoro butyrophenone, 5.86 ml (42.5 mmol) triethylamine and 2.49 g (15 mmol) dried potassium iodide is added to the 20 ml toluene solution obtained in this way. The reaction mixture is boiled for 14 hours in an argon atmosphere, then cooled and filtered. The filtrate is extracted with 10 ml water and 10 ml conc. NaCl solution, dried over Na$_2$SO$_4$, filtered and evaporated. The residue to cleaned with flash chromatography on silica gel with a CH$_2$Cl$_2$—MeOH eluent. 2.68 g (68%) lumateperone (brown oil) is obtained.

$[\alpha]_D^{24}$=−36.8 (c=0.853, CHCl$_3$).

IR (film): 1737, 1686, 1616, 1597, 1504, 1326, 1156 cm$^{-1}$.

$^1$H-NMR (CDCl$_3$, 400 MHz): 8.00 (~dd, J$_1$=5.5 Hz, J$_2$=8.9 Hz, 2H), 7.12 (~t, J=8.7 Hz, 2H), 6.64 (m, 1H), 6.51 (m, 1H), 6.40 (m, 1H), 3.59 (m, 1H), 3.30 (m, 1H), 3.26 (m, 1H), 3.19 (m, 1H), 3.08 (m, 1H), 2.98 (t, J=7.2 Hz, 2H), 2.86 (s, 3H), 2.84 (m, 1H), 2.82 (m, 1H), 2.65 (m, 1H), 2.39 (m, 2H), 2.24 (m, 1H), 1.98 (m, 1H), 1.95 (m, 2H), 1.89 (m, 1H), 1.82 (m, 1H) ppm.

EXAMPLE 3

The Production of Lumateperone (I) from (VI)

(Method 2) 922 mg (1.5 mmol) formula (VI) salt is suspended in 20 ml toluene. 0.88 ml triethylamine (6.3 mmol), 0.375 g potassium iodide (2.25 mmol) and 0.45 g (2.25 mmol) 4-chloro-4'-fluoro butyrophenone is added to it. It is then boiled in an argon atmosphere for 14 hours, the cooled reaction mixture is filtered. The filtrate is extracted with 1×10 ml water and 1×10 ml saturated NaCl solution, dried on sodium sulphate, filtered and evaporated. The raw product obtained is cleaned using flash chromatography, 0.20 g (34%) lumateperone (brown oil) is obtained.

EXAMPLE 4.a

The Formula (II)·2HCl Salt of Formula (II) (6bR, 10aS)-3-methyl-2,3,6b,9,10,10a-hexahydro-1H-pyrido[3',4': 4,5]pyrrolo[1,2,3-de]quinoxaline

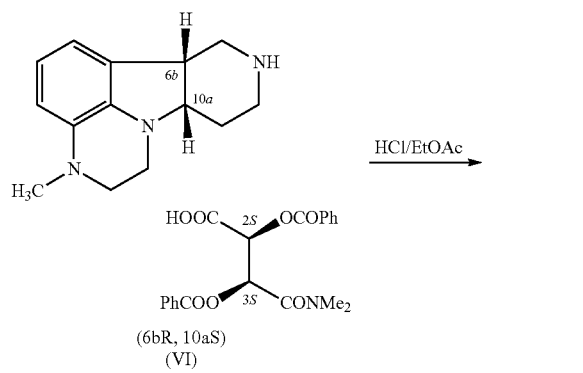

(6bR, 10aS)
(VI)

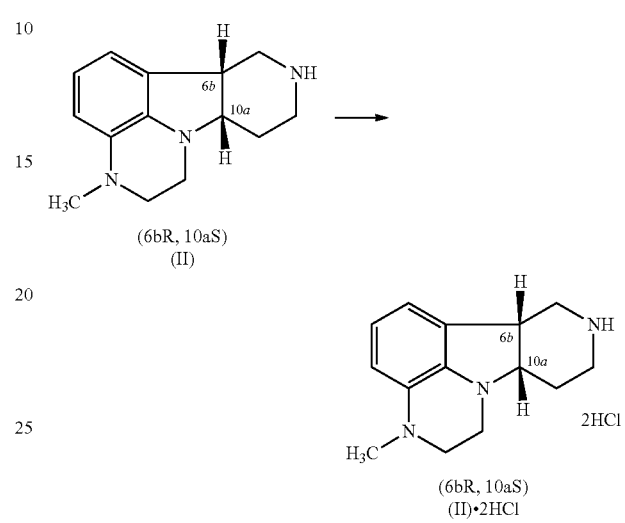

(6bR, 10aS)
(II)·2HCl 18.44 g (30 mmol) formula (VI) salt is suspended in 180 ml ethyl acetate, then 53.5 ml 1.4 mol hydrochloric acid ethyl acetate solution (2.73 g HCl, 75 mmol) is added to the yellow suspension stirred in a 25° C. water bath in an argon atmosphere. Following this the suspension is stirred for 1 hour, in an argon atmosphere at room temperature. The precipitated product is filtered, washed with ethyl acetate (30 ml), dried in the air at room temperature for 1.5 hours, thereby 8.97 g (98.9%) bone coloured powder is obtained.

According to chiral HPLC measurement the product contains 99.83% formula (II)·2HCl compound, 0.06% (6bS, 10aR) absolute configuration enantiomer and one further contaminant (0.12%).

$^1$H-NMR (DMSO-$d_6$, 600 MHz): 9.54 (b, 1H), 9.31 (b, 1H), 6.83 (b, 3H), 3.3-3.7 (bm, 6H), 3.17 (bm, 1H), 3.11 (bm, 1H), 2.95 (b, 4H), 2.58 (bm, 1H), 2.17 (bm, 2H) ppm.

EXAMPLE 4.b

The Production of the Formula (II)·2HCl (6bR, 10aS)-3-methyl-2,3,6b,9,10,10a-hexahydro-1H-pyrido[3',4': 4,5]pyrrolo[1,2,3-de]quinoxaline dihydrochloride Salt from the Formula (II) Base 631 mg (2.75 mmol) enantiomer-pure base (II) is dissolved in 5 ml ethyl acetate, the airspace above the solution is rinsed with argon. 5.0 ml 1.4 M hydrochloric acid ethyl acetate (7 mmol HCl, 2.54 equiv.) is added drop by drop to the tape water-cooled, intensively stirred yellow solution. The precipitation of the product starts immediately. The thick off white suspension is stirred for 1 hour at room temperature in an argon atmosphere. The product is filtered, and washed with a little ethyl acetate (1.5 ml+1 ml). After vacuum drying at room temperature 825 mg (99%) formula (II)·2HCl light grey crystalline dihydrochloride salt is obtained.

mp 199-203° C. (decomposes)
$[\alpha]_D^{25}$=+51 (c=0.40, methanol).
IR (KBr): 3058, 1964, 1420, 1128, 756 cm$^{-1}$.
$^1$H-NMR (DMSO-$d_6$, 600 MHz): 9.54 (b, 1H), 9.31 (b, 1H), 6.83 (b, 3H), 3.3-3.7 (bm, 6H), 3.17 (bm, 1H), 3.11 (bm, 1H), 2.95 (b, 4H), 2.58 (bm, 1H), 2.17 (bm, 2H).
Element analysis: calculated C 55.64; H 7.00; N 13.90; Cl 23.46%; measured C 55.40; H 7.06; N 13.81; Cl 23.48%.

EXAMPLE 5

The Production of Formula (I) Lumateperone from (II)·2HCl 1.82 g (6.0 mmol) formula (II)·2HCl substance is suspended in 20 ml toluene, then 1.81 g (9.0 mmol) 4-chloro-4'-fluoro butyrophenone, 5.04 ml (36.1 mmol) triethylamine and 1.50 g (9.0 mmol) dried potassium iodide are added to it. The suspension reaction mixture is then boiled for 14 hours in an argon atmosphere. After cooling the reaction mixture is filtered and the filtered out solid material is washed with toluene. The organic phase is extracted with 20 ml water, then with 20 ml saturated NaCl solution, dried over MgSO$_4$, filtered and evaporated. The raw product obtained is cleaned on silica gel using flash chromatography

EXAMPLE 6

The Production of Formula (II) (6bR,10aS)-3-methyl-2,3,6b,9,10,10a-hexahydro-1H-pyrido[3',4':4,5]pyrrolo[1,2,3-de]quinoxaline Crystalline Base from the Formula (VI) Salt

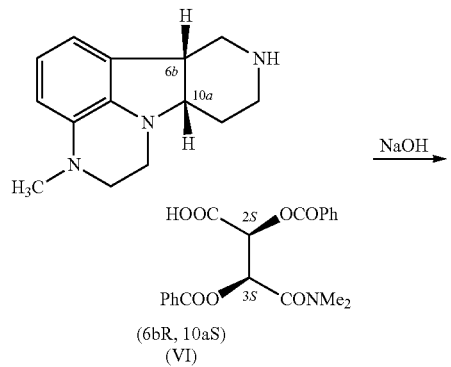

Method A 4 ml 5 m/m % aqueous sodium hydroxide solution (200 mg NaOH, 5 mmol) is added drop by drop to an aqueous suspension of 1.23 g (2.0 mmol) formula (VI) salt (10 ml). The alkaline yellow solution is extracted with 3×15 ml toluene. The combined organic phase is dried ($Na_2SO_4$), then evaporated until dry in a vacuum, thereby with quantitative yield the formula (II) compound is obtained. Mp: 79-81° C. (diisopropyl ether).

Chiral HPLC: 99.31% (II)+0.08% (II/A) (+3 contaminants, total 0.61%)

EXAMPLE 7

The Production of Formula (II) (6bR,10aS)-3-methyl-2,3,6b,9,10,10a-hexahydro-1H-pyrido[3',4':4,5]pyrrolo[1,2,3-de]quinoxaline Crystalline Base from the Formula (VI) Salt Method B 4 ml 5 m/m % aqueous sodium hydroxide solution (200 mg NaOH, 5 mmol) is added drop by drop to an aqueous suspension of 1.23 g (2.0 mmol) formula (VI) salt (10 ml). The alkaline yellow solution is extracted with 3×15 ml ethyl acetate. The combined organic phase is dried ($Na_2SO_4$), then evaporated until dry in a vacuum, thereby with quantitative yield the formula (II) compound is obtained. Mp: 79-81° C. (diisopropyl ether).

EXAMPLE 8

The Production of Formula (II) (6bR,10aS)-3-methyl-2,3,6b,9,10,10a-hexahydro-1H-pyrido[3',4':4,5]pyrrolo[1,2,3-de]quinoxaline Crystalline Base from its Formula (II)·2HCl salt

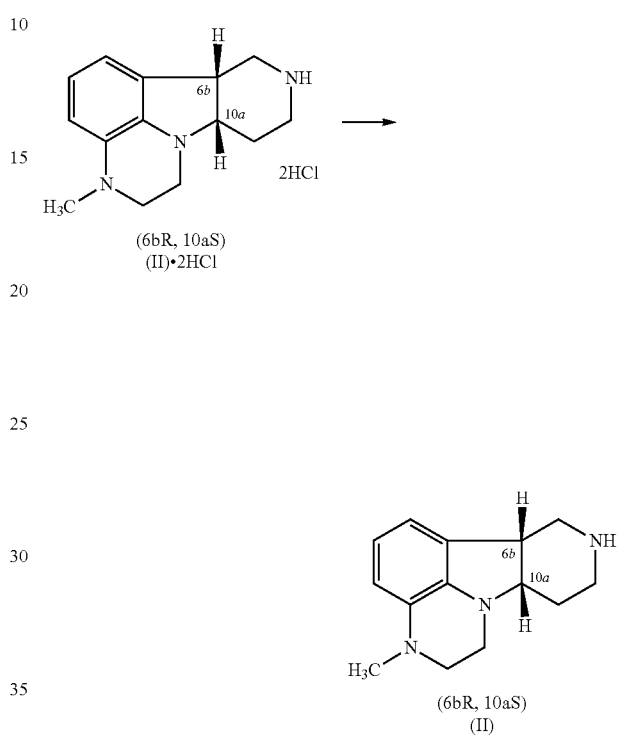

8.46 g (28 mmol) formula (II)·2HCl compound is dissolved in 40 ml distilled water and to the solution at 20° C. 27.5 ml concentrated aqueous ammonia solution (24.7 g 25 m/m % solutions, 6.19 g ammonia, 364 mmol) is added to it drop by drop over a few minutes. Precipitation occurs immediately. The oily product precipitating from the strong alkaline solution (pH>12) is extracted with toluene (2×50 ml, then 30 ml). The combined toluene phases are evaporated in a vacuum. The residue is 6.95 g light brown oil, which crystalizes from diisopropyl ether (12 ml). In this way 4.86 g (76%) off-white crystalline material is obtained.

According to chiral HPLC measurement the product contains 99.85% formula (II) compound and a further two contaminants (a total of 0.15%). (6bS,10aR) absolute configuration enantiomer contamination (II/A) could not be detected.

Mp: 79-81° C.

$[\alpha]_D^{25}=-132$ (c=0.40, methanol).

IR (KBr): 3329, 1614, 1503, 1326, 730 $cm^{-1}$.

$^1$H-NMR (CDCl$_3$, 400 MHz): 6.65 (m, 1H), 6.51 (m, 1H), 6.41 (m, 1H), 3.59 (m, 1H), 3.33 (m, 1H), 3.30 (m, 1H), 3.28 (m, 1H), 3.06 (m, 1H), 3.01 (m, 1H), 2.87 (s, 3H), 2.84 (m, 1H), 2.83 (m, 2H), 2.64 (m, 1H), 1.88 (m, 1H), 1.77 (m, 1H) ppm.

$^{13}$C-NMR (CDCl$_3$, 100 MHz): 138.06; 134.98; 120.94; 120.13; 112.67; 108.80; 64.81; 50.59; 48.93; 44.07; 41.80; 41.78; 37.54; 25.70 ppm.

EXAMPLE 9

Figure 3:
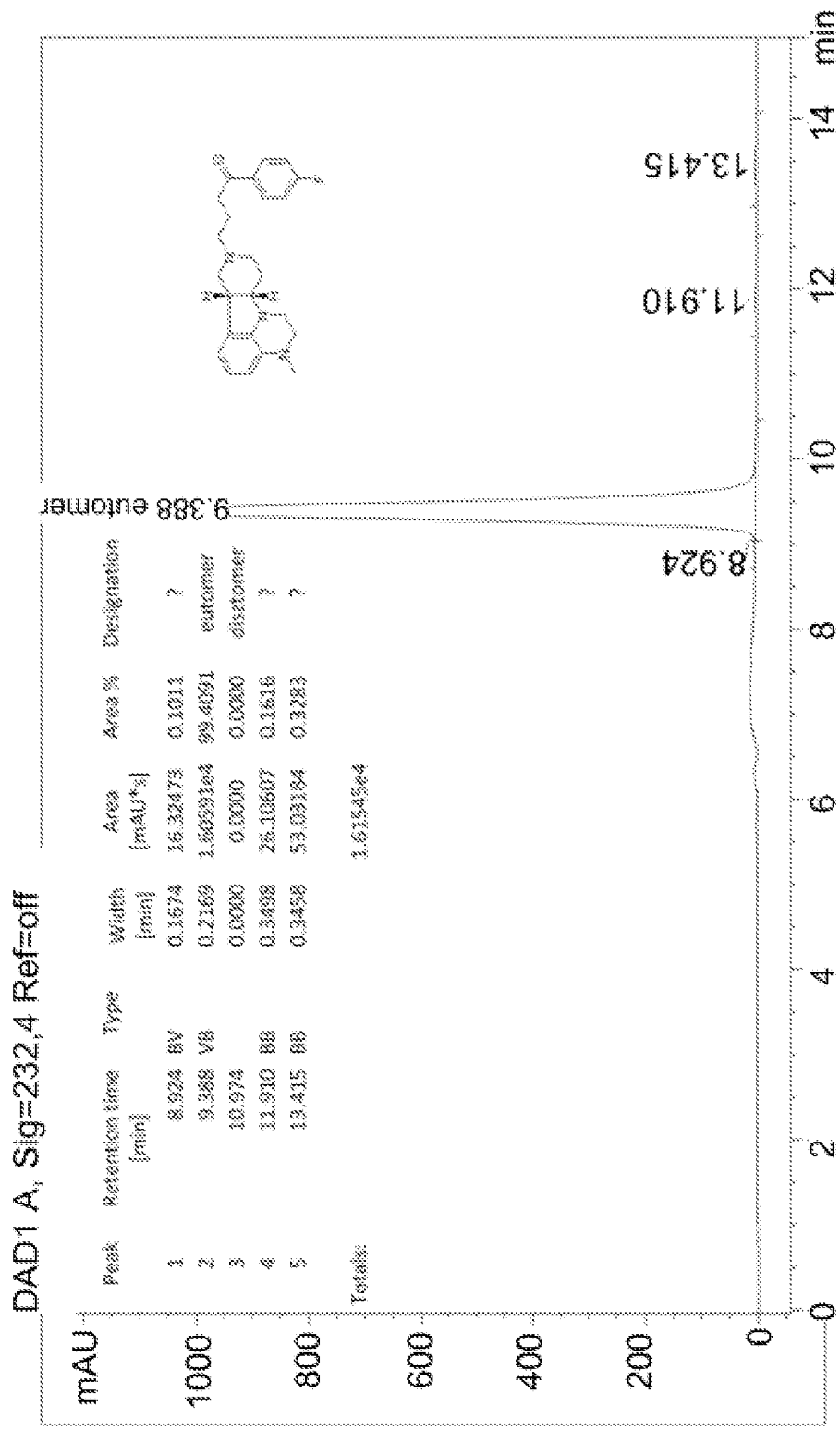
FIG. 3.) The chiral HPLC chromatogram of the lumateperone base produced according to example 9 of the invention.

The Production of the Formula (I) Lumateperone from the Formula (II) (6bR,10aS)-3-methyl-2,3,6b,9,10,10a-hexahydro-1H-pyrido[3',4': 4,5]pyrrolo[1,2,3-de]quinoxaline Method A 4.58 g (20 mmol) formula (II) compound is dissolved in 50 ml toluene, to which 6.02 g (30 mmol) 4-chloro-4'-fluoro butyrophenone, 11.72 ml (84 mmol) triethylamine and 4.98 g (30 mmol) dried potassium iodide is added. The suspension reaction mixture is boiled for 14 hours in an argon atmosphere. After cooling it is filtered, and the filtered out solid substance is washed with toluene. The organic phase is extracted with 25 ml water, then with 25 ml saturated NaCl solution, dried on $MgSO_4$, filtered and evaporated. The raw product obtained is cleaned on silica gel using flash chromatography using a dichloromethane-methanol eluent. 5.58 g (71%) formula (I) substance is obtained (light brown oil). The purity of the product measured with chiral HPLC is 99.41%, contaminants: distomer: 0,000%, other contaminants (3 contaminants): 0.10%; 0.16% and 0.32%. (FIG. 3)

EXAMPLE 10

The Production of the Formula (I) Lumateperone from the Formula (II) (6bR,10aS)-3-methyl-2,3,6b,9,10,10a-hexahydro-1H-pyrido[3',4': 4,5]pyrrolo[1,2,3-de]quinoxaline Method B 0.459 g (2.0 mmol) formula (II) compound is dissolved in 15 ml acetonitrile, then, to this, 1.303 g (4.0 mmol) caesium carbonate and 0.876 g (3.0 mmol) 4-iodo-4'-fluoro butyrophenone is added. The reaction mixture is stirred for 24 hours at room temperature. Then it is filtered and evaporated. The evaporation residue is dissolved in 20 ml dichloromethane and then extracted with 10 ml water, than with 10 ml saturated NaCl solution. The organic phase is dried on $Na_2SO_4$, filtered and evaporated. The 1.06 g raw product obtained is cleaned on silica gel with flash chromatography using $CH_2Cl_2$—MeOH as eluent. 0.66 g (84%) formula (I) compound is obtained (light brown oil).

EXAMPLE 11

The Production of Formula (II) (6bR,10aS)-3-methyl-2,3,6b,9,10,10a-hexahydro-1H-pyrido[3',4': 4,5]pyrrolo[1,2,3-de]quinoxaline Crystalline Base from the Formula (IV) Racemic Cis Compound with a Two-Step Resolution Process Step A The Separation of the Formula (VI/A) L-DBMA Salt from the Formula (IV) Racemic Cis Compound 2.29 g (10 mmol) cis racemate is dissolved in 12 ml methanol. A thin stream of a colourless solution of 2.70 g (7 mmol, 0.7 equiv.) (−)-dibenzoyl-L-tartaric acid mono(dimethylamide) (L-DBMA) made with 13 ml methanol is poured into the brownish solution stirred in an argon atmosphere in a 25° C. water bath, the Erlenmeyer flask is rinsed with a further 2 ml methanol. After 2 minutes the yellow solution starts to become cloudy, and after another 1 minute a thick yellow suspension is obtained, which is then stirred for 3 hours in an argon atmosphere at room temperature. The precipitated product is filtered, then washed with methanol (5+2.5 ml) and diethyl ether (2×3 ml). The raw product dries to constant weight in 1 hour in air.

The distomer raw product: 2.717 g light yellow powder, mp 210-213° C. (decomposes) (yield: 88.5%, theoretical yield: 3.07 g, 5 mmol)

chiral HPLC: 98.26% (VI/A)+1.39% (VI) (+2 contaminants, total 0.35%)

Step B

The Purification Step of the Methanol Mother Liquor, in the Course of which the Excess L-DBMA is Removed.

The methanol mother liquor formed in the resolution step A is evaporated in a vacuum.

The 2.60 g oily residue is dissolved in 20 ml toluene, then the brown solution is washed with 10 ml 5 m/m % aqueous NaOH solution. The aqueous phase (pH=14) is washed with 2×10 ml toluene, then the combined organic phases are evaporated in a vacuum. 1.48 g brown oily residue is obtained.

Step C

The isolation of the formula (VI) D-DBMA salt from an approx. 10:1 ratio (II)/(II/A) base mixture The 1.48 g oily extract obtained in step B (approx. 10:1(11)/(II/A) isomer mixture) is dissolved in 6 ml methanol. A thin stream of a colourless solution of 1.93 g (5 mmol, appr. 0.91 equiv.) (+)-dibenzoyl-D-tartaric acid mono(dimethylamide) (D-DBMA) made with 8 ml methanol is poured into the brownish solution stirred in an argon atmosphere in a 25° C. water bath, with a further 2 ml methanol the residue is rinsed from the Erlenmeyer flask. The precipitation of the product starts immediately resulting in a thick yellow suspension, which is then stirred for 3 hours at room temperature in an argon atmosphere. The precipitated product is filtered, then washed with methanol (5+2.5 ml) and diethyl ether (2×3 ml). The raw product dries to constant weight in 10 minutes in air.

The formula (VI) raw product: 2.785 g light yellow powder, mp (192-) 204-207° C. (decomposes), (yield: 90.7%) (theoretical yield: 3.07 g, 5 mmol)

chiral HPLC: 98.98% (VI)+0.71% (VI/A) (+3 contaminants, total 0.31%)

2.65 g eutomer raw product is recrystallized from 100 ml methanol in an argon atmosphere. The thin yellow suspension cooled to room temperature is stirred at room temperature in an argon atmosphere for 16 hours. The precipitated product is filtered, washed with methanol (5+3 ml), and then with diethyl ether (2×5 ml). The product dries to constant weight in 1 hour in the air.

The formula (VI) product: 1.837 g light yellow crystals, mp 203-209° C. (decomposes) chiral HPLC: 99.74% (VI)+ 0.00% distomer (VI/A) (+2 contaminants, total 0.26%)

EXAMPLE 12

The Production of the Lumateperone (I)p-Toluenesulfonic Acid Salt Polymorph "A"

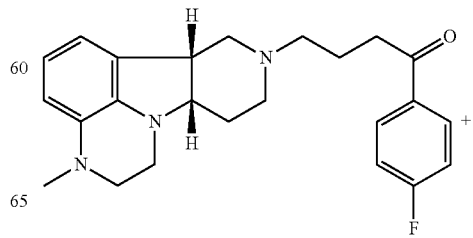

-continued

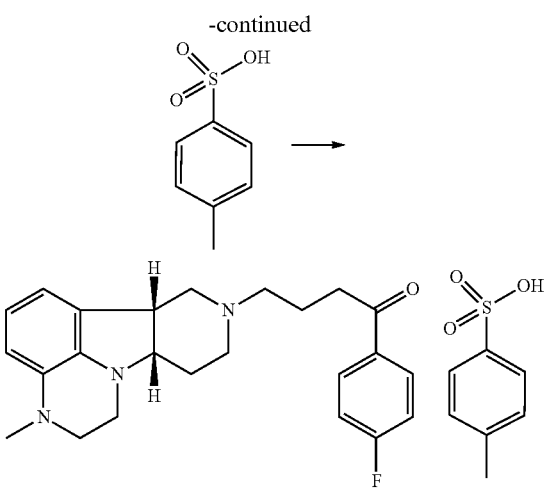

The production of the lumateperone monotosylate salt (on the basis of WO2009/114181 patent example A2)

The 2.75 g (7.0 mmol) formula (I) lumateperone base produced according to example 9 is dissolved in 20 ml 2-propanol, then 1.20 g (6.3 mmol, 0.9 equiv.) p-toluenesulfonic acid monohydrate dissolved in 9 ml 2-propanol is added to this in one portion at room temperature in an argon atmosphere. If crystallization does not start even after 15 minutes, then the solution is seeded with the previously produced lumateperone monotosylate salt. After the crystals have precipitated the solution is stirred for another 24 hours at room temperature. (after 1-2 hours with filtration it was not usually possible to obtain 1:1 ratio tosylate salt.) After the one day of stirring the white crystalline material is filtered, washed with a little 2-propanol, then dried over $P_2O_5$ until constant weight at 40° C. 3.20 g white crystalline material is obtained, 78% yield. White crystalline substances, not a solvate and not a hydrate. Melting point 181-184° C. (2-propanol). $[\alpha]D^{24}=-10.6$ (c=1.00, acetone). According to XRPD polymorph "A" (identified according to WO2009/114181 A2).

IR (KBr): 2611, 1687, 1598, 1508, 1325, 1228, 1159, 1010, 683 cm$^{-1}$.

$^1$H-NMR (DMSO-d$_6$, 400 MHz): 9.18/9,42 (b, 1H), 8.04 (~dd, J$_1$=5.6 Hz, J$_2$=8.8 Hz, 2H), 7.50 (~d, J=8.1 Hz, 2H), 7.36 (~t, J=8.8 Hz, 2H), 7.11 (~d, J=8.0 Hz, 2H), 6.60 (m, 1H), 6.51 (m, 1H), 6.42 (m, 1H), 3.58 (m, 1H), 3.46 (m, 1H), 3.45 (m, 1H), 3.40 (m, 1H), 3.33 (m, 1H), 3.31 (m, 1H), 3.20 (m, 1H), 3.12 (m, 2H), 3.11 (t, J=7.0 Hz, 2H), 3.03 (m, 1H), 2.81 (s, 3H), 2.56 (m, 1H), 2.27 (s, 3H), 2.23 (m, 1H), 2.12 (m, 1H), 2.01 (m, 2H) ppm.

$^{13}$C-NMR (DMSO-d$_6$, 100 MHz): 197.36; 165.24 (d, J=251.6 Hz); 145.58; 138.00; 137.47; 135.37; 133.28 (d, J=2.7 Hz); 131.07 (d, J=9.5 Hz); 128.30; 126.92; 125.65; 120.76; 115.89 (d, J=22.0 Hz); 112.68; 109.52; 62.38; 55.73; 52.71; 49.97; 47.92; 43.91; 38.71; 37.17; 35.07; 21.85; 20.93; 18.19 ppm.

Element analysis: calculated C: 65.82%, H: 6.41%, N: 7.43%, S: 5.64%. Measured C: 65.67%, H: 6.29%, N: 7.54%, S: 5.93%.

Figure 4:
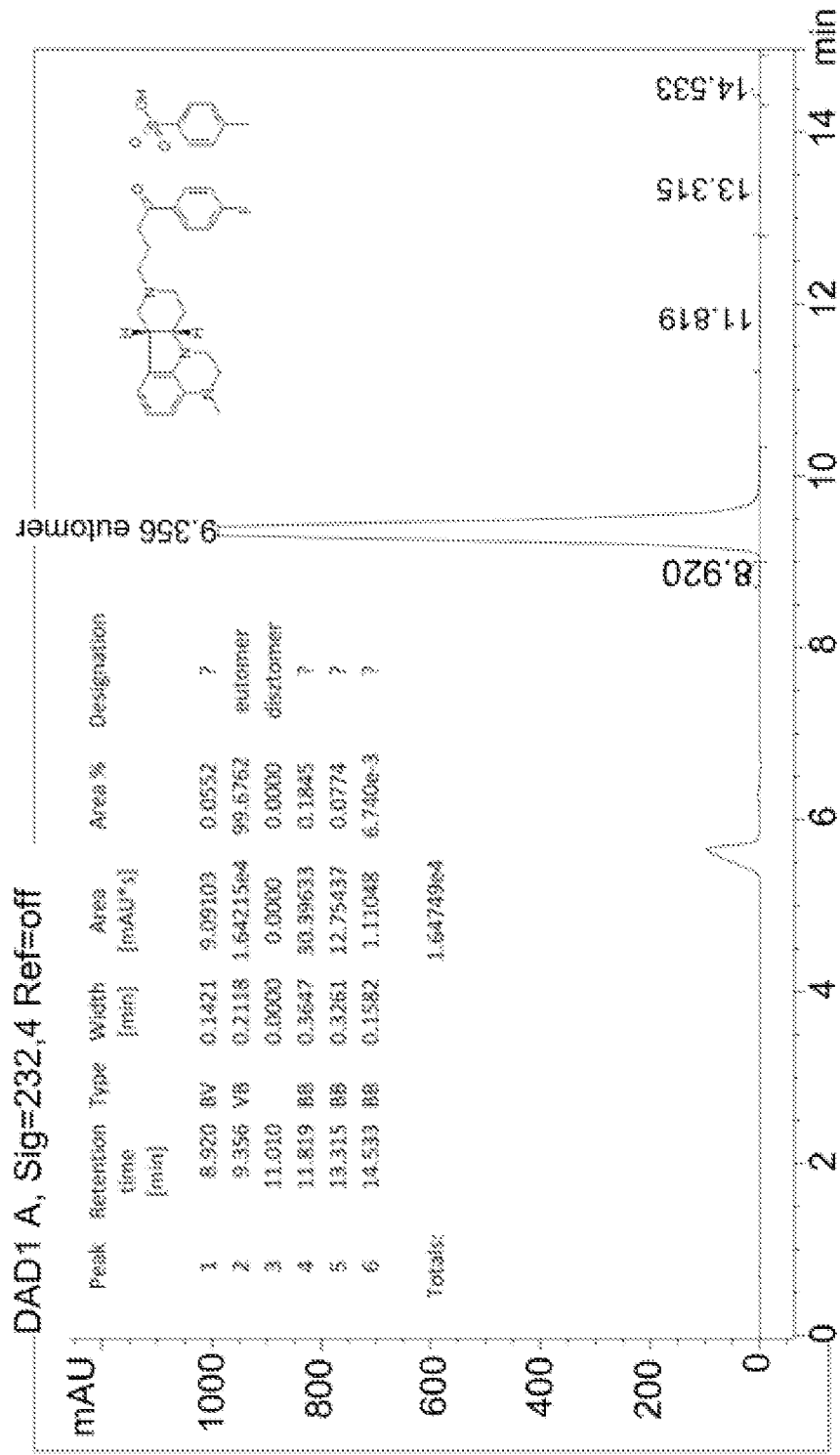
FIG. 4.) The chiral HPLC chromatogram of the lumateperone tosylate produced according to example 12 of the invention.
Figure 5:
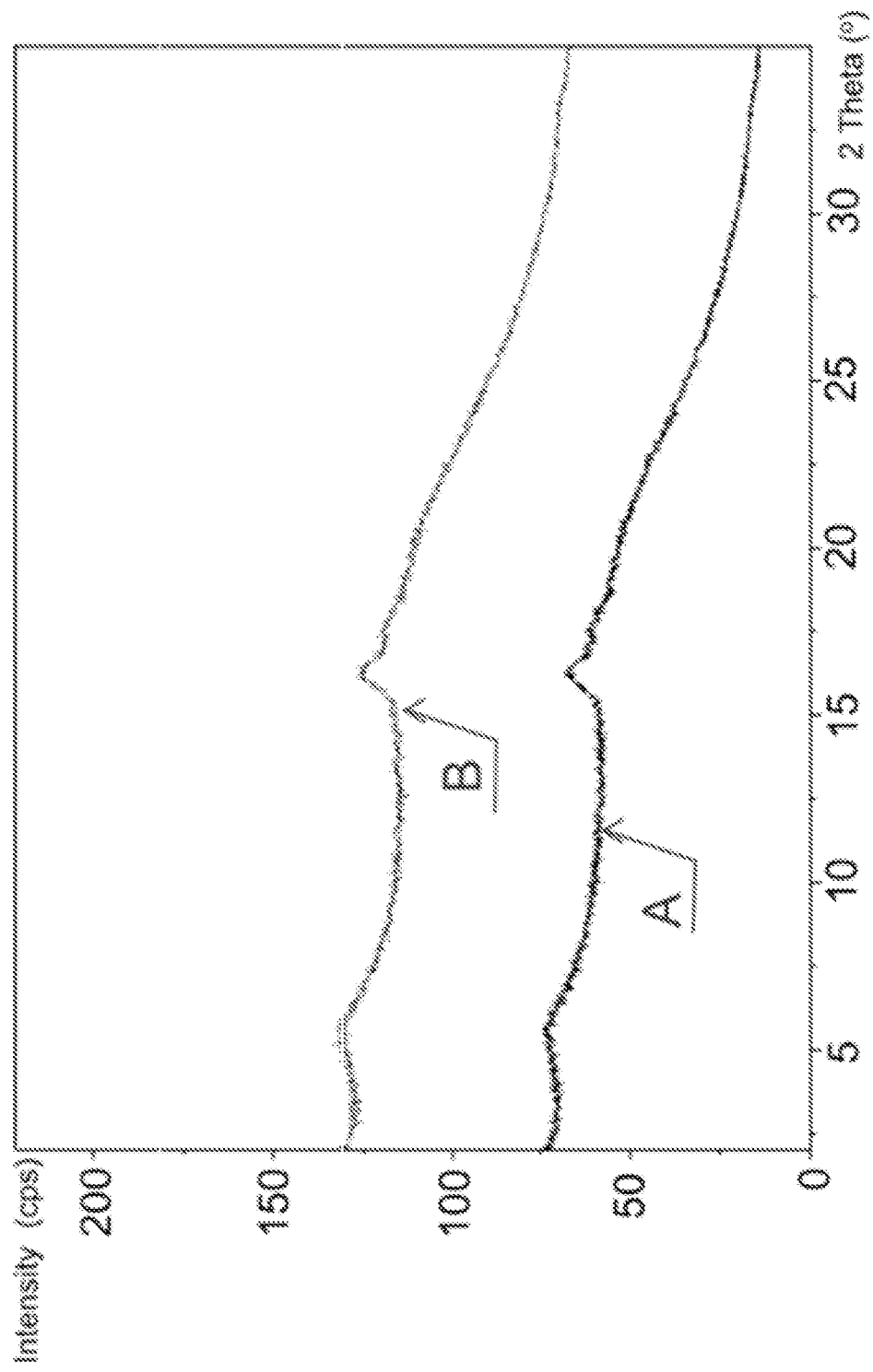
FIG. 5.) The x-ray powder diffractograms of the formula (III) amorphous salt produced according to example 13, where curve "A" is the XRD curve of the finished product after manufacture, while curve "B" shows the XRD curve, with displacement, after 3 months of storage at room temperature in a sealed vessel.
Figure 6:
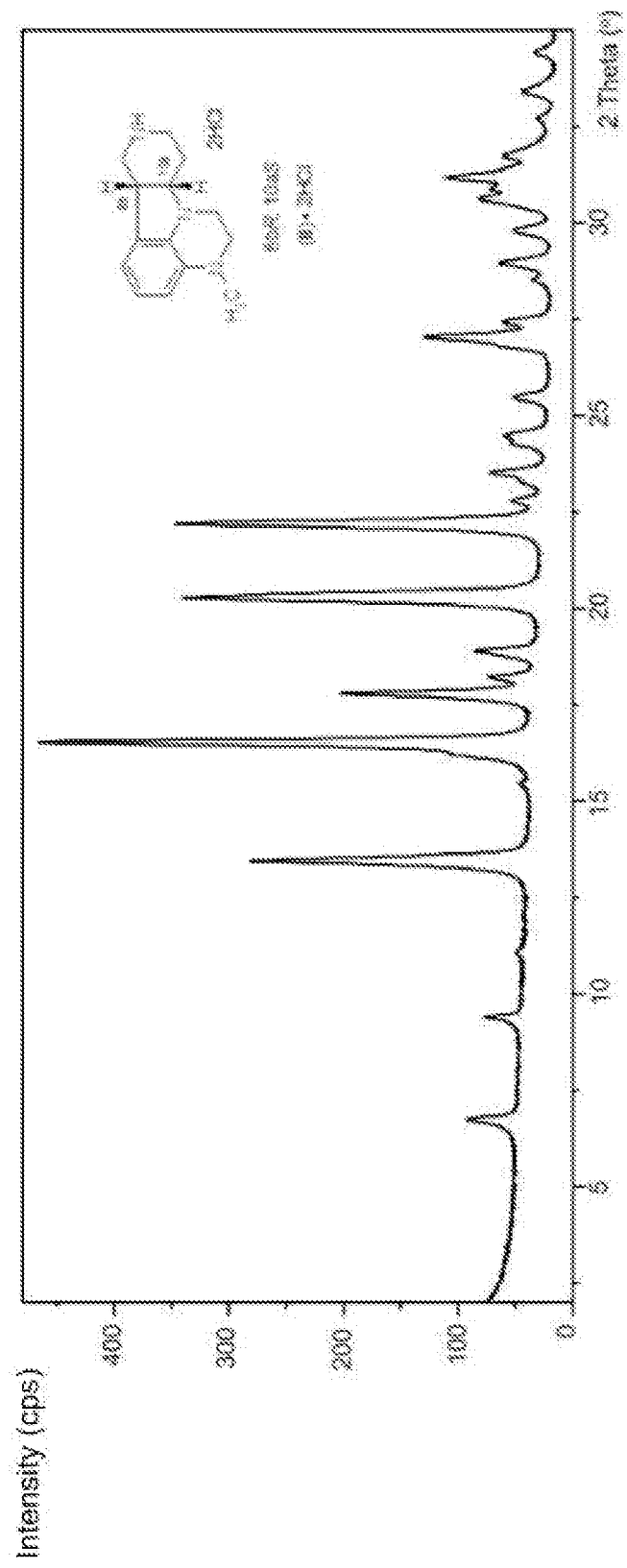
FIG. 6.) The XRD curve of the formula (II)·2HCl compound produced according to example 4.b. of the invention.

On the basis of chiral HPLC the desired enantiomer, no distomer contamination, HPLC purity: 99.76% (Chiral HPLC: FIG. 4)

EXAMPLE 13

The Production of Lumateperone (I) p-toluenesulfonic Acid Amorphous Salt

The 80 mg ITI-007 monotosylate produced according to example 12 is dissolved in a mixture of 250 ml water and 12.5 ml acetonitrile. The solution obtained was distributed among two 500 ml flasks, and then these were lyophilised. The content of the flasks was frozen using an acetone dry ice bath. Following this the two flasks were connected to the lyophilising device and the freeze drying was carried out at −80° C., at a pressure of 3.6 mbar until constant weight was achieved. A loose structured, white substance was obtained.

$^1$H-NMR (DMSO-d$_6$, 400 MHz): 9.18/9.42 (b, 1H), 8.04 (~dd, J$_1$=5.6 Hz, J$_2$=8.8 Hz, 2H), 7.50 (~d, J=8.1 Hz, 2H), 7.36 (~t, J=8.8 Hz, 2H), 7.11 (~d, J=8.0 Hz, 2H), 6.60 (m, 1H), 6.51 (m, 1H), 6.42 (m, 1H), 3.58 (m, 1H), 3.46 (m, 1H), 3.45 (m, 1H), 3.40 (m, 1H), 3.33 (m, 1H), 3.31 (m, 1H), 3.20 (m, 1H), 3.12 (m, 2H), 3.11 (t, J=7.0 Hz, 2H), 3.03 (m, 1H), 2.81 (s, 3H), 2.56 (m, 1H), 2.27 (s, 3H), 2.23 (m, 1H), 2.12 (m, 1H), 2.01 (m, 2H) ppm.

$^{13}$C-NMR (DMSO-d$_6$, 100 MHz): 197.36; 165.24 (d, J=251.6 Hz); 145.58; 138.00; 137.47; 135.37; 133.28 (d, J=2.7 Hz); 131.07 (d, J=9.5 Hz); 128.30; 126.92; 125.65; 120.76; 115.89 (d, J=22.0 Hz); 112.68; 109.52; 62.38; 55.73; 52.71; 49.97; 47.92; 43.91; 38.71; 37.17; 35.07; 21.85; 20.93; 18.19 ppm.

EXAMPLE 14

The Formula (VIII) Salt of Lumateperone Formed with naphthalene-2-sulfonic acid, in which the Molar Ratio of Lumateperone to naphthalene-2-sulfonic scid is 1:2

Figure 8:
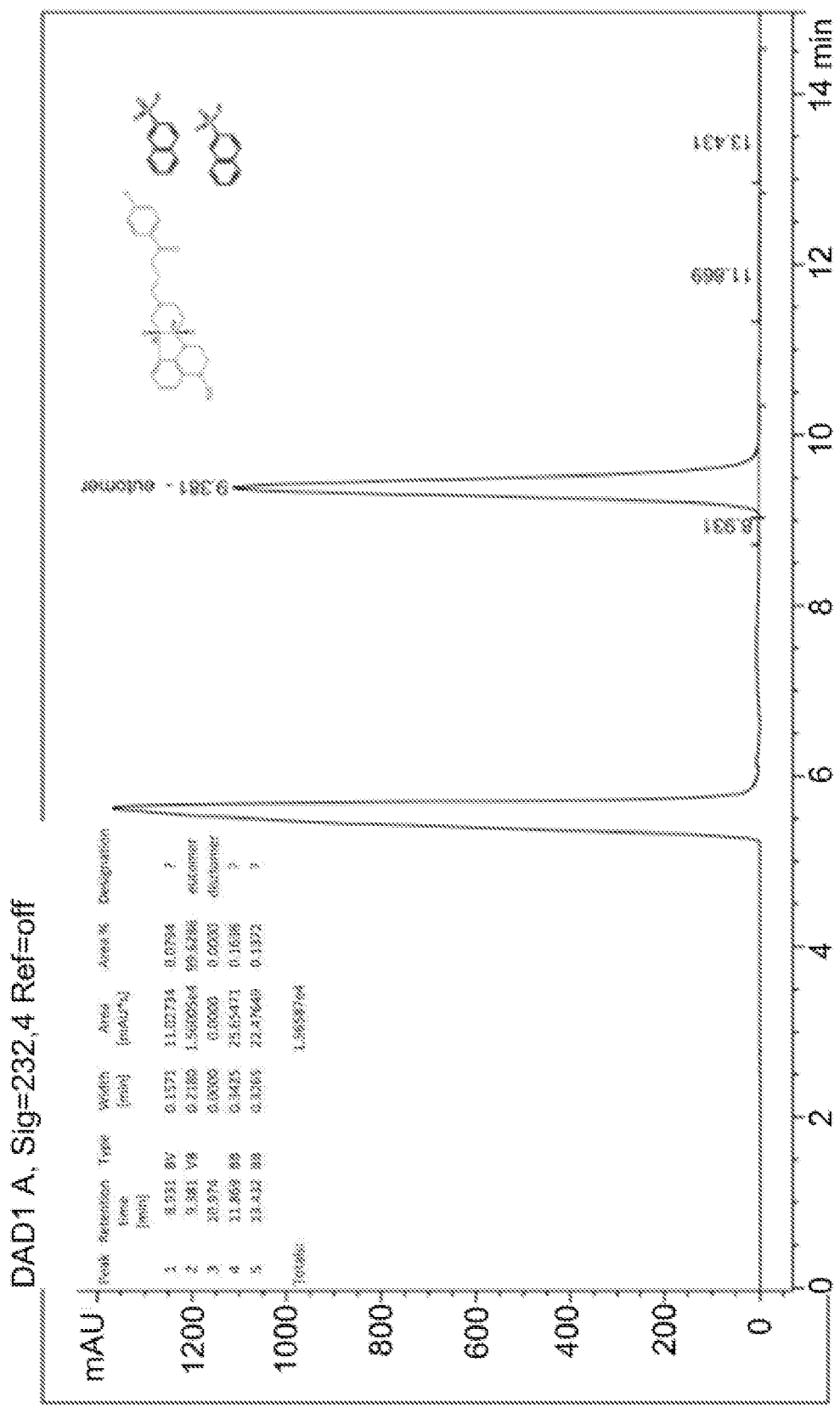
FIG. 8.) The chiral HPLC chromatogram of the formula (VIII) salt produced according to example 14 of the invention.
Figure 9:
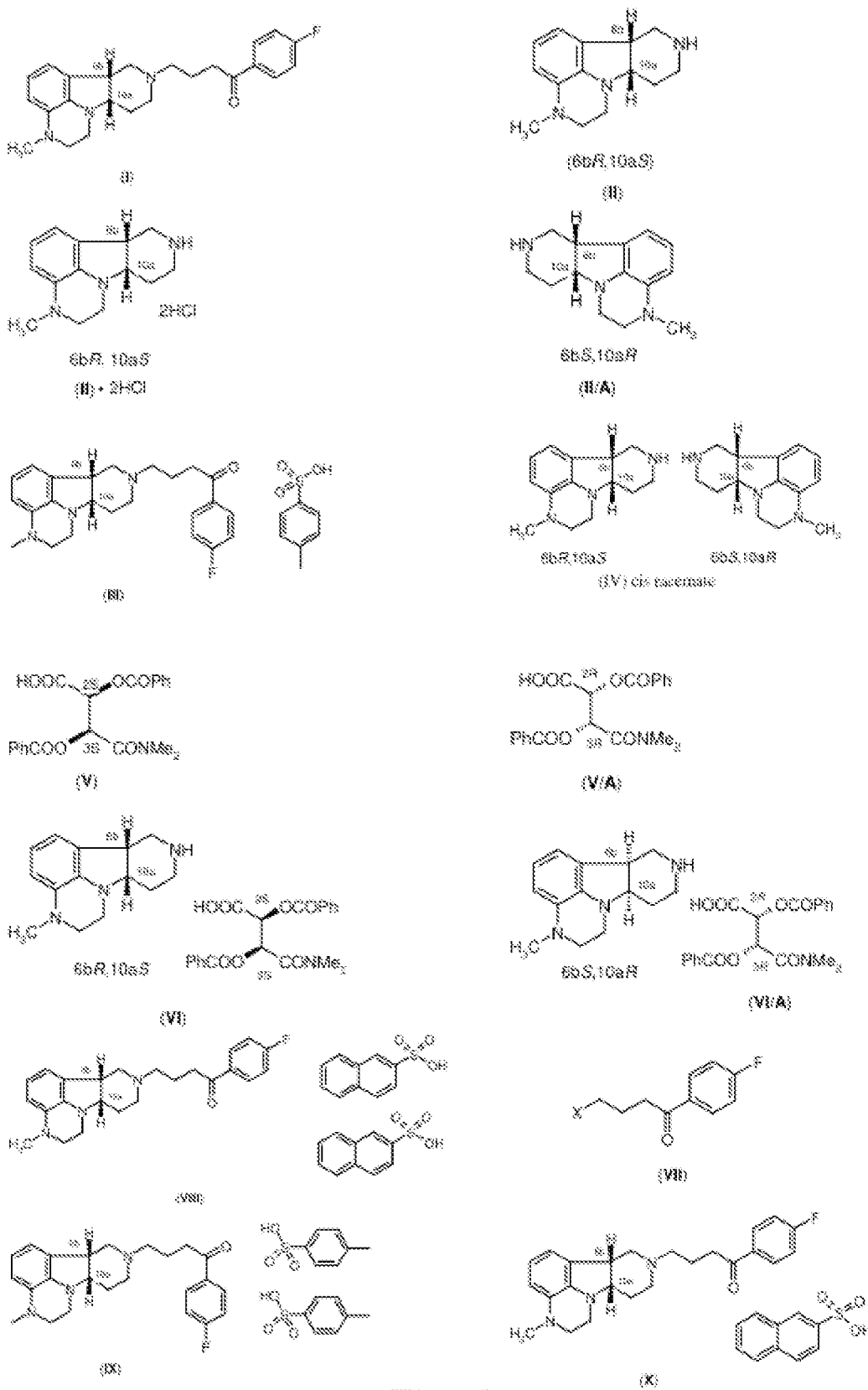
FIG. 9.) The structural formulae of the starting materials, intermediates and products used in the methods according to the invention.
Figure 10:
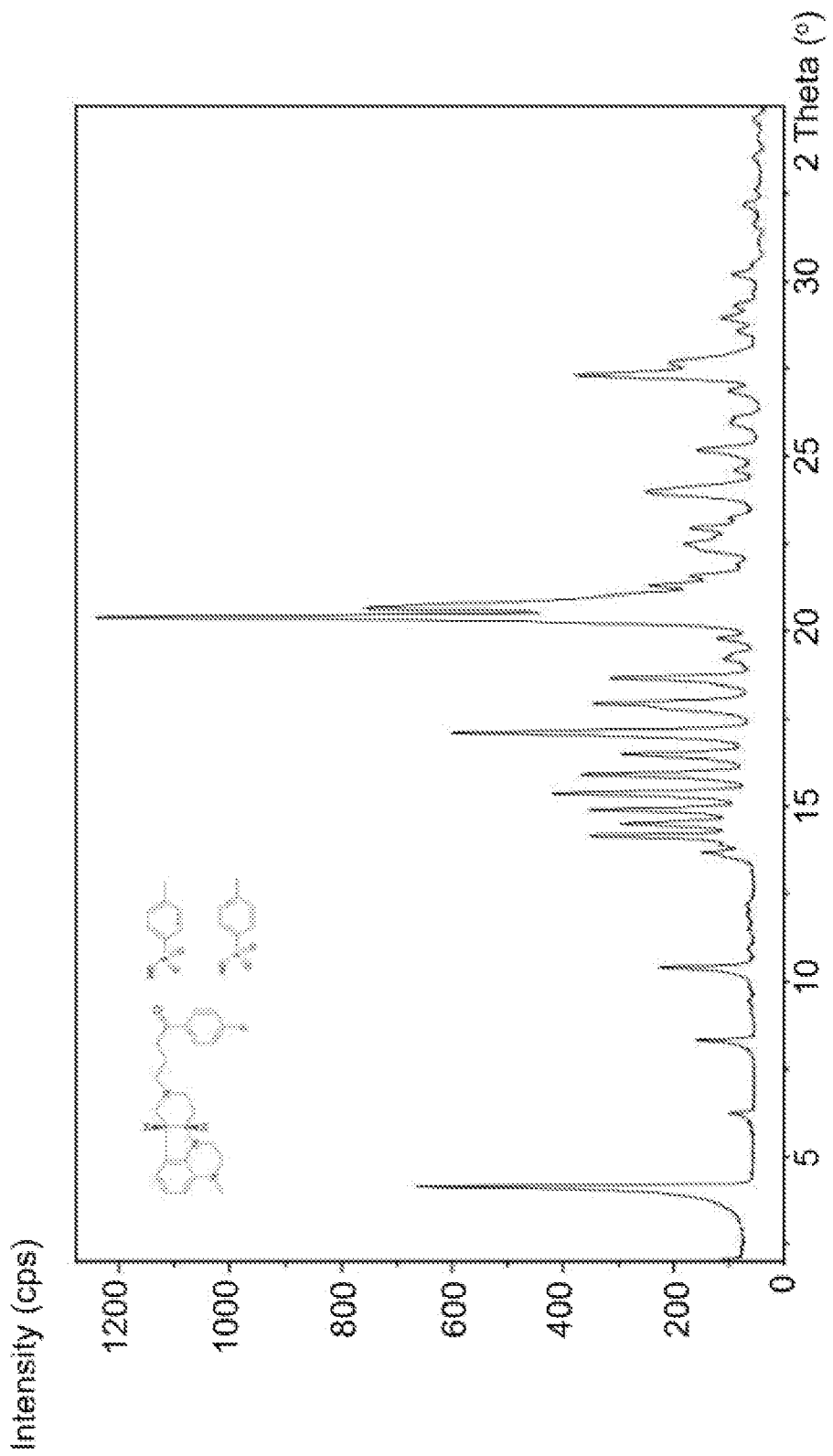
FIG. 10.) The x-ray powder diffractogram of the formula (IX) salt produced according to example 16 of the invention.
Figure 11:
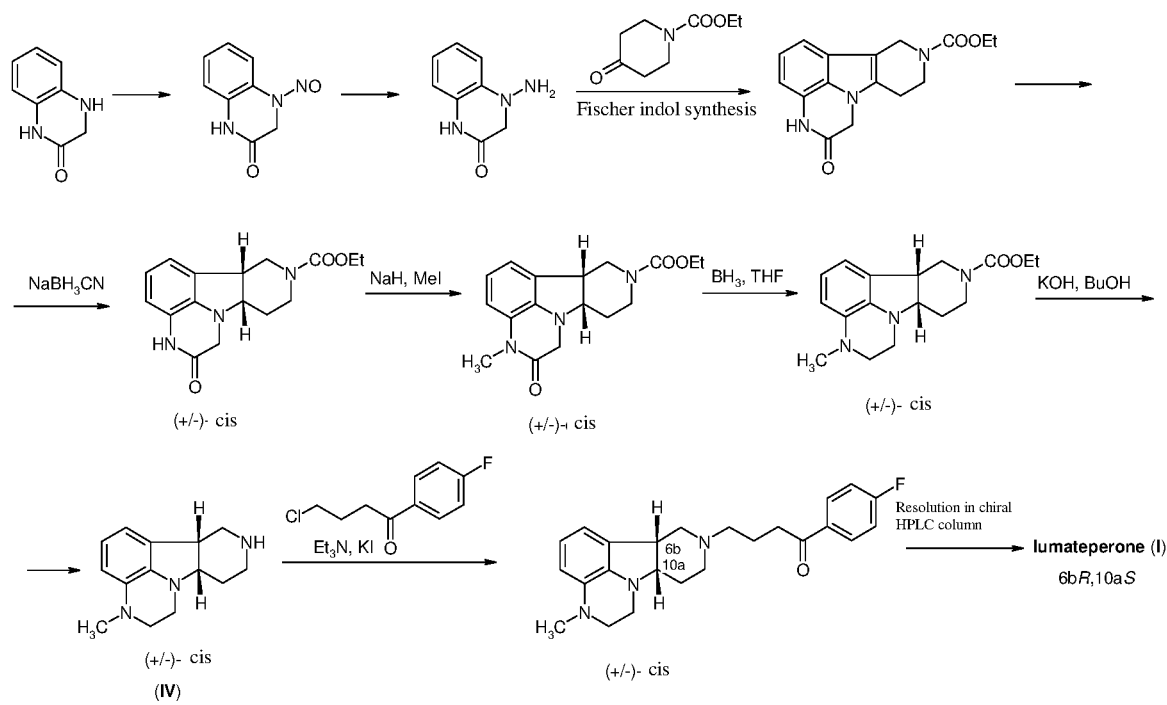
FIG. 11.) Illustrates Reaction Scheme 1.
Figure 12:
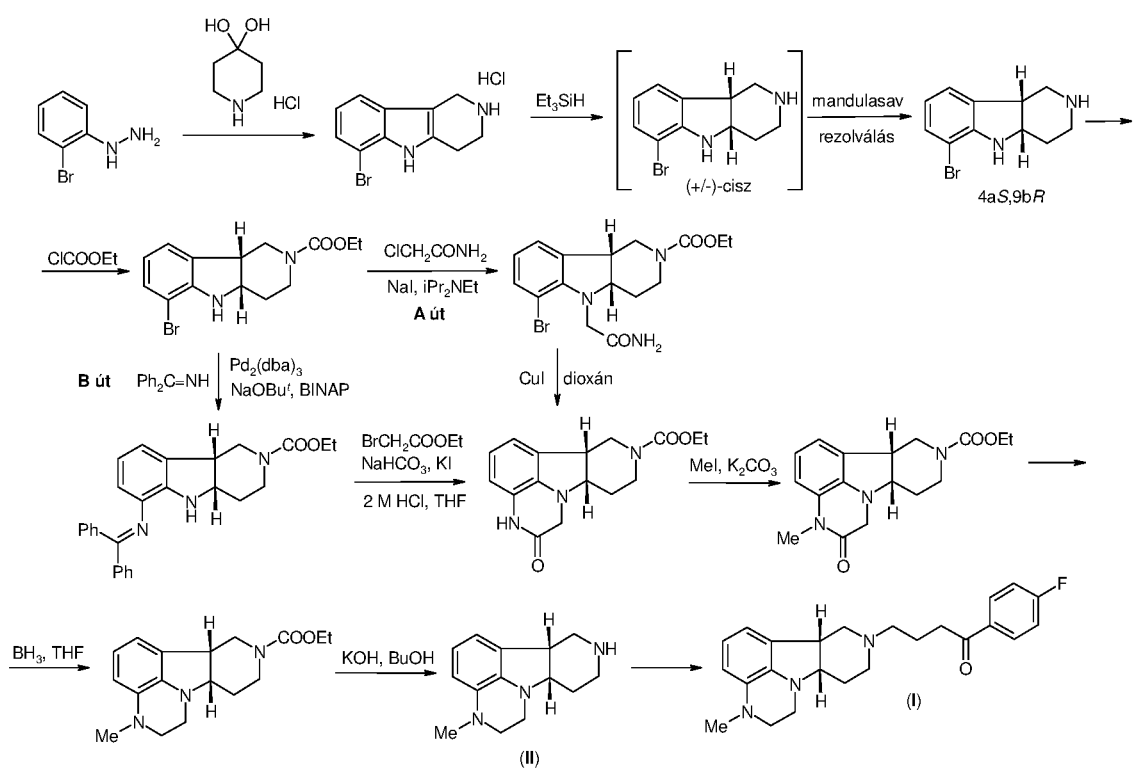
FIG. 12.) Illustrates Reaction Scheme 2.
Figure 13:
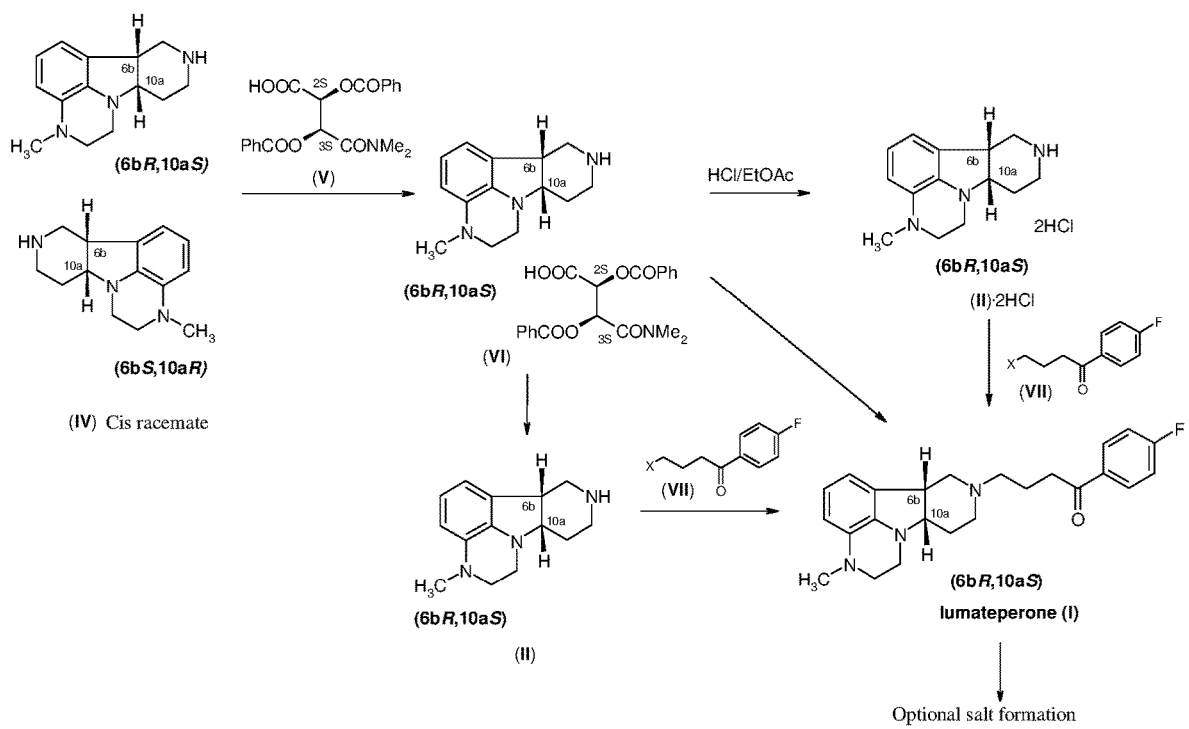
FIG. 13.) Illustrates Reaction Scheme 3.

1.5 g (3.81 mmol) of the formula (I) lumateperone base according to example 9 is dissolved in 12 ml acetone. The acetone solution of naphthalene-2-sulfonic acid monohydrate (1.726 g, 7.62 mmol) is prepared separately using 2 ml acetone. The acetone solution of naphthalene-2-sulfonic acid monohydrate is added drop by drop at room temperature to the lumateperone base solution in an argon atmosphere. A white crystalline substance precipitates. The suspension is stirred for 1 day at room temperature, then cooled in a ice and water bath, then the crystalline substance is filtered out. The product is then washed on the filter with a little cold acetone. The filtered lumateperone dinapsylate salt is dried until constant weight at 40° C., 2.5 g (83%). The raw product can be further purified using acetonitrile recrystallization (250 ml). 1.8 g (60%) white crystals, mp: 188-192° C. $[\alpha]_D^{25}$=4.4 (c=1.00, DMF). HPLC purity: 99.628% (FIG. 8)

IR (KBr): 3006, 2621, 2400, 1678, 1599, 1482, 1237, 1167, 1086, 1026, 676 cm$^{-1}$.

$^1$H-NMR (DMSO-d$_6$, 400 MHz): 9.10 (b, 1H), 8.14 (bs, 2*1H), 8.04 (~dd, J$_1$=5.6 Hz, J$_2$=8.8 Hz, 2H), 7.97 (m, 2*1H), 7.90 (m, 2*1H), 7.86 (d, J=8.5 Hz, 2*1H), 7.71 (dd, J$_1$=1.7 Hz, J$_2$=8.5 Hz, 2*1H), 7.53 (m, 2*1H), 7.51 (m, 2*1H), 7.37 (~t, J=8.8 Hz, 2H), 6.61 (m, 1H), 6.53 (m, 1H), 6.44 (m, 1H), 3.60 (m, 1H), 3.46 (m, 1H), 3.45 (m, 1H), 3.45 (m, 1H), 3.41 (m, 1H), 3.35 (m, 1H), 3.33 (m, 1H), 3.23 (m, 1H), 3.13 (m, 2H), 3.11 (m, 1H), 3.08 (m, 1H), 3.03 (m, 1H), 2.81 (m, 3H), 2.70 (m, 1H), 2.57 (m, 1H), 2.26 (m, 1H), 2.06 (m, 1H), 2.03 (m, 1H), 2.00 (m, 1H) ppm.

$^{13}$C-NMR (DMSO-d$_6$, 100 MHz): 197.37; 165,25 (d, J=251.6 Hz); 145.74; 137.67w; 135.46w; 133.27 (d, J=2.9

Hz); 132,90; 132.32; 131.06 (d, J=9.5 Hz); 128.63; 127.63; 127.49; 127.12w; 126.61; 126.47; 124.21; 124.14; 120.87w; 115 92 (d, J=22.0 Hz); 113.42w; 110.07w; 62.30; 55.72; 52.66; 50.07; 47.93; 43.74; 37.56w; 35.02; 21.88; 18.20 (w: weak) ppm.

COSY: 8.14-7.71-7.86, 8.04-7.37, 7.97-7.51-7.53-7.90, 6.53-6.61-6.44, (3.60, 2.57)-3.33-3.23-(2.26, 2.06)-(3.45, 3.03), (3.46, 3.35)-(3.41, 2.70), 3.13-(2.03, 2.00)-(3.11, 3.08).

HSQC (140 Hz): 8.14-124.21, 8.04-131.06, 7.97-128.63, 7.90-127.63, 7.86-127.49, 7.71-124.14, 7.53-126.61, 7.51-126.47, 7.37-115.92, 6.61-120.87, 6.53-113.42, 6.44-110.07, 3.60-52.66, 3.46-50.07, 3.45-47.93, 3.41-43.74, 3.35-50.07, 3.33-38.81, 3.23-62.30, 3.13-35.02, 3.11-55.72, 3.08-55.72, 2.81-37.56, 2.70-43.74, 2.57-52.66, 2.26-21.88, 3.03-47.93, 2.06-21.88, 2.03-18.20, 2.00-18.20.

HMBC (140 Hz, 8 Hz): 8.14-(132.90, 128.63, 124.14), 8.04-(197.37, 165.25, 131.06), 7.97-(132.90, 126.61), 7.90-(132.32, 126.47), 7.86-(145.74, 132.32), 7.71-(132.90, 124.21), 7.53-(132.90, 128.63), 7.51-(132.32, 127.63), 7.37-(165.25, 133.27, 115.92), 6.61-135.46, 6.53-110.07, 6.44-137.67, 3.13-(197.37, 18.20), (3.11, 3.08)-18.20.

Figure 7:
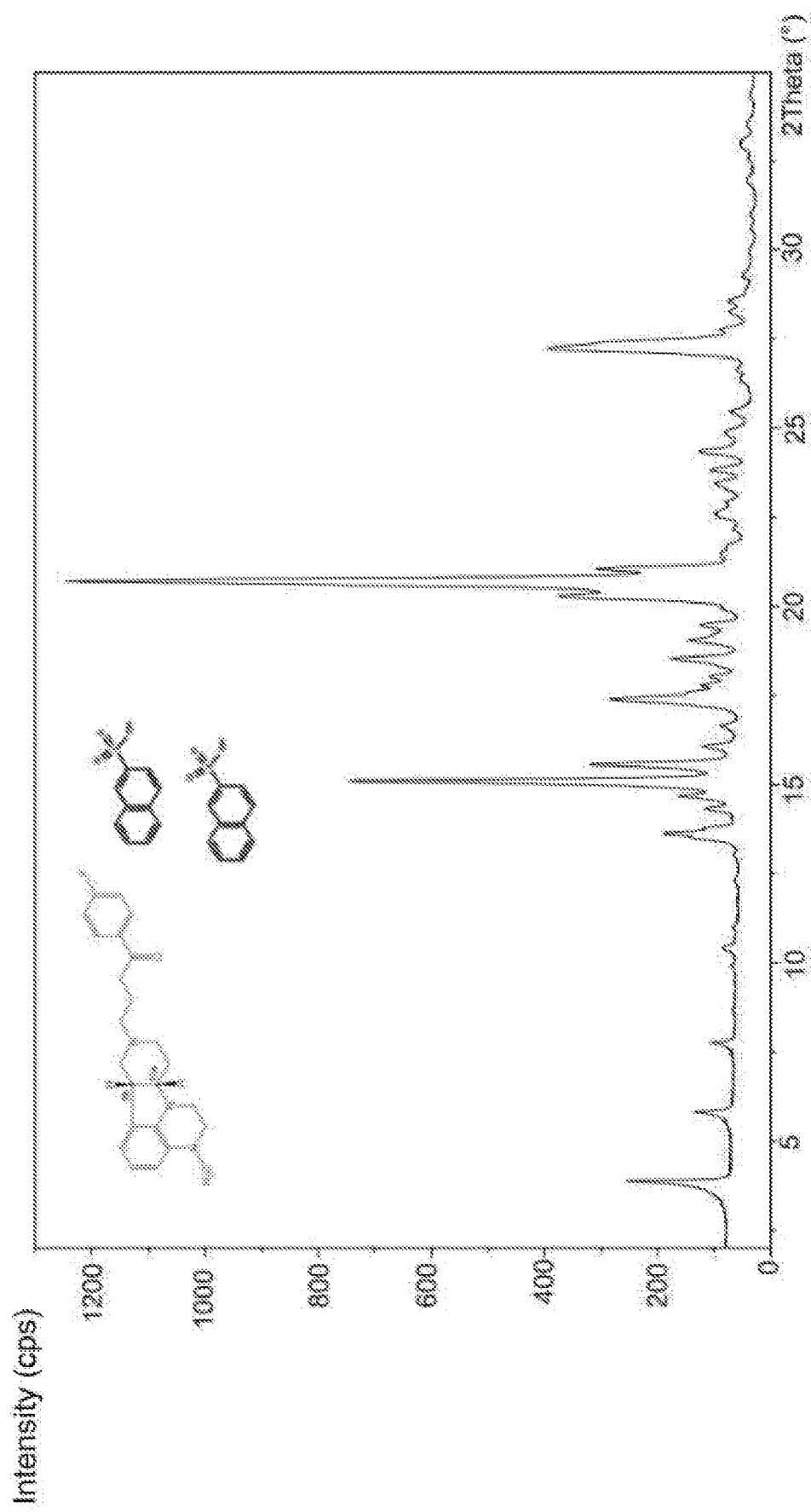
FIG. 7.) The x-ray powder diffractogram of the formula (VIII) salt produced according to example 14 of the invention.

X-Ray Powder Diffractogram: FIG. 7

The Thermal Characterisation of the Lumateperone Dinapsylate Salt (TG, DSC)

The crystalline form of the lumateperone dinapsylate salt may be characterised using thermoanalysis techniques. In the course of thermogravimetric testing (TG) a maximum of 0.2% mass loss may be observed in the course of heating up to 190° C., on the basis of which the crystalline form of lumateperone dinapsylate salt is a water and solvent-free form. In the course of differential scanning calorimetry testing (DSC) in the course of heating up to 200° C. an endothermic peak may be detected with an onset value around 189.0° C., and with a peak value of 192.2° C., on the basis of which the melting point of the crystalline form of lumateperone dinapsylate salt is around 189.0° C.

EXAMPLE 15

The Formula (X) Salt of Lumateperone Formed with naphthalene-2-sulfonic acid, in which the Molar Ratio of Lumateperone to naphthalene-2-sulfonic acid is 1:1

1.00 g (2.54 mmol) formula (I) lumateperone base according to example 9 is dissolved in 6 ml acetone and in an argon atmosphere 0.575 g (2.54 mmol) naphthalene-2-sulfonic acid monohydrate is added to this in a single portion. The salt precipitates almost immediately after the acid has been dissolved. The suspension is stirred at room temperature for 24 hours, then cooled for 30 minutes in an ice and water bath. The salt is filtered using a glass filter, then washed with about 0.5 ml cold acetone. 1.10 g mononapsylate is obtained, which is purified further by recrystallization from 60 ml isopropanol. 0.92 g white crystalline product is obtained, mp: 165-172° C.

$^1$HNMR (DMSO-$d_6$, 400 MHz): 8.14 (d, J=0.6 Hz, 1H), 8.04 (~dd, $J_1$=5.5 Hz, $J_2$=9.0 Hz, 2H), 7.97 (m, 1H), 7.90 (m, 1H), 7.86 (d, J=8.6 Hz, 1H), 7.71 (dd, $J_1$=1.6 Hz, $J_2$=8.5 Hz, 1H), 7.52 (m, 2H), 7.37 (~t, J=8.9 Hz, 2H), 6.60 (m, 1H), 6.52 (m, 1H), 6.43 (m, 1H), 3.60 (m, 1H), 3.46 (m, 1H), 3.45 (m, 1H), 3.41 (m, 1H), 3.32 (m, 1H), 3.31 (m, 1H), 3.23 (m, 1H), 3.12 (m, 2H), 3.10 (m, 1H), 3.08 (m, 1H), 3.03 (m, 1H), 2.81 (s, 3H), 2.71 (m, 1H), 2.57 (m, 1H), 2.25 (m, 1H), 2.06 (m, 1H), 2.02 (m, 2H) ppm.

EXAMPLE 16

The Production of the Formula (IX) Lumateperone p-toluenesulfonic acid salt, in which the Molar Ratio of the Lumateperone and the p-toluenesulfonic acid is 1:2

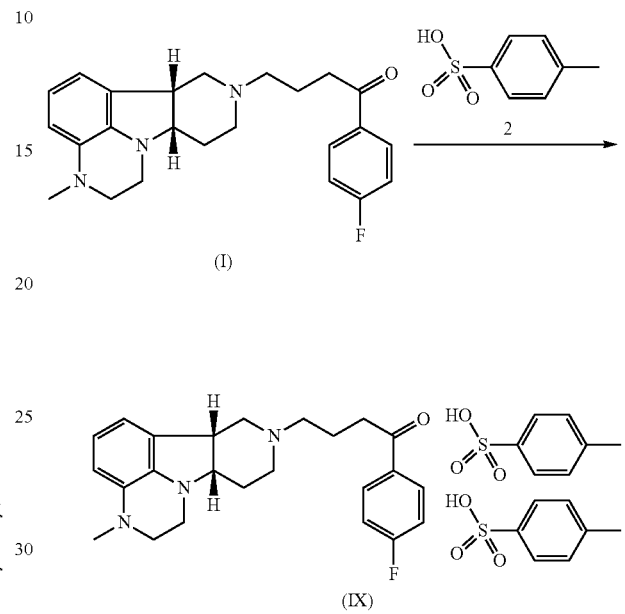

250 mg (0.636 mmol) lumateperone base is dissolved in 1.5 ml acetone, then 241.8 mg (1.271 mmol) p-toluenesulfonic acid monohydrate is added to this in an argon atmosphere. White crystals are formed approx. 1 minute after the p-toluenesulfonic acid has been dissolved. The reaction mixture is stirred at room temperature for 24 hours. Following this it is cooled to 0° C. and the white crystalline substance is filtered out, then washed with cold acetone. The product obtained is recrystallized from 21 ml 2-propanol and dried at 40° C. in a vacuum until constant weight. 270 mg of product is obtained, mp: 193-196° C. [α]$D_{25}$=5.0 (c=1.00, DMF) Chiral HPLC: 99.56% (distomer contamination 0%)

Element Analysis:

Calculated: C, 61.85; H, 6.01; N, 5.69; S, 8.69.

Measured: C, 61.68; H, 6.01; N, 5.69; S, 8.72.

IR (KBr): 3000, 2274, 1684, 1601, 1482, 1241, 1165, 1030, 1008, 683, 568 cm$^{-1}$.

$^1$H-NMR (DMSO-$d_6$, 400 MHz): 8.04 (~dd, $J_1$=5.6 Hz, $J_2$=8.8 Hz, 2H), 7.49 (~d, J=8.1 Hz, 4H), 7.37 (~t, J=8.8 Hz, 2H), 7.12 (~d, J=7.9 Hz, 4H), 6.61 (b, 1H), 6.53 (b, 1H), 6.21 (b, 1H), 3.58 (m, 1H), 3.46 (m, 1H), 3.45 (m, 1H), 3.40 (m, 1H), 3.33 (m, 1H), 3.31 (m, 1H), 3.20 (m, 1H), 3.12 (m, 4H), 3.03 (m, 1H), 2.85 (b, 3H), 2.71 (m, 1H), 2.56 (m, 1H), 2.30 (m, 1H), 2.29 (s, 6H), 2.05 (m, 1H), 2.01 (m, 2H) ppm.

$^{13}$C-NMR (DMSO-$d_6$, 100 MHz): 197.38; 165.25 (d, J=251.7 Hz); 145.60; 137.99; 137.82; 134.24; 133.29 (d, J=2.8 Hz); 131.08 (d, J=9.5 Hz); 128.30; 127.46; 125.67; 120.79; 115.92 (d, J=21.8 Hz); 113.90; 110.75; 62.40; 5.74; 52.62; 50.26; 47.89; 43.43; 38.71; 37.95; 35.06; 21.86; 20.96; 18.19 ppm.

The invention claimed is:

1. A

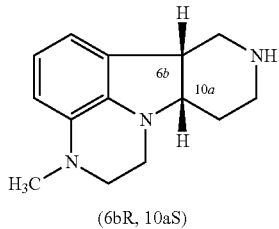

(6bR, 10aS)

salt of formula (VI)

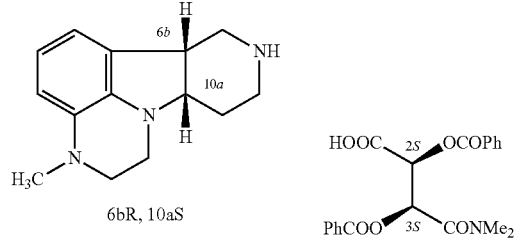

(6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide), or a salt of formula (II)

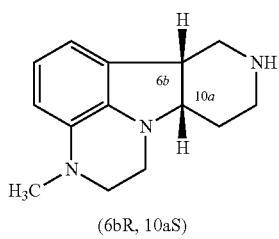

(6bR, 10aS)

(6bR,10aS)-3-methyl-2,3,6b,9,10,10a-hexahydro-1H-pyrido[3',4': 4,5]pyrrolo[1,2,3-de]quinoxaline formed with hydrochloric acid, or the salt of formula (I) lumateperone formed with naphthalene-2-sulfonic acid,

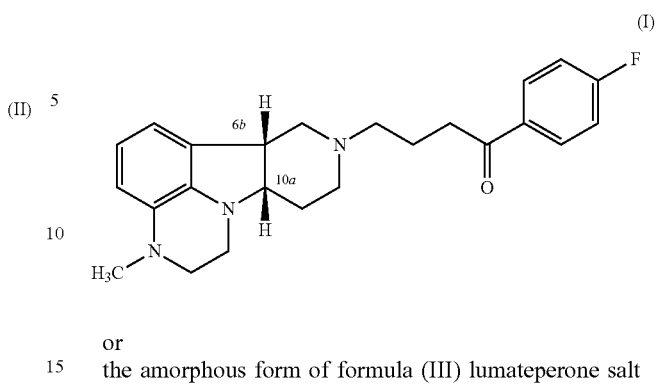

or the amorphous form of formula (III) lumateperone salt

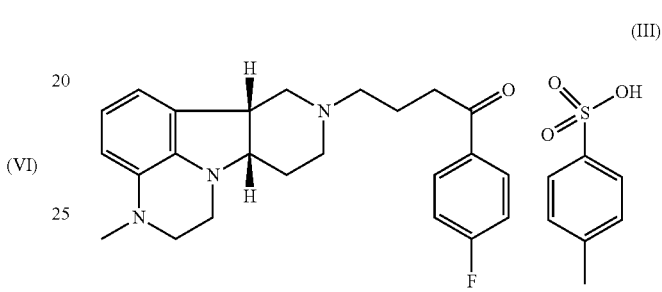

in which salt the molar ratio of lumateperone and the p-toluenesulfonic acid is 1:1.

2. A compound according to claim 1, wherein the enantiomer purity of a compound of formula (II) or (I) or a salt thereof, in which the configuration of the chiral carbon atoms is 6bR,10aS, is greater than 97%.

3. A compound according to claim 1, wherein the chemical purity of a compound of formula (II) or (I) or a salt thereof, in which the configuration of the chiral carbon atoms is 6bR,10aS, is greater than 97%.

4. A compound according to claim 1, which is a salt of formula (I) lumateperone formed with naphthalene-2-sulfonic acid.

5. A compound according to claim 1, which is a salt of formula (I) lumateperone formed with naphthalene-2-sulfonic acid being of formula (X)

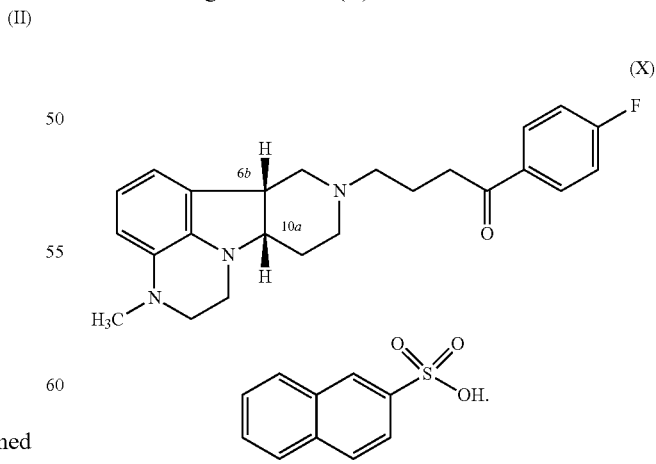

6. A compound according to claim 5, wherein the molar ratio of the lumateperone and the naphthalene-2-sulfonic acid is 1:1.

7. A compound according to claim 1, which is the amorphous form of formula (III) lumateperone salt

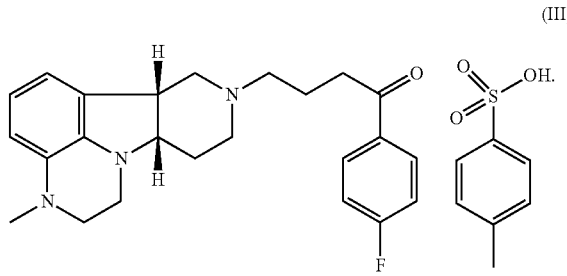

(III)

8. A compound according to claim 7, wherein the molar ratio of lumateperone and the p-toluenesulfonic acid is 1:1.

9. A compound according to claim 1, which is a salt of formula (I) lumateperone formed with naphthalene-2-sulfonic acid being of formula (VIII)

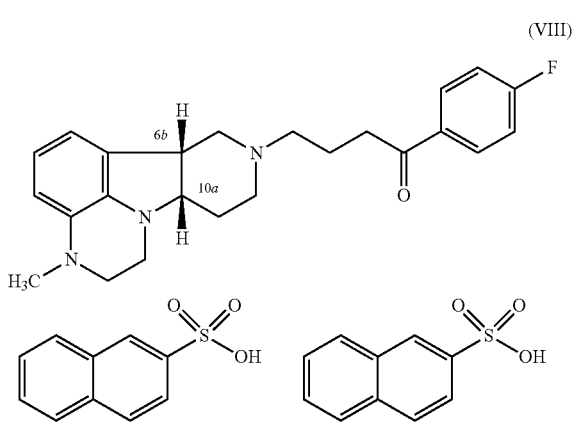

(VIII)

in which salt the molar ratio of the lumateperone and the naphthalene-2-sulfonic acid is 1:2.

10. A compound, which is a crystalline form of formula (II)

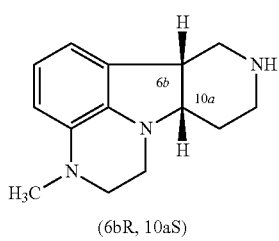

(II)

(6bR, 10aS)

and which is characterized by x-ray powder diffraction lines as follows: [(Cu Kα) ° 2θ(±0.2 °2θ)]: 9.99; 16.03; 20.87.

11. A compound according to claim 1, which is a salt of formula (VI) and which is characterized by x-ray powder diffraction lines as follows: [(Cu Kα) ° 2θ(±0.2 °2θ)]: 6.17; 19.88; 23.58.

12. A compound according to claim 1, which is a salt of formula (II) formed with hydrochloric acid and which is characterized by x-ray powder diffraction lines as follows: [(Cu Kα) °2θ(±0.2 °2θ)]:13.43; 16.52; 22.1.

13. A compound according to claim 1, which is of formula (VIII)

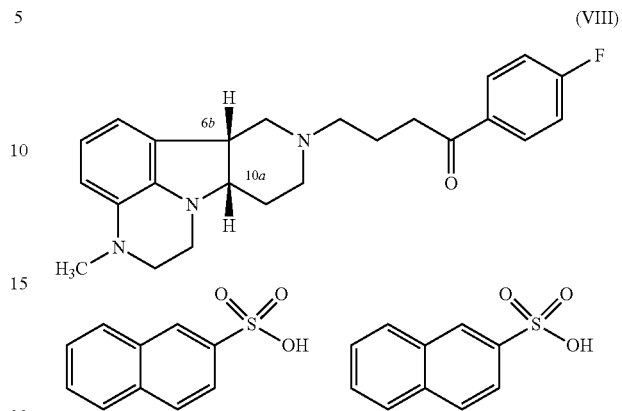

(VIII)

and which is characterized by x-ray powder diffraction lines as follows: [(Cu Kα) °2θ(±0.2 °2θ)]: 3.87; 15.09; 20.71.

14. A compound according to claim 1, wherein the enantiomer purity of a compound of formula (II) or (I) or a salt thereof, in which the configuration of the chiral carbon atoms is 6bR,10aS, is greater than 99.5%.

15. A compound according to claim 1, wherein the chemical purity of a compound of formula (II) or (I) a salt thereof, in which the configuration of the chiral carbon atoms is 6bR,10aS, is greater than 99.5%.

16. A pharmaceutical composition, comprising a compound according to claim 1, which is a salt of formula (I) lumateperone formed with naphthalene-2-sulfonic acid, and a pharmaceutically acceptable excipient.

17. A pharmaceutical composition, comprising a compound according to claim 1, which is a salt of formula (I) lumateperone formed with naphthalene-2-sulfonic acid being of formula (X)

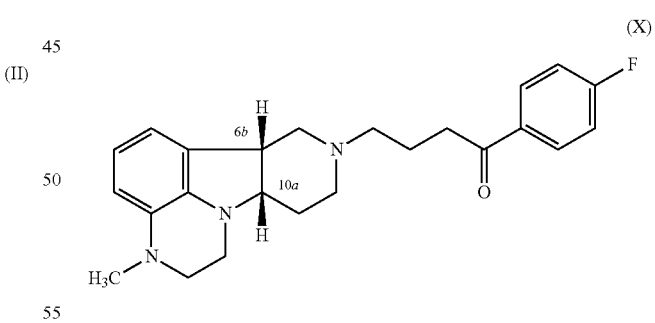

(X)

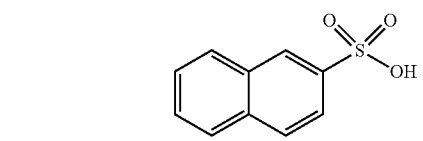

or which is the amorphous form of formula (III) lumateperone salt, and a pharmaceutically acceptable excipient.

18. A method for producing the crystalline form of formula (II)

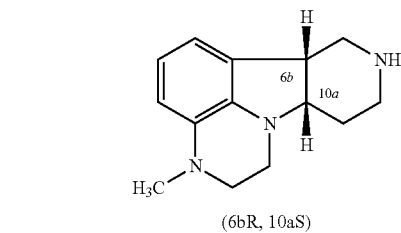

(6bR, 10aS)

(6bR,10aS)-3-methyl-2,3,6b,9,10,10a-hexahydro-1H-pyrido[3',4': 4,5]pyrrolo[1,2,3-de]quinoxaline base, comprising a.) reacting the compound of formula (VI) salt

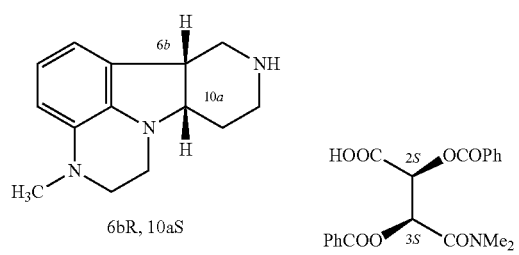

formed with (+)-dibenzoyl-D-tartaric acid mono(dimethylamide), or the compound of formula (II) salt formed with hydrochloric acid, with a base, and the resultant released formula (II) compound is brought into crystalline form, or b.) reacting the formula (IV) cis racemate compound

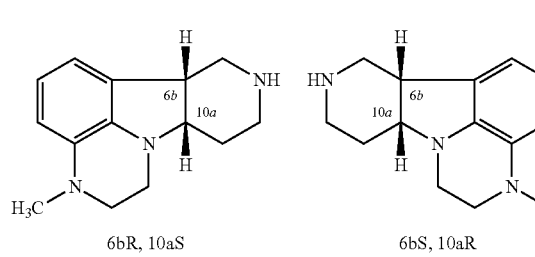

with a chiral acid, then a salt of formula (II) compound formed with a chiral acid, in which the configuration of the chiral carbon atoms is 6bR,10aS, is isolated from a reaction mixture and then transformed into formula (II) base, or c.) reacting the formula (IV) compound with chiral acid, then a salt of formula (II/A) compound formed with a chiral acid, wherein the configuration of the chiral carbon atoms is 6bS,10aR,

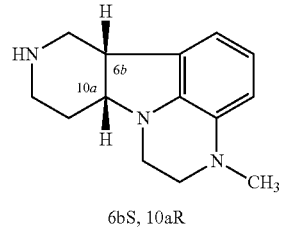

is separated from a reaction mixture, and the resultant formula (II) compound that has been enriched in the reaction mixture, wherein the configuration of the chiral carbon atoms is 6bR,10aS, is isolated, then the formula (II) compound obtained is crystallized;

or for producing the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide), comprising a.) reacting the formula (IV) compound with the formula (V) (+)-dibenzoyl-D-tartaric acid mono(dimethylamide),

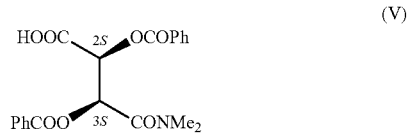

then the formula (VI) compound obtained is isolated from a reaction mixture, or b.) reacting the formula (IV) compound with a chiral acid, then the salt of compound (II/A) formed with chiral acid, in which the configuration of the chiral carbon atoms is 6bS,10aR, is isolated from a reaction mixture, and the resultant formula (II) compound enriched in the reaction mixture is reacted with the formula (V) (+)-dibenzoyl-D-tartaric acid mono(dimethylamide),

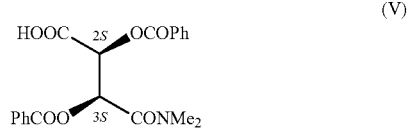

then the formula (VI) compound formed is isolated;

or for producing a formula (II)·2HCl salt, comprising stirring the formula (VI) salt of (6bR,10aS)-3-methyl-2,3,6b,9,10,10a-hexahydro-1H-pyrido[3',4': 4,5]pyrrolo[1,2,3-de]quinoxaline formed with (+)-dibenzoyl-D-tartaric acid mono(dimethylamide) or the formula (II) base in an organic solvent to form a reaction mixture, then hydrochloric acid dissolved in an organic solvent is added to the reaction mixture, then the formula (II)·2HCl salt formed is separated.

19. A method for preparing a salt of lumateperone formed with p-toluenesulfonic acid according to claim 1, comprising reacting lumateperone base with an amount of p-toluenesulfonic acid equal to 0.7 to 1.2 times the molar amount of the lumateperone base, then the salt obtained a.) is isolated in amorphous form, then the formula (III) lumateperone p-toluenesulfonic acid salt solution obtained is lyophilised or b.) the formula (III) lumateperone p-toluenesulfonic acid salt formed, which consists of morphologically uniform crystals, or consists of several crystals of different morphology, or of a mixture of crystalline and amorphous tosylate salt of various morphology is isolated, then dissolving in a mixture of water and a nitrile type solvent and then is lyophilised.

20. A method for producing a salt of lumateperone with naphthalene-2-sulfonic acid according to claim 1, comprising reacting the formula (I) lumateperone base with naphthalene-2-sulfonic acid.

\* \* \* \* \*